United States Patent
Armstrong

(10) Patent No.: US 9,610,362 B2
(45) Date of Patent: Apr. 4, 2017

(54) ANTISENSE CONJUGATES FOR DECREASING EXPRESSION OF DMPK

(71) Applicant: Valerion Therapeutics, LLC, Concord, MA (US)

(72) Inventor: Dustin D. Armstrong, Quincy, MA (US)

(73) Assignee: Valerion Therapeutics, LLC, Concord, MA (US)

( * ) Notice: Subject to any disclaimer, the term of this patent is extended or adjusted under 35 U.S.C. 154(b) by 39 days.

(21) Appl. No.: 14/385,724

(22) PCT Filed: Mar. 14, 2013

(86) PCT No.: PCT/US2013/031718
§ 371 (c)(1),
(2) Date: Sep. 16, 2014

(87) PCT Pub. No.: WO2013/138662
PCT Pub. Date: Sep. 19, 2013

(65) Prior Publication Data
US 2015/0064181 A1 Mar. 5, 2015

Related U.S. Application Data

(60) Provisional application No. 61/612,065, filed on Mar. 16, 2012.

(51) Int. Cl.
| C07H 21/04 | (2006.01) |
| A61K 47/48 | (2006.01) |
| A61K 31/7088 | (2006.01) |
| C07K 16/44 | (2006.01) |
| C12N 15/113 | (2010.01) |
| A61J 1/14 | (2006.01) |
| A61K 31/713 | (2006.01) |
| C07K 16/28 | (2006.01) |

(52) U.S. Cl.
CPC .......... *A61K 47/48561* (2013.01); *A61J 1/14* (2013.01); *A61K 31/7088* (2013.01); *A61K 31/713* (2013.01); *A61K 47/48776* (2013.01); *C07K 16/28* (2013.01); *C07K 16/44* (2013.01); *C12N 15/1137* (2013.01); *C12Y 207/11001* (2013.01); *C07K 2317/56* (2013.01); *C07K 2317/565* (2013.01); *C07K 2317/622* (2013.01); *C07K 2317/77* (2013.01); *C12N 2310/11* (2013.01); *C12N 2310/315* (2013.01); *C12N 2310/322* (2013.01); *C12N 2310/3231* (2013.01); *C12N 2310/3233* (2013.01); *C12N 2310/346* (2013.01); *C12N 2310/3513* (2013.01)

(58) Field of Classification Search
CPC .................................................. C07H 21/04
See application file for complete search history.

(56) References Cited

U.S. PATENT DOCUMENTS

| 3,687,808 A | 8/1972 | Merigan et al. |
| 4,469,863 A | 9/1984 | Ts'o et al. |
| 4,476,301 A | 10/1984 | Imbach et al. |
| 4,845,205 A | 7/1989 | Huynh Dinh et al. |
| 4,981,957 A | 1/1991 | Lebleu et al. |
| 5,013,830 A | 5/1991 | Ohtsuka et al. |
| 5,023,243 A | 6/1991 | Tullis |
| 5,034,506 A | 7/1991 | Summerton et al. |
| 5,118,800 A | 6/1992 | Smith et al. |
| 5,130,302 A | 7/1992 | Spielvogel et al. |
| 5,134,066 A | 7/1992 | Rogers et al. |
| 5,149,797 A | 9/1992 | Pederson et al. |
| 5,175,273 A | 12/1992 | Bischofberger et al. |
| 5,177,196 A | 1/1993 | Meyer, Jr. et al. |
| 5,188,897 A | 2/1993 | Suhadolnik et al. |
| 5,194,599 A | 3/1993 | Froehler et al. |
| 5,220,007 A | 6/1993 | Pederson et al. |
| 5,256,775 A | 10/1993 | Froehler |
| 5,264,423 A | 11/1993 | Cohen et al. |
| 5,276,019 A | 1/1994 | Cohen et al. |
| 5,278,302 A | 1/1994 | Caruthers et al. |
| 5,286,717 A | 2/1994 | Cohen et al. |
| 5,319,080 A | 6/1994 | Leumann |
| 5,321,131 A | 6/1994 | Agrawal et al. |
| 5,359,044 A | 10/1994 | Cook et al. |
| 5,366,878 A | 11/1994 | Pederson et al. |
| 5,367,066 A | 11/1994 | Urdea et al. |

(Continued)

FOREIGN PATENT DOCUMENTS

| WO | WO-88/03559 A1 | 5/1988 |
| WO | WO-90/02338 A1 | 3/1990 |

(Continued)

OTHER PUBLICATIONS

Abhinandan, K. R., et al., "Analyzing the "Degree of Humanness" of Antibody Sequences," Journal of Mol. Biol., 369:852-862 (2007).

Ashizawa et al., "Somatic instability of CTG repeat in myotonic dystrophy," Neurology, vol. 43(12), pp. 2674-2678 (1993).

Astriab-Fisher et al., "Conjugates of Antisense Oligonucleotides with the Tat and Antennapedia Cell-Penetrating Peptides: Effects on Cellular Uptake, Binding to Target Sequences, and Biologic Actions," Pharmaceutical Research, vol. 19(6): 744-754 (2002).

Brook et al., "Molecular Basis of Myotonic Dystrophy: Expansion of a Trinucleotide (CTG) Repeat at the 3' End of a Transcript Encoding a Protein Kinase Family Member," Cell, vol. 68: 799-808 (1992).

(Continued)

*Primary Examiner* — Kimberly Chong
(74) *Attorney, Agent, or Firm* — Ropes & Gray LLP

(57) ABSTRACT

The disclosure provides novel conjugates comprising antisense oligonucleotides that hybridize to a DMPK transcript and a 3E10 antibody or binding fragment thereof. Also considered are these conjugates further comprising MBNL1 polypeptides. Methods of treating myotonic dystrophy using these conjugates and kits comprising these conjugates are also considered. Wherein the conjugates are suitable for delivery to muscle cells.

38 Claims, No Drawings

(56) References Cited

U.S. PATENT DOCUMENTS

| | | |
|---|---|---|
| 5,393,878 A | 2/1995 | Leumann |
| 5,399,676 A | 3/1995 | Froehler |
| 5,403,711 A | 4/1995 | Walder et al. |
| 5,405,939 A | 4/1995 | Suhadolnik et al. |
| 5,432,272 A | 7/1995 | Benner |
| 5,446,137 A | 8/1995 | Maag et al. |
| 5,453,496 A | 9/1995 | Caruthers et al. |
| 5,455,233 A | 10/1995 | Spielvogel et al. |
| 5,457,187 A | 10/1995 | Gmeiner et al. |
| 5,459,255 A | 10/1995 | Cook et al. |
| 5,466,677 A | 11/1995 | Baxter et al. |
| 5,466,786 A | 11/1995 | Buhr et al. |
| 5,476,925 A | 12/1995 | Letsinger et al. |
| 5,484,908 A | 1/1996 | Froehler et al. |
| 5,491,133 A | 2/1996 | Walder et al. |
| 5,502,177 A | 3/1996 | Matteucci et al. |
| 5,514,785 A | 5/1996 | Van Ness et al. |
| 5,519,126 A | 5/1996 | Hecht |
| 5,519,134 A | 5/1996 | Acevedo et al. |
| 5,525,711 A | 6/1996 | Hawkins et al. |
| 5,527,899 A | 6/1996 | Froehler |
| 5,536,821 A | 7/1996 | Agrawal et al. |
| 5,539,082 A | 7/1996 | Nielsen et al. |
| 5,541,306 A | 7/1996 | Agrawal et al. |
| 5,550,111 A | 8/1996 | Suhadolnik et al. |
| 5,552,540 A | 9/1996 | Haralambidis |
| 5,563,253 A | 10/1996 | Agrawal et al. |
| 5,565,350 A | 10/1996 | Kmiec |
| 5,565,555 A | 10/1996 | Froehler et al. |
| 5,567,811 A | 10/1996 | Misiura et al. |
| 5,571,799 A | 11/1996 | Tkachuk et al. |
| 5,576,427 A | 11/1996 | Cook et al. |
| 5,587,361 A | 12/1996 | Cook et al. |
| 5,587,469 A | 12/1996 | Cook et al. |
| 5,591,722 A | 1/1997 | Montgomery et al. |
| 5,594,121 A | 1/1997 | Froehler et al. |
| 5,596,091 A | 1/1997 | Switzer |
| 5,597,909 A | 1/1997 | Urdea et al. |
| 5,602,240 A | 2/1997 | De Mesmaeker et al. |
| 5,610,300 A | 3/1997 | Altmann et al. |
| 5,614,617 A | 3/1997 | Cook et al. |
| 5,622,699 A | 4/1997 | Ruoslahti et al. |
| 5,623,065 A | 4/1997 | Cook et al. |
| 5,625,050 A | 4/1997 | Beaton et al. |
| 5,627,053 A | 5/1997 | Usman et al. |
| 5,639,873 A | 6/1997 | Barascut et al. |
| 5,645,985 A | 7/1997 | Froehler et al. |
| 5,646,265 A | 7/1997 | McGee |
| 5,652,355 A | 7/1997 | Metelev et al. |
| 5,652,356 A | 7/1997 | Agrawal |
| 5,658,873 A | 8/1997 | Bertsch-Frank et al. |
| 5,670,633 A | 9/1997 | Cook et al. |
| 5,672,697 A | 9/1997 | Buhr et al. |
| 5,681,941 A | 10/1997 | Cook et al. |
| 5,700,920 A | 12/1997 | Altmann et al. |
| 5,700,922 A | 12/1997 | Cook |
| 5,714,331 A | 2/1998 | Buchardt et al. |
| 5,719,262 A | 2/1998 | Buchardt et al. |
| 5,721,218 A | 2/1998 | Froehler |
| 5,763,588 A | 6/1998 | Matteucci et al. |
| 5,792,747 A | 8/1998 | Schally et al. |
| 5,830,653 A | 11/1998 | Froehler et al. |
| 6,005,096 A | 12/1999 | Matteucci et al. |
| 6,068,829 A | 5/2000 | Ruoslahti et al. |
| 6,174,687 B1 | 1/2001 | Rajotte et al. |
| 6,180,084 B1 | 1/2001 | Ruoslahti et al. |
| 6,232,287 B1 | 5/2001 | Ruoslahti et al. |
| 6,296,832 B1 | 10/2001 | Ruoslahti et al. |
| 6,303,573 B1 | 10/2001 | Ruoslahti et al. |
| 6,306,365 B1 | 10/2001 | Ruoslahti et al. |
| 7,189,396 B1 | 3/2007 | Weisbart |
| 7,863,017 B2 | 1/2011 | Ervasti et al. |
| 8,609,615 B2 | 12/2013 | Armstrong |
| 8,834,866 B2 | 9/2014 | Armstrong |
| 2008/0242629 A1* | 10/2008 | Crooke ............... C12N 15/113 514/44 A |
| 2008/0292618 A1 | 11/2008 | Weisbart |
| 2010/0111977 A1* | 5/2010 | Armstrong ............ C07K 14/47 424/178.1 |
| 2010/0143358 A1 | 6/2010 | Weisbart |
| 2011/0269665 A1* | 11/2011 | Kole ..................... C12N 15/87 514/1.1 |
| 2014/0178377 A1 | 6/2014 | Armstrong |

FOREIGN PATENT DOCUMENTS

| | | |
|---|---|---|
| WO | WO-91/09953 A1 | 7/1991 |
| WO | WO-97/32602 A1 | 9/1997 |
| WO | WO-98/39352 A1 | 9/1998 |
| WO | WO-98/53804 A1 | 12/1998 |
| WO | WO-2008/091911 A2 | 7/2008 |
| WO | WO-2008/148063 A1 | 12/2008 |
| WO | WO-2010/044894 A1 | 4/2010 |
| WO | WO-2010/138769 A1 | 12/2010 |
| WO | WO-2010/148010 A1 | 12/2010 |
| WO | WO-2013/138662 A1 | 9/2013 |

OTHER PUBLICATIONS

Cooper, Thomas A., "A Reversal of Misfortune of Myotonic Dystrophy?," New England Journal of Medicine, vol. 355(17), pp. 1825-1827 (2006).

Dansithong et al., "MBNL1 is the Primary of Determinant of Focus Formation and Aberrant Insulin Receptor Splicing in DM1," The Journal of Biological Chemistry, vol. 280(7), pp. 5773-5780 (2005).

de Haro et al., "MBNL1 and CUGBP1 Modify Expended CUG-induced Toxicity in a Drosophila Model of Myotonic Dystrophy Type 1," Human Molecular Genetics, vol. 15(13): 2138-2145 (2006).

Derossi et al., "The Third Helix of the Antennapedia Homeodomain Translocates through Biological Membranes," The Journal of Biological Chemistry, vol. 269(14), pp. 10444-10450 (1994).

Ellman, George L., "A Colorimetric Method for Determining Low Concentrations of Mercaptans," Archives of Biochemistry and Biophysics, vol. 74: 443-450 (1958).

Fardaei et al., "Three proteins, MBNL, MBLL and MBXL, co-localize in vivo with nuclear foci of expanded-repeat transcripts in DM1 and DM2 cells," Human Molecular Genetics, vol. 11(7), pp. 805-814 (2002).

Goers et al., "MBNL1 binds GC motifs embedded in pyrimidines to regulate alternative splicing," Nucleic Acids Research, vol. 38(7): 2467-2484 (2010).

Hansen et al., "Antibody-Mediated Transduction of Therapeutic Proteins Into Living Cells," TheScientificWorld Journal, vol. 5: 782-788 (2005).

Hansen et al., "Intranuclear Protein Transduction through a Nucleoside Salvage Pathway," Journal of Biological Chemistry, vol. 282(29), pp. 20790-20793 (2007).

Hansen, J. E., et al., "Antibody-Mediated Hsp70 Protein Therapy," Brain Research, 1088:187-196 (2006).

Hao, et al., "Muscleblind-like 2 (Mbnl2)—Deficient Mice as a Model for Myotonic Dystrophy," Developmental Dynamics, vol. 237(2), pp. 403-410 (2008).

Ho et al., "Colocalization of muscleblind with RNA foci is separable from mis-regulation of alternative splicing in myotonic dystrophy," Journal of Cell Science, vol. 118(13), pp. 2923-2933 (2005).

Holt et al., "Muscleblind-Like Proteins: Similarities and Differences in Normal and Myotonic Dystrophy Muscle," American Journal of Pathology, vol. 174(1), pp. 216-227 (2009).

Kanadia et al., "A Muscleblind Knockout Model for Myotonic Dystrophy," Science, vol. 302(5652), pp. 1978-1980 (2003).

Kanadia et al., "Reversal of RNA missplicing and myotonia after muscleblind overexpression in a mouse poly(CUG) model for myotonic dystrophy," Proceedings of the National Academy of Sciences USA, vol. 103(31), pp. 11748-11753 (2006).

Kino et al., "Muscleblind protein, MBNL1/EXP, binds specifically to CHHG repeats," Human Molecular Genetics, vol. 13(5), pp. 495-507 (2004).

(56) References Cited

OTHER PUBLICATIONS

Korade-Mirnics, et al., "Myotonic dystrophy: molecular windows on a complex etiology," Nucleic Acids Research, vol. 26(6), pp. 1363-1368 (1998).
Lee et al., "RNase H-mediated degradation of toxic RNA in myotonic dystrophy type 1," PNAS, vol. 109(11): 4221-4226 (2012).
Lin et al., "Failure of MBLN1-dependent post-natal splicing transitions in myotonic dystrophy," Human Molecular Genetics, vol. 15(13), pp. 2087-2097 (2006).
Liquori et al., "Myotonic Dystrophy Type 2 Caused by a CCTG Expansion in Intron 1 of ZNF9," Science, vol. 293, pp. 864-867 (2001).
Mahadevan et al., "Myotonic Dystrophy Mutation: An Unstable CTG Repeat in the 3' Untranslated Region of the Gene," Science, vol. 255(5049): 1253-1255 (1992).
Mankodi et al., "Myotonic Dystrophy in Transgenic Mice Expressing an Expanded CUG Repeat," Science, vol. 289, pp. 1769-1773 (2000).
Mankodi et al., "Nuclear RNA Foci in the Heart in Myotonic Dystrophy," Circulation Research, vol. 97(11), pp. 1152-1155 (2005).
Mankodi, A., et al., "Expanded CUG Repeats Trigger Aberrant Splicing of ClC-1 Chloride Channel Pre-mRNA and Hyperexcitability of Skeletal Muscle in Myotonic Dystrophy," Molecular Cell, 10:35-44 (2002).
Means et al., "Chemical modifications of proteins: history and applications," Bioconjugate Chemistry, vol. 1(1): 2-12 (1990).
Miller et al., "Recruitment of human muscleblind proteins to $(CUG)_n$ expansions associated with myotonic dystrophy," The EMBO Journal, vol. 19(17), pp. 4439-4448 (2000).
Mulders, et al., "Triplet-repeat oligonucleotide-mediated reversal of RNA toxicity in myotonic dystrophy," PNAS, vol. 106(33): 13915-13920 (2009).
NCBI GenBank Accession No. NM_018388 dated Feb. 15, 2009.
NCBI GenBank Accession No. NM_018388 dated Jul. 4, 2000.
NCBI GenBank Accession No. NM_021038 dated Dec. 27, 2009.
NCBI GenBank Accession No. NM_021038 dated Oct. 3, 2000.
NCBI GenBank Accession No. NM_133486 dated Feb. 15, 2009.
NCBI GenBank Accession No. NM_133486 dated May 2, 2003.
NCBI GenBank Accession No. NM_144778 dated Aug. 16, 2009.
NCBI GenBank Accession No. NM_144778 dated Jun. 18, 2002.
NCBI GenBank Accession No. NM_207292 dated Apr. 20, 2004.
NCBI GenBank Accession No. NM_207292 dated Jan. 31, 2010.
NCBI GenBank Accession No. NM_207293 dated Apr. 20, 2004.
NCBI GenBank Accession No. NM_207293 dated Dec. 27, 2009.
NCBI GenBank Accession No. NM_207294 dated Apr. 20, 2004.
NCBI GenBank Accession No. NM_207294 dated Jan. 31, 2010.
NCBI GenBank Accession No. NM_207295 dated Apr. 20, 2004.
NCBI GenBank Accession No. NM_207295 dated Dec. 27, 2009.
NCBI GenBank Accession No. NM_207296 dated Apr. 20, 2004.
NCBI GenBank Accession No. NM_207296 dated Jan. 31, 2010.
NCBI GenBank Accession No. NM_207297 dated Apr. 20, 2004.
NCBI GenBank Accession No. NM_207297 dated Dec. 27, 2009.
NCBI GenBank Accession No. NM_207304 dated Apr. 20, 2004.
NCBI GenBank Accession No. NM_207304 dated Jan. 31, 2010.
Nielsen et al., "Sequence-Selective Recognition of DNA by Strand Displacement with a Thymine-Substituted Polyamide," Science, vol. 254: 1497-1500 (1991).
O'Donnell et al., "A Decade of Molecular Studies of Fragile X Syndrome," Annu. Rev. Neurosci., vol. 25, pp. 315-338 (2002).
Orengo et al., "Expanded CTG repeats within the DMPK 3' UTR causes severe skeletal muscle wasting in an inducible mouse model for myotonic dystrophy," PNAS, vol. 105(7), pp. 2646-2651 (2008).
Osborne et al., "Transcriptional and post-transcriptional impact of toxic RNA in myotonic dystrophy," Human Molecular Genetics, vol. 18(8), pp. 1471-1481 (2009).

Partis et al., "Cross-Linking of Protein by w-Maleimido Alkanoyl N-Hydroxysuccinimido Esters," Journal of Protein Chemistry, vol. 2(3):263-277 (1983).
Pascual et al., "The Muscleblind family of proteins: an emerging class of regulators of developmentally programmed alternative splicing," Differentiation, vol. 74(2-3), pp. 65-80 (2006).
Pennycooke, M., et al., "Differential Expression of Human Nucleoside Transporters in Normal and Tumor Tissue," Biochemical and Biophysical Research Communications, 280:951-959 (2001).
Ranum et al., "Dominantly inherited, non-coding microsatellite expansion disorders," Current Opinion in Genetics & Development, vol. 12, pp. 266-271 (2002).
Riddles et al., "Ellman's Reagent: 5,5' -Dithiobis(2-nitrobenzoic Acid)—a Reexamination, Analytical Biochemistry, vol. 94: 75-81 (1979).
Saleem et al., "Association of CAG repeat loci on chromosome 22 with schizophrenia and bipolar disorder," Molecular Psychiatry, vol. 6(6), pp. 694-700 (2001).
Traunecker et al., "Highly efficient neutralization of HIV with recombinant CD4-immunoglobulin molecules," Nature, vol. 339: 68-70 (1989).
Tsilfidis et al., "Correlation between CTG trinucleotide repeat length and frequency of severe congenital myotonic dystrophy," Nature Genetics, vol. 1(3): 192-195 (1992).
Vicente et al., "Muscleblind isoforms are functionally distinct and regulate α-actinin splicing," Differentiation, vol. 75(5), pp. 427-440 (2007).
von Pierre Martin, "Ein neuer Zugang zu 2' -O-Alkylribonucleosiden und Eigenschaften deren Oligonucleotide," Helvetica Chimica Acta, vol. 78: 486-504 (1995) (English abstract).
Warf et al., "MBNL binds similar RNA structures in the CUG repeats of myotonic dystrophy and its pre-mRNA substrate cardiac troponin T," RNA, vol. 13, pp. 2238-2251 (2007).
Weisbart et al., "A Conserved Anti-DNA Antibody Idiotype associated with nephritis in Murine and Human Systemic Lupus Erythematosus," Journal of Immunology, vol. 144(7), pp. 2653-2658 (1990).
Weisbart, R., et al., "An Autoantibody is Modified for Use as a Delivery System to Target the Cell Nucleus: Therapeutic Implications," Journal of Autoimmunity, 11:539-546 (1998).
Weisbart, R., et al., "An Intracellular Delivery Vehicle for Protein Transduction of Micro-Dystrophin," Journal of Drug Targeting, 13(2):81-87 (2005).
Weisbart, R., et al., "Cell Type Specific Targeted Intracellular Delivery Into Muscle of a Monoclonal Antibody that Binds Myosin IIb," Molecular Immunology, 39:783-789 (2003).
Weisbart, R., et al., Novel Protein Transfection fo Primary Rat Cortical Neurons Using an Antibody that Penetrate Living Cells, Journal of Immunology, 164(11):6020-2026 (2000).
Weisbart, R., et al., "Nuclear Delivery of p53 C-terminal Peptides into Cancer Cells Using scFv Fragments of a Monoclonal Antibody that Penetrates Living Cells," Cancer Letters, 195:211-219 (2003).
Wheeler et al., "Reversal of RNA dominance by displacement of protein sequestered on triplet repeat RNA," Science, vol. 325, pp. 336-339 (2009).
Written Opinion of the International Searching Authority (PCT/US2009/005716) dated Dec. 9, 2009.
Yuan et al., "Muscleblind-like 1 interacts with RNA hairpins in splicing target and pathogenic RNAs," Nucleic Acids Research, vol. 35(16), pp. 5474-5486 (2007).
Zack et al., "Mechanisms of Cellular Penetration and Nuclear Localization of an Anti-Double Strand DNA Autoantibody," Journal of Immunology, 157(5):2082-2088 (1996).

* cited by examiner

SEQUENCE LISTING

```
<160> NUMBER OF SEQ ID NOS: 27

<210> SEQ ID NO 1
<211> LENGTH: 382
<212> TYPE: PRT
<213> ORGANISM: Homo sapiens

<400> SEQUENCE: 1

Met Ala Val Ser Val Thr Pro Ile Arg Asp Thr Lys Trp Leu Thr Leu
1               5                   10                  15

Glu Val Cys Arg Glu Phe Gln Arg Gly Thr Cys Ser Arg Pro Asp Thr
            20                  25                  30

Glu Cys Lys Phe Ala His Pro Ser Lys Ser Cys Gln Val Glu Asn Gly
        35                  40                  45

Arg Val Ile Ala Cys Phe Asp Ser Leu Lys Gly Arg Cys Ser Arg Glu
    50                  55                  60

Asn Cys Lys Tyr Leu His Pro Pro His Leu Lys Thr Gln Leu Glu
65                  70                  75                  80

Ile Asn Gly Arg Asn Asn Leu Ile Gln Gln Lys Asn Met Ala Met Leu
                85                  90                  95

Ala Gln Gln Met Gln Leu Ala Asn Ala Met Met Pro Gly Ala Pro Leu
            100                 105                 110

Gln Pro Val Pro Met Phe Ser Val Ala Pro Ser Leu Ala Thr Asn Ala
        115                 120                 125

Ser Ala Ala Phe Asn Pro Tyr Leu Gly Pro Val Ser Pro Ser Leu
    130                 135                 140

Val Pro Ala Glu Ile Leu Pro Thr Ala Pro Met Leu Val Thr Gly Asn
145                 150                 155                 160

Pro Gly Val Pro Val Pro Ala Ala Ala Ala Ala Ala Gln Lys Leu
                165                 170                 175

Met Arg Thr Asp Arg Leu Glu Val Cys Arg Glu Tyr Gln Arg Gly Asn
            180                 185                 190

Cys Asn Arg Gly Glu Asn Asp Cys Arg Phe Ala His Pro Ala Asp Ser
        195                 200                 205

Thr Met Ile Asp Thr Asn Asp Asn Thr Val Thr Val Cys Met Asp Tyr
    210                 215                 220

Ile Lys Gly Arg Cys Ser Arg Glu Lys Cys Lys Tyr Phe His Pro Pro
225                 230                 235                 240
```

```
Ala His Leu Gln Ala Lys Ile Lys Ala Gln Tyr Gln Val Asn Gln
                245             250             255

Ala Ala Ala Ala Gln Ala Ala Thr Ala Ala Met Gly Ile Pro
            260             265             270

Gln Ala Val Leu Pro Leu Pro Lys Arg Pro Ala Leu Glu Lys Thr
        275             280             285

Asn Gly Ala Thr Ala Val Phe Asn Thr Gly Ile Phe Gln Tyr Gln Gln
        290             295             300

Ala Leu Ala Asn Met Gln Leu Gln Gln His Thr Ala Phe Leu Pro Pro
305             310             315             320

Gly Ser Ile Leu Cys Met Thr Pro Ala Thr Ser Val Val Pro Met Val
                325             330             335

His Gly Ala Thr Pro Ala Thr Val Ser Ala Ala Thr Thr Ser Ala Thr
                340             345             350

Ser Val Pro Phe Ala Ala Thr Ala Thr Ala Asn Gln Ile Pro Ile Ile
                355             360             365

Ser Ala Glu His Leu Thr Ser His Lys Tyr Val Thr Gln Met
        370             375             380

<210> SEQ ID NO 2
<211> LENGTH: 370
<212> TYPE: PRT
<213> ORGANISM: Homo sapiens

<400> SEQUENCE: 2

Met Ala Val Ser Val Thr Pro Ile Arg Asp Thr Lys Trp Leu Thr Leu
1               5                   10                  15

Glu Val Cys Arg Glu Phe Gln Arg Gly Thr Cys Ser Arg Pro Asp Thr
            20                  25                  30

Glu Cys Lys Phe Ala His Pro Ser Lys Ser Cys Gln Val Glu Asn Gly
        35                  40                  45

Arg Val Ile Ala Cys Phe Asp Ser Leu Lys Gly Arg Cys Ser Arg Glu
    50                  55                  60

Asn Cys Lys Tyr Leu His Pro Pro Pro His Leu Lys Thr Gln Leu Glu
65                  70                  75                  80

Ile Asn Gly Arg Asn Asn Leu Ile Gln Gln Lys Asn Met Ala Met Leu
                85                  90                  95

Ala Gln Gln Met Gln Leu Ala Asn Ala Met Met Pro Gly Ala Pro Leu
            100                 105                 110

Gln Pro Val Pro Met Phe Ser Val Ala Pro Ser Leu Ala Thr Asn Ala
        115                 120                 125

Ser Ala Ala Ala Phe Asn Pro Tyr Leu Gly Pro Val Ser Pro Ser Leu
    130                 135                 140

Val Pro Ala Glu Ile Leu Pro Thr Ala Pro Met Leu Val Thr Gly Asn
145                 150                 155                 160

Pro Gly Val Pro Val Pro Ala Ala Ala Ala Ala Gln Lys Leu
                165                 170                 175

Met Arg Thr Asp Arg Leu Glu Val Cys Arg Glu Tyr Gln Arg Gly Asn
            180                 185                 190

Cys Asn Arg Gly Glu Asn Asp Cys Arg Phe Ala His Pro Ala Asp Ser
        195                 200                 205

Thr Met Ile Asp Thr Asn Asp Asn Thr Val Thr Val Cys Met Asp Tyr
    210                 215                 220

Ile Lys Gly Arg Cys Ser Arg Glu Lys Cys Lys Tyr Phe His Pro Pro
```

```
                225                 230                 235                 240
Ala His Leu Gln Ala Lys Ile Lys Ala Ala Gln Tyr Gln Val Asn Gln
                    245                 250                 255

Ala Ala Ala Ala Gln Ala Ala Thr Ala Ala Met Gly Ile Pro
                260                 265                 270

Gln Ala Val Leu Pro Pro Leu Pro Lys Arg Pro Ala Leu Glu Lys Thr
                275                 280                 285

Asn Gly Ala Thr Ala Val Phe Asn Thr Gly Ile Phe Gln Tyr Gln Gln
                290                 295                 300

Ala Leu Ala Asn Met Gln Leu Gln Gln His Thr Ala Phe Leu Pro Pro
305                 310                 315                 320

Val Pro Met Val His Gly Ala Thr Pro Ala Thr Val Ser Ala Ala Thr
                    325                 330                 335

Thr Ser Ala Thr Ser Val Pro Phe Ala Ala Thr Ala Thr Ala Asn Gln
                340                 345                 350

Ile Pro Ile Ile Ser Ala Glu His Leu Thr Ser His Lys Tyr Val Thr
                    355                 360                 365

Gln Met
    370

<210> SEQ ID NO 3
<211> LENGTH: 388
<212> TYPE: PRT
<213> ORGANISM: Homo sapiens

<400> SEQUENCE: 3

Met Ala Val Ser Val Thr Pro Ile Arg Asp Thr Lys Trp Leu Thr Leu
1               5                   10                  15

Glu Val Cys Arg Glu Phe Gln Arg Gly Thr Cys Ser Arg Pro Asp Thr
                20                  25                  30

Glu Cys Lys Phe Ala His Pro Ser Lys Ser Cys Gln Val Glu Asn Gly
                35                  40                  45

Arg Val Ile Ala Cys Phe Asp Ser Leu Lys Gly Arg Cys Ser Arg Glu
            50                  55                  60

Asn Cys Lys Tyr Leu His Pro Pro His Leu Lys Thr Gln Leu Glu
65                  70                  75                  80

Ile Asn Gly Arg Asn Asn Leu Ile Gln Gln Lys Asn Met Ala Met Leu
                85                  90                  95

Ala Gln Gln Met Gln Leu Ala Asn Ala Met Met Pro Gly Ala Pro Leu
                100                 105                 110

Gln Pro Val Pro Met Phe Ser Val Ala Pro Ser Leu Ala Thr Asn Ala
                115                 120                 125

Ser Ala Ala Ala Phe Asn Pro Tyr Leu Gly Pro Val Ser Pro Ser Leu
            130                 135                 140

Val Pro Ala Glu Ile Leu Pro Thr Ala Pro Met Leu Val Thr Gly Asn
145                 150                 155                 160

Pro Gly Val Pro Val Pro Ala Ala Ala Ala Ala Gln Lys Leu
                165                 170                 175

Met Arg Thr Asp Arg Leu Glu Val Cys Arg Glu Tyr Gln Arg Gly Asn
                180                 185                 190

Cys Asn Arg Gly Glu Asn Asp Cys Arg Phe Ala His Pro Ala Asp Ser
            195                 200                 205

Thr Met Ile Asp Thr Asn Asp Asn Thr Val Thr Val Cys Met Asp Tyr
                210                 215                 220
```

```
Ile Lys Gly Arg Cys Ser Arg Glu Lys Cys Lys Tyr Phe His Pro Pro
225                 230                 235                 240

Ala His Leu Gln Ala Lys Ile Lys Ala Ala Gln Tyr Gln Val Asn Gln
            245                 250                 255

Ala Ala Ala Ala Gln Ala Ala Thr Ala Ala Ala Met Thr Gln Ser
        260                 265                 270         Ser

Ala Val Lys Ser Leu Lys Arg Pro Leu Glu Ala Thr Phe Asp Leu Gly
            275                 280                 285

Ile Pro Gln Ala Val Leu Pro Leu Pro Lys Arg Pro Ala Leu Glu
    290                 295                 300

Lys Thr Asn Gly Ala Thr Ala Val Phe Asn Thr Gly Ile Phe Gln Tyr
305                 310                 315                 320

Gln Gln Ala Leu Ala Asn Met Gln Leu Gln Gln His Thr Ala Phe Leu
                325                 330                 335

Pro Pro Val Pro Met Val His Gly Ala Thr Pro Ala Thr Val Ser Ala
            340                 345                 350

Ala Thr Thr Ser Ala Thr Ser Val Pro Phe Ala Ala Thr Ala Thr Ala
            355                 360                 365

Asn Gln Ile Pro Ile Ile Ser Ala Glu His Leu Thr Ser His Lys Tyr
370                 375                 380

Val Thr Gln Met
385

<210> SEQ ID NO 4
<211> LENGTH: 302
<212> TYPE: PRT
<213> ORGANISM: Homo sapiens

<400> SEQUENCE: 4

Met Ala Val Ser Val Thr Pro Ile Arg Asp Thr Lys Trp Leu Thr Leu
1               5                   10                  15

Glu Val Cys Arg Glu Phe Gln Arg Gly Thr Cys Ser Arg Pro Asp Thr
            20                  25                  30

Glu Cys Lys Phe Ala His Pro Ser Lys Ser Cys Gln Val Glu Asn Gly
        35                  40                  45

Arg Val Ile Ala Cys Phe Asp Ser Leu Lys Gly Arg Cys Ser Arg Glu
    50                  55                  60

Asn Cys Lys Tyr Leu His Pro Pro His Leu Lys Thr Gln Leu Glu
65                  70                  75                  80

Ile Asn Gly Arg Asn Asn Leu Ile Gln Gln Lys Asn Met Ala Met Leu
                85                  90                  95

Ala Gln Gln Met Gln Leu Ala Asn Ala Met Met Pro Gly Ala Pro Leu
            100                 105                 110

Gln Pro Val Val Cys Arg Glu Tyr Gln Arg Gly Asn Cys Asn Arg Gly
        115                 120                 125

Glu Asn Asp Cys Arg Phe Ala His Pro Ala Asp Ser Thr Met Ile Asp
    130                 135                 140

Thr Asn Asp Asn Thr Val Thr Val Cys Met Asp Tyr Ile Lys Gly Arg
145                 150                 155                 160

Cys Ser Arg Glu Lys Cys Lys Tyr Phe His Pro Pro Ala His Leu Gln
                165                 170                 175

Ala Lys Ile Lys Ala Ala Gln Tyr Gln Val Asn Gln Ala Ala Ala
            180                 185                 190

Gln Ala Ala Ala Thr Ala Ala Ala Met Gly Ile Pro Gln Ala Val Leu
        195                 200                 205
```

```
Pro Pro Leu Pro Lys Arg Pro Ala Leu Glu Lys Thr Asn Gly Ala Thr
        210                 215                 220

Ala Val Phe Asn Thr Gly Ile Phe Gln Tyr Gln Gln Ala Leu Ala Asn
225                 230                 235                 240

Met Gln Leu Gln Gln His Thr Ala Phe Leu Pro Pro Val Pro Met Val
                245                 250                 255

His Gly Ala Thr Pro Ala Thr Val Ser Ala Ala Thr Thr Ser Ala Thr
            260                 265                 270

Ser Val Pro Phe Ala Ala Thr Ala Thr Ala Asn Gln Ile Pro Ile Ile
        275                 280                 285

Ser Ala Glu His Leu Thr Ser His Lys Tyr Val Thr Gln Met
290                 295                 300

<210> SEQ ID NO 5
<211> LENGTH: 314
<212> TYPE: PRT
<213> ORGANISM: Homo sapiens

<400> SEQUENCE: 5

Met Ala Val Ser Val Thr Pro Ile Arg Asp Thr Lys Trp Leu Thr Leu
1               5                   10                  15

Glu Val Cys Arg Glu Phe Gln Arg Gly Thr Cys Ser Arg Pro Asp Thr
            20                  25                  30

Glu Cys Lys Phe Ala His Pro Ser Lys Ser Cys Gln Val Glu Asn Gly
        35                  40                  45

Arg Val Ile Ala Cys Phe Asp Ser Leu Lys Gly Arg Cys Ser Arg Glu
    50                  55                  60

Asn Cys Lys Tyr Leu His Pro Pro His Leu Lys Thr Gln Leu Glu
65                  70                  75                  80

Ile Asn Gly Arg Asn Asn Leu Ile Gln Gln Lys Asn Met Ala Met Leu
                85                  90                  95

Ala Gln Gln Met Gln Leu Ala Asn Ala Met Met Pro Gly Ala Pro Leu
            100                 105                 110

Gln Pro Val Val Cys Arg Glu Tyr Gln Arg Gly Asn Cys Asn Arg Gly
        115                 120                 125

Glu Asn Asp Cys Arg Phe Ala His Pro Ala Asp Ser Thr Met Ile Asp
    130                 135                 140

Thr Asn Asp Asn Thr Val Thr Val Cys Met Asp Tyr Ile Lys Gly Arg
145                 150                 155                 160

Cys Ser Arg Glu Lys Cys Lys Tyr Phe His Pro Pro Ala His Leu Gln
                165                 170                 175

Ala Lys Ile Lys Ala Ala Gln Tyr Gln Val Asn Gln Ala Ala Ala Ala
            180                 185                 190

Gln Ala Ala Ala Thr Ala Ala Ala Met Gly Ile Pro Gln Ala Val Leu
        195                 200                 205

Pro Pro Leu Pro Lys Arg Pro Ala Leu Glu Lys Thr Asn Gly Ala Thr
    210                 215                 220

Ala Val Phe Asn Thr Gly Ile Phe Gln Tyr Gln Gln Ala Leu Ala Asn
225                 230                 235                 240

Met Gln Leu Gln Gln His Thr Ala Phe Leu Pro Pro Gly Ser Ile Leu
                245                 250                 255

Cys Met Thr Pro Ala Thr Ser Val Val Pro Met Val His Gly Ala Thr
            260                 265                 270

Pro Ala Thr Val Ser Ala Ala Thr Thr Ser Ala Thr Ser Val Pro Phe
```

```
                275                 280                 285
Ala Ala Thr Ala Thr Ala Asn Gln Ile Pro Ile Ile Ser Ala Glu His
            290                 295                 300

Leu Thr Ser His Lys Tyr Val Thr Gln Met
305                 310

<210> SEQ ID NO 6
<211> LENGTH: 340
<212> TYPE: PRT
<213> ORGANISM: Homo sapiens

<400> SEQUENCE: 6

Met Ala Val Ser Val Thr Pro Ile Arg Asp Thr Lys Trp Leu Thr Leu
1               5                   10                  15

Glu Val Cys Arg Glu Phe Gln Arg Gly Thr Cys Ser Arg Pro Asp Thr
            20                  25                  30

Glu Cys Lys Phe Ala His Pro Ser Lys Ser Cys Gln Val Glu Asn Gly
        35                  40                  45

Arg Val Ile Ala Cys Phe Asp Ser Leu Lys Gly Arg Cys Ser Arg Glu
    50                  55                  60

Asn Cys Lys Tyr Leu His Pro Pro His Leu Lys Thr Gln Leu Glu
65                  70                  75                  80

Ile Asn Gly Arg Asn Asn Leu Ile Gln Gln Lys Asn Met Ala Met Leu
                85                  90                  95

Ala Gln Gln Met Gln Leu Ala Asn Ala Met Met Pro Gly Ala Pro Leu
            100                 105                 110

Gln Pro Val Pro Met Phe Ser Val Ala Pro Ser Leu Ala Thr Asn Ala
        115                 120                 125

Ser Ala Ala Ala Phe Asn Pro Tyr Leu Gly Pro Val Ser Pro Ser Leu
    130                 135                 140

Val Pro Ala Glu Ile Leu Pro Thr Ala Pro Met Leu Val Thr Gly Asn
145                 150                 155                 160

Pro Gly Val Pro Val Pro Ala Ala Ala Ala Ala Ala Gln Lys Leu
                165                 170                 175

Met Arg Thr Asp Arg Leu Glu Val Cys Arg Glu Tyr Gln Arg Gly Asn
            180                 185                 190

Cys Asn Arg Gly Glu Asn Asp Cys Arg Phe Ala His Pro Ala Asp Ser
        195                 200                 205

Thr Met Ile Asp Thr Asn Asp Asn Thr Val Thr Val Cys Met Asp Tyr
    210                 215                 220

Ile Lys Gly Arg Cys Ser Arg Glu Lys Cys Lys Tyr Phe His Pro Pro
225                 230                 235                 240

Ala His Leu Gln Ala Lys Ile Lys Ala Ala Gln Tyr Gln Val Asn Gln
                245                 250                 255

Ala Ala Ala Ala Gln Ala Ala Ala Thr Ala Ala Ala Met Phe Pro Trp
            260                 265                 270

Cys Thr Val Leu Arg Gln Pro Leu Cys Pro Gln Gln Gln His Leu Pro
        275                 280                 285

Gln Val Phe Pro Ser Leu Gln Gln Pro Gln Pro Thr Ser Pro Ile Leu
    290                 295                 300

Asp Ala Ser Thr Leu Leu Gly Ala Thr Ser Cys Pro Ala Ala Gly
305                 310                 315                 320

Lys Met Ile Pro Ile Ile Ser Ala Glu His Leu Thr Ser His Lys Tyr
                325                 330                 335
```

Val Thr Gln Met
            340

<210> SEQ ID NO 7
<211> LENGTH: 342
<212> TYPE: PRT
<213> ORGANISM: Homo sapiens

<400> SEQUENCE: 7

Met Ala Val Ser Val Thr Pro Ile Arg Asp Thr Lys Trp Leu Thr Leu
1               5                   10                  15

Glu Val Cys Arg Glu Phe Gln Arg Gly Thr Cys Ser Arg Pro Asp Thr
            20                  25                  30

Glu Cys Lys Phe Ala His Pro Ser Lys Ser Cys Gln Val Glu Asn Gly
        35                  40                  45

Arg Val Ile Ala Cys Phe Asp Ser Leu Lys Gly Arg Cys Ser Arg Glu
    50                  55                  60

Asn Cys Lys Tyr Leu His Pro Pro His Leu Lys Thr Gln Leu Glu
65                  70                  75                  80

Ile Asn Gly Arg Asn Asn Leu Ile Gln Gln Lys Asn Met Ala Met Leu
                85                  90                  95

Ala Gln Gln Met Gln Leu Ala Asn Ala Met Met Pro Gly Ala Pro Leu
            100                 105                 110

Gln Pro Val Pro Met Phe Ser Val Ala Pro Ser Leu Ala Thr Asn Ala
        115                 120                 125

Ser Ala Ala Ala Phe Asn Pro Tyr Leu Gly Pro Val Ser Pro Ser Leu
    130                 135                 140

Val Pro Ala Glu Ile Leu Pro Thr Ala Pro Met Leu Val Thr Gly Asn
145                 150                 155                 160

Pro Gly Val Pro Val Pro Ala Ala Ala Ala Ala Ala Gln Lys Leu
                165                 170                 175

Met Arg Thr Asp Arg Leu Glu Val Cys Arg Glu Tyr Gln Arg Gly Asn
            180                 185                 190

Cys Asn Arg Gly Glu Asn Asp Cys Arg Phe Ala His Pro Ala Asp Ser
        195                 200                 205

Thr Met Ile Asp Thr Asn Asp Asn Thr Val Thr Val Cys Met Asp Tyr
    210                 215                 220

Ile Lys Gly Arg Cys Ser Arg Glu Lys Cys Lys Tyr Phe His Pro Pro
225                 230                 235                 240

Ala His Leu Gln Ala Lys Ile Lys Ala Ala Gln Tyr Gln Val Asn Gln
                245                 250                 255

Ala Ala Ala Ala Gln Ala Ala Thr Ala Ala Ala Met Gly Ile Pro
            260                 265                 270

Gln Ala Val Leu Pro Pro Leu Pro Lys Arg Pro Ala Leu Glu Lys Thr
        275                 280                 285

Asn Gly Ala Thr Ala Val Phe Asn Thr Gly Ile Phe Gln Tyr Gln Gln
    290                 295                 300

Ala Leu Ala Asn Met Gln Leu Gln Gln His Thr Ala Phe Leu Pro Pro
305                 310                 315                 320

Gly Ser Ile Leu Cys Met Thr Pro Ala Thr Ser Val Asp Thr His Asn
                325                 330                 335

Ile Cys Arg Thr Ser Asp
            340

<210> SEQ ID NO 8

```
<211> LENGTH: 629
<212> TYPE: PRT
<213> ORGANISM: Homo sapiens

<400> SEQUENCE: 8

Met Ser Ala Glu Val Arg Leu Arg Arg Leu Gln Gln Leu Val Leu Asp
1               5                   10                  15

Pro Gly Phe Leu Gly Leu Glu Pro Leu Leu Asp Leu Leu Leu Gly Val
            20                  25                  30

His Gln Glu Leu Gly Ala Ser Glu Leu Ala Gln Asp Lys Tyr Val Ala
        35                  40                  45

Asp Phe Leu Gln Trp Ala Glu Pro Ile Val Val Arg Leu Lys Glu Val
    50                  55                  60

Arg Leu Gln Arg Asp Asp Phe Glu Ile Leu Lys Val Ile Gly Arg Gly
65                  70                  75                  80

Ala Phe Ser Glu Val Ala Val Val Lys Met Lys Gln Thr Gly Gln Val
                85                  90                  95

Tyr Ala Met Lys Ile Met Asn Lys Trp Asp Met Leu Lys Arg Gly Glu
            100                 105                 110

Val Ser Cys Phe Arg Glu Glu Arg Asp Val Leu Val Asn Gly Asp Arg
        115                 120                 125

Arg Trp Ile Thr Gln Leu His Phe Ala Phe Gln Asp Glu Asn Tyr Leu
    130                 135                 140

Tyr Leu Val Met Glu Tyr Tyr Val Gly Gly Asp Leu Leu Thr Leu Leu
145                 150                 155                 160

Ser Lys Phe Gly Glu Arg Ile Pro Ala Glu Met Ala Arg Phe Tyr Leu
                165                 170                 175

Ala Glu Ile Val Met Ala Ile Asp Ser Val His Arg Leu Gly Tyr Val
            180                 185                 190

His Arg Asp Ile Lys Pro Asp Asn Ile Leu Leu Asp Arg Cys Gly His
        195                 200                 205

Ile Arg Leu Ala Asp Phe Gly Ser Cys Leu Lys Leu Arg Ala Asp Gly
    210                 215                 220

Thr Val Arg Ser Leu Val Ala Val Gly Thr Pro Asp Tyr Leu Ser Pro
225                 230                 235                 240

Glu Ile Leu Gln Ala Val Gly Gly Gly Pro Gly Thr Gly Ser Tyr Gly
                245                 250                 255

Pro Glu Cys Asp Trp Trp Ala Leu Gly Val Phe Ala Tyr Glu Met Phe
            260                 265                 270

Tyr Gly Gln Thr Pro Phe Tyr Ala Asp Ser Thr Ala Glu Thr Tyr Gly
        275                 280                 285

Lys Ile Val His Tyr Lys Glu His Leu Ser Leu Pro Leu Val Asp Glu
    290                 295                 300

Gly Val Pro Glu Glu Ala Arg Asp Phe Ile Gln Arg Leu Leu Cys Pro
305                 310                 315                 320

Pro Glu Thr Arg Leu Gly Arg Gly Gly Ala Gly Asp Phe Arg Thr His
                325                 330                 335

Pro Phe Phe Phe Gly Leu Asp Trp Asp Gly Leu Arg Asp Ser Val Pro
            340                 345                 350

Pro Phe Thr Pro Asp Phe Glu Gly Ala Thr Asp Thr Cys Asn Phe Asp
        355                 360                 365

Leu Val Glu Asp Gly Leu Thr Ala Met Val Ser Gly Gly Gly Glu Thr
    370                 375                 380

Leu Ser Asp Ile Arg Glu Gly Ala Pro Leu Gly Val His Leu Pro Phe
```

Val Gly Tyr Ser Tyr Ser Cys Met Ala Leu Arg Asp Ser Glu Val Pro
              405                 410                 415

Gly Pro Thr Pro Met Glu Leu Glu Ala Glu Gln Leu Leu Glu Pro His
              420                 425                 430

Val Gln Ala Pro Ser Leu Glu Pro Ser Val Ser Pro Gln Asp Glu Thr
              435                 440                 445

Ala Glu Val Ala Val Pro Ala Ala Val Pro Ala Ala Glu Ala Glu Ala
450                 455                 460

Glu Val Thr Leu Arg Glu Leu Gln Glu Ala Leu Glu Glu Glu Val Leu
465                 470                 475                 480

Thr Arg Gln Ser Leu Ser Arg Glu Met Glu Ala Ile Arg Thr Asp Asn
                485                 490                 495

Gln Asn Phe Ala Ser Gln Leu Arg Glu Ala Glu Ala Arg Asn Arg Asp
            500                 505                 510

Leu Glu Ala His Val Arg Gln Leu Gln Glu Arg Met Glu Leu Leu Gln
        515                 520                 525

Ala Glu Gly Ala Thr Ala Val Thr Gly Val Pro Ser Pro Arg Ala Thr
530                 535                 540

Asp Pro Pro Ser His Leu Asp Gly Pro Pro Ala Val Ala Val Gly Gln
545                 550                 555                 560

Cys Pro Leu Val Gly Pro Gly Pro Met His Arg His Leu Leu Leu
                565                 570                 575

Pro Ala Arg Val Pro Arg Pro Gly Leu Ser Glu Ala Leu Ser Leu Leu
            580                 585                 590

Leu Phe Ala Val Val Leu Ser Arg Ala Ala Ala Leu Gly Cys Ile Gly
        595                 600                 605

Leu Val Ala His Ala Gly Gln Leu Thr Ala Val Trp Arg Arg Pro Gly
    610                 615                 620

Ala Ala Arg Ala Pro
625

<210> SEQ ID NO 9
<211> LENGTH: 14
<212> TYPE: DNA
<213> ORGANISM: Artificial Sequence
<220> FEATURE:
<223> OTHER INFORMATION: Description of Artificial Sequence: Synthetic
      oligonucleotide
<220> FEATURE:
<221> NAME/KEY: modified_base
<222> LOCATION: (1)..(3)
<223> OTHER INFORMATION: LNA nucleotides
<220> FEATURE:
<221> NAME/KEY: modified_base
<222> LOCATION: (4)..(11)
<223> OTHER INFORMATION: Phosphorothioate nucleotides
<220> FEATURE:
<221> NAME/KEY: modified_base
<222> LOCATION: (12)..(14)
<223> OTHER INFORMATION: LNA nucleotides

<400> SEQUENCE: 9
agcagcagca gcag                                                     14

<210> SEQ ID NO 10
<211> LENGTH: 16
<212> TYPE: DNA
<213> ORGANISM: Artificial Sequence
<220> FEATURE:
<223> OTHER INFORMATION: Description of Artificial Sequence: Synthetic

```
                oligonucleotide
<220> FEATURE:
<221> NAME/KEY: modified_base
<222> LOCATION: (1)..(3)
<223> OTHER INFORMATION: LNA nucleotides
<220> FEATURE:
<221> NAME/KEY: modified_base
<222> LOCATION: (4)..(13)
<223> OTHER INFORMATION: Phosphorothioate nucleotides
<220> FEATURE:
<221> NAME/KEY: modified_base
<222> LOCATION: (14)..(16)
<223> OTHER INFORMATION: LNA nucleotides

<400> SEQUENCE: 10
cagcagcagc agcagc                                                         16

<210> SEQ ID NO 11
<211> LENGTH: 14
<212> TYPE: DNA
<213> ORGANISM: Artificial Sequence
<220> FEATURE:
<223> OTHER INFORMATION: Description of Artificial Sequence: Synthetic
      oligonucleotide
<220> FEATURE:
<221> NAME/KEY: modified_base
<222> LOCATION: (1)..(3)
<223> OTHER INFORMATION: 2'-O-methoxyethyl nucleotides
<220> FEATURE:
<221> NAME/KEY: modified_base
<222> LOCATION: (4)..(11)
<223> OTHER INFORMATION: Phosphorothioate nucleotides
<220> FEATURE:
<221> NAME/KEY: modified_base
<222> LOCATION: (12)..(14)
<223> OTHER INFORMATION: 2'-O-methoxyethyl nucleotides

<400> SEQUENCE: 11
agcagcagca gcag                                                           14

<210> SEQ ID NO 12
<211> LENGTH: 14
<212> TYPE: DNA
<213> ORGANISM: Artificial Sequence
<220> FEATURE:
<223> OTHER INFORMATION: Description of Artificial Sequence: Synthetic
      oligonucleotide
<220> FEATURE:
<221> NAME/KEY: modified_base
<222> LOCATION: (1)..(2)
<223> OTHER INFORMATION: 2'-O-methoxyethyl nucleotides
<220> FEATURE:
<221> NAME/KEY: modified_base
<222> LOCATION: (3)..(5)
<223> OTHER INFORMATION: Phosphorothioate nucleotides
<220> FEATURE:
<221> NAME/KEY: modified_base
<222> LOCATION: (6)..(7)
<223> OTHER INFORMATION: 2'-O-methoxyethyl nucleotides
<220> FEATURE:
<221> NAME/KEY: modified_base
<222> LOCATION: (8)..(8)
<223> OTHER INFORMATION: Phosphorothioate nucleotide
<220> FEATURE:
<221> NAME/KEY: modified_base
<222> LOCATION: (9)..(10)
<223> OTHER INFORMATION: 2'-O-methoxyethyl nucleotides
<220> FEATURE:
<221> NAME/KEY: modified_base
<222> LOCATION: (11)..(11)
<223> OTHER INFORMATION: Phosphorothioate nucleotide
<220> FEATURE:
<221> NAME/KEY: modified_base
<222> LOCATION: (12)..(14)
<223> OTHER INFORMATION: 2'-O-methoxyethyl nucleotides
```

-continued

<400> SEQUENCE: 12
agcagcagca gcag                                                       14

<210> SEQ ID NO 13
<211> LENGTH: 116
<212> TYPE: PRT
<213> ORGANISM: Homo sapiens

<400> SEQUENCE: 13

Glu Val Gln Leu Val Glu Ser Gly Gly Gly Leu Val Lys Pro Gly Gly
1               5                   10                  15

Ser Arg Lys Leu Ser Cys Ala Ala Ser Gly Phe Thr Phe Ser Asn Tyr
            20                  25                  30

Gly Met His Trp Val Arg Gln Ala Pro Glu Lys Gly Leu Glu Trp Val
        35                  40                  45

Ala Tyr Ile Ser Ser Gly Ser Ser Thr Ile Tyr Tyr Ala Asp Thr Val
    50                  55                  60

Lys Gly Arg Phe Thr Ile Ser Arg Asp Asn Ala Lys Asn Thr Leu Phe
65                  70                  75                  80

Leu Gln Met Thr Ser Leu Arg Ser Glu Asp Thr Ala Met Tyr Tyr Cys
                85                  90                  95

Ala Arg Arg Gly Leu Leu Leu Asp Tyr Trp Gly Gln Gly Thr Thr Leu
            100                 105                 110

Thr Val Ser Ser
        115

<210> SEQ ID NO 14
<211> LENGTH: 111
<212> TYPE: PRT
<213> ORGANISM: Homo sapiens

<400> SEQUENCE: 14

Asp Ile Val Leu Thr Gln Ser Pro Ala Ser Leu Ala Val Ser Leu Gly
1               5                   10                  15

Gln Arg Ala Thr Ile Ser Cys Arg Ala Ser Lys Ser Val Ser Thr Ser
            20                  25                  30

Ser Tyr Ser Tyr Met His Trp Tyr Gln Gln Lys Pro Gly Gln Pro Pro
        35                  40                  45

Lys Leu Leu Ile Lys Tyr Ala Ser Tyr Leu Glu Ser Gly Val Pro Ala
    50                  55                  60

Arg Phe Ser Gly Ser Gly Ser Gly Thr Asp Phe His Leu Asn Ile His
65                  70                  75                  80

Pro Val Glu Glu Glu Asp Ala Ala Thr Tyr Tyr Cys Gln His Ser Arg
                85                  90                  95

Glu Phe Pro Trp Thr Phe Gly Gly Gly Thr Lys Leu Glu Leu Lys
            100                 105                 110

<210> SEQ ID NO 15
<211> LENGTH: 15
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 15

Gly Gly Gly Gly Ser Gly Gly Gly Ser Gly Gly Gly Gly Ser
1               5                   10                  15

<210> SEQ ID NO 16
<211> LENGTH: 5
<212> TYPE: PRT
<213> ORGANISM: Homo sapiens

<400> SEQUENCE: 16

Asn Tyr Gly Met His
1               5

<210> SEQ ID NO 17
<211> LENGTH: 17
<212> TYPE: PRT
<213> ORGANISM: Homo sapiens

<400> SEQUENCE: 17

Tyr Ile Ser Ser Gly Ser Ser Thr Ile Tyr Tyr Ala Asp Thr Val Lys
1               5                   10                  15

Gly

<210> SEQ ID NO 18
<211> LENGTH: 7
<212> TYPE: PRT
<213> ORGANISM: Homo sapiens

<400> SEQUENCE: 18

Arg Gly Leu Leu Leu Asp Tyr
1               5

<210> SEQ ID NO 19
<211> LENGTH: 15
<212> TYPE: PRT
<213> ORGANISM: Homo sapiens

<400> SEQUENCE: 19

Arg Ala Ser Lys Ser Val Ser Thr Ser Ser Tyr Ser Tyr Met His
1               5                   10                  15

<210> SEQ ID NO 20
<211> LENGTH: 7
<212> TYPE: PRT
<213> ORGANISM: Homo sapiens

<400> SEQUENCE: 20

Tyr Ala Ser Tyr Leu Glu Ser
1               5

<210> SEQ ID NO 21
<211> LENGTH: 9
<212> TYPE: PRT
<213> ORGANISM: Homo sapiens

<400> SEQUENCE: 21

Gln His Ser Arg Glu Phe Pro Trp Thr
1               5

<210> SEQ ID NO 22
<211> LENGTH: 25
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 22
agcagcagca gcagcagcag cagca　　　　　　　　　　　　　　　　　　　25

<210> SEQ ID NO 23
<211> LENGTH: 21
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 23
cagcagcagc agcagcagca g　　　　　　　　　　　　　　　　　　　　21

<210> SEQ ID NO 24
<211> LENGTH: 3261
<212> TYPE: DNA
<213> ORGANISM: Homo sapiens

<400> SEQUENCE: 24

| | |
|---|---|
| gccacaagcc tccaccccag ctggtccccc acccaggctg cccagtttaa cattcctagt | 60 |
| cataggacct tgacttctga gaggcctgat tgtcatctgt aaataagggg taggactaaa | 120 |
| gcactcctcc tggaggactg agagatgggc tggaccggag cacttgagtc tgggatatgt | 180 |
| gaccatgcta cctttgtctc cctgtcctgt tccttccccc agccccaaat ccagggtttt | 240 |
| ccaaagtgtg gttcaagaac cacctgcatc tgaatctaga ggtactggat acaaccccac | 300 |
| gtctgggccg ttacccagga cattctacat gagaacgtgg gggtggggcc ctggctgcac | 360 |
| ctgaactgtc acctggagtc agggtggaag gtggaagaac tgggtcttat ttccttctcc | 420 |
| ccttgttctt tagggtctgt ccttctgcag actccgttac cccaccctaa ccatcctgca | 480 |
| cacccttgga gccctctggg ccaatgccct gtcccgcaaa gggcttctca ggcatctcac | 540 |
| ctctatggga gggcattttt ggcccccaga accttacacg tgtttatgt ggggaagccc | 600 |
| ctgggaagca gacagtccta gggtgaagct gagaggcaga gagaagggga gacagacaga | 660 |
| gggtggggct ttcccccttg tctccagtgc cctttctggt gaccctcggt tcttttcccc | 720 |
| caccaccccc ccagcggagc ccatcgtggt gaggcttaag gaggtccgac tgcagaggga | 780 |
| cgacttcgag attctgaagg tgatcggacg cggggcgttc agcgaggtag cggtagtgaa | 840 |
| gatgaagcag acgggccagg tgtatgccat gaagatcatg aacaagtggg acatgctgaa | 900 |
| gaggggcgag gtgtcgtgct tccgtgagga gagggacgtg ttggtgaatg ggaccggcg | 960 |
| gtggatcacg cagctgcact cgccttcca ggatgagaac tacctgtacc tggtcatgga | 1020 |
| gtattacgtg ggcggggacc tgctgacact gctgagcaag tttggggagc ggattccggc | 1080 |
| cgagatggcg cgcttctacc tggcggagat tgtcatggcc atagactcgg tgcaccggct | 1140 |
| tggctacgtg cacagggaca tcaaacccga caacatcctg ctggaccgct gtggccacat | 1200 |
| ccgcctggcc gacttcggct cttgcctcaa gctgcgggca gatggaacgg tgcggtcgct | 1260 |
| ggtggctgtg ggcacccag actacctgtc ccccgagatc ctgcaggctg tgggcggtgg | 1320 |
| gcctgggaca ggcagctacg ggcccgagtg tgactggtgg gcgctgggtg tattcgccta | 1380 |
| tgaaatgttc tatgggcaga cgcccttcta cgcggattcc acggcggaga cctatggcaa | 1440 |
| gatcgtccac tacaaggagc acctctctct gccgctggtg gacgaagggg tccctgagga | 1500 |
| ggctcgagac ttcattcagc ggttgctgtg tccccggag acacggctgg gccggggtgg | 1560 |
| agcaggcgac ttccggacac atcccttctt ctttggcctc gactgggatg gtctccggga | 1620 |
| cagcgtgccc cccttttacac cggatttcga aggtgccacc gacacatgca acttcgactt | 1680 |

```
ggtggaggac gggctcactg ccatggtgag cggggggcggg gagacactgt cggacattcg    1740
ggaaggtgcg ccgctagggg tccacctgcc ttttgtgggc tactcctact cctgcatggc    1800
cctcagggac agtgaggtcc caggcccac acccatggaa ctggaggccg agcagctgct    1860
tgagccacac gtgcaagcgc ccagcctgga gccctcggtg tccccacagg atgaaacagc    1920
tgaagtggca gttccagcgg ctgtccctgc ggcagaggct gaggccgagg tgacgctgcg    1980
ggagctccag gaagccctgg aggaggaggt gctcacccgg cagagcctga gccgggagat    2040
ggaggccatc cgcacggaca accagaactt cgccagtcaa ctacgcgagg cagaggctcg    2100
gaaccgggac ctagaggcac acgtccggca gttgcaggag cggatggagt tgctgcaggc    2160
agagggagcc acagctgtca cgggggtccc cagtccccgg ccacggatcc accttccca    2220
tctagatggc cccccggccg tggctgtggg ccagtgcccg ctggtggggc caggccccat    2280
gcaccgccgc cacctgctgc tccctgccag ggtccctagg cctggcctat cggaggcgct    2340
ttccctgctc ctgttcgccg ttgttctgtc tcgtgccgcc gccctgggct gcattgggtt    2400
ggtggcccac gccggccaac tcaccgcagt ctggcgccgc ccaggagccg cccgcgctcc    2460
ctgaacccta gaactgtctt cgactccggg gccccgttgg aagactgagt gcccggggca    2520
cggcacagaa gccgcgccca ccgcctgcca gttcacaacc gctccgagcg tgggtctccg    2580
cccagctcca gtcctgtgat ccgggcccgc cccctagcgg ccggggaggg aggggccggg    2640
tccgcggccg gcgaacgggg ctcgaagggt ccttgtagcc gggaatgctg ctgctgctgc    2700
tgctgctgct gctgctgctg ctgctgctgc tgctgctgct gctgctgggg ggatcacaga    2760
ccatttcttt ctttcggcca ggctgaggcc ctgacgtgga tgggcaaact gcaggcctgg    2820
gaaggcagca agccgggccg tccgtgttcc atcctccacg cacccccacc tatcgttggt    2880
tcgcaaagtg caaagctttc ttgtgcatga cgccctgctc tggggagcgt ctggcgcgat    2940
ctctgcctgc ttactcggga aatttgcttt tgccaaaccc gctttttcgg ggatcccgcg    3000
ccccctcct cacttgcgct gctctcggag ccccagccgg ctccgccgc ttcggcggtt    3060
tggatattta ttgacctcgt cctccgactc gctgacaggc tacaggaccc ccaacaaccc    3120
caatccacgt tttggatgca ctgagacccc gacattcctc ggtatttatt gtctgtcccc    3180
acctaggacc cccaccccg accctcgcga ataaaaggcc ctccatctgc ccaaaaaaaa    3240
aaaaaaaaaa aaaaaaaaa a                                              3261

<210> SEQ ID NO 25
<211> LENGTH: 2892
<212> TYPE: DNA
<213> ORGANISM: Homo sapiens

<400> SEQUENCE: 25
aggggggctg gaccaagggg tggggagaag gggaggaggc ctcggccggc cgcagagaga      60
agtggccaga gaggcccagg ggacagccag ggacaggcag acatgcagcc agggctccag     120
ggcctggaca ggggctgcca ggccctgtga caggaggacc ccgagccccc ggcccgggga     180
ggggccatgg tgctgcctgt ccaacatgtc agccgaggtg cggctgaggc ggctccagca     240
gctggtgttg gacccgggct tcctgggggct ggagcccctg ctcgaccttc tcctgggcgt     300
ccaccaggag ctgggcgcct ccgaactggc ccaggacaag tacgtggccg acttcttgca     360
gtgggcggag cccatcgtgg tgaggcttaa ggaggtccga ctgcagaggg acgacttcga     420
gattctgaag gtgatcggac gcggggcgtt cagcgaggta gcggtagtga agatgaagca     480
```

-continued

```
gacgggccag gtgtatgcca tgaagatcat gaacaagtgg gacatgctga agaggggcga    540
ggtgtcgtgc ttccgtgagg agagggacgt gttggtgaat ggggaccggc ggtggatcac    600
gcagctgcac ttcgccttcc aggatgagaa ctacctgtac ctggtcatgg agtattacgt    660
gggcggggac ctgctgacac tgctgagcaa gtttggggag cggattccgg ccgagatggc    720
gcgcttctac ctggcggaga ttgtcatggc catagactcg gtgcaccggc ttggctacgt    780
gcacagggac atcaaacccg acaacatcct gctggaccgc tgtggccaca tccgcctggc    840
cgacttcggc tcttgcctca agctgcgggc agatggaacg gtgcggtcgc tggtggctgt    900 gggcaccccca gactacctgt cccccgagat cctgcaggct gtgggcggtg ggcctgggac    960
aggcagctac gggcccgagt gtgactggtg ggcgctgggt gtattcgcct atgaaatgtt   1020
ctatgggcag acgcccttct acgcggattc cacggcggag acctatggca agatcgtcca   1080
ctacaaggag cacctctctc tgccgctggt ggacgaaggg gtccctgagg aggctcgaga   1140
cttcattcag cggttgctgt gtccccccgga gacacggctg ggccggggtg gagcaggcga   1200
cttccggaca catcccttct tctttggcct cgactgggat ggtctccggg acagcgtgcc   1260
cccctttaca ccggatttcg aaggtgccac cgacacatgc aacttcgact tggtggagga   1320
cgggctcact gccatggtga gcgggggcgg ggagacactg tcggacattc gggaaggtgc   1380
gccgctaggg gtccacctgc cttttgtggg ctactcctac tcctgcatgg ccctcaggga   1440
cagtgaggtc ccaggcccca cacccatgga actggaggcc gagcagctgc ttgagccaca   1500
cgtgcaagcg cccagcctgg agccctcggt gtccccacag gatgaaacag ctgaagtggc   1560
agttccagcg gctgtccctg cggcagaggc tgaggccgag gtgacgctgc gggagctcca   1620
ggaagccctg gaggaggagg tgctcacccg gcagagcctg agccgggaga tggaggccat   1680
ccgcacggac aaccagaact tcgccagtca actacgcgag gcagaggctc ggaaccggga   1740
cctagaggca cacgtccggc agttgcagga gcggatggag ttgctgcagg cagagggagc   1800
cacagctgtc acgggggtcc ccagtccccg ggccacggat ccaccttccc atctagatgg   1860 cccccccggcc gtggctgtgg gccagtgccc gctggtgggg ccaggcccca tgcaccgccg   1920
ccacctgctg ctccctgcca gggtccctag gcctggccta tcggaggcgc tttccctgct   1980
cctgttcgcc gttgttctgt ctcgtgccgc cgccctgggc tgcattgggt tggtggccca   2040
cgccggccaa ctcaccgcag tctggcgccg cccaggagcc gccgcgctc cctgaaccct   2100 agaactgtct tcgactccgg ggccccgttg aaagactgag tgcccggggc acggcacaga   2160
agccgcgccc accgcctgcc agttcacaac cgctccgagc gtgggtctcc gcccagctcc   2220
agtcctgtga tccgggcccg ccccctagcg gccggggagg gaggggccgg gtccgcggcc   2280
ggcgaacggg gctcgaaggg tccttgtagc cgggaatgct gctgctgctg ctgctgctgc   2340
tgctgctgct gctgctgctg ctgctgctgc tgctgctggg gggatcacag accatttctt   2400
tctttcggcc aggctgaggc cctgacgtgg atgggcaaac tgcaggcctg ggaaggcagc   2460
aagccgggcc gtccgtgttc atcctccac gcaccccac ctatcgttgg ttcgcaaagt   2520
gcaaagcttt cttgtgcatg acgccctgct ctggggagcg tctggcgcga tctctgcctg   2580
cttactcggg aaatttgctt ttgccaaacc cgctttttcg gggatcccgc gccccctcc   2640 tcacttgcgc tgctctcgga gccccagccg gctccgcccg cttcggcggt ttggatattt   2700
attgacctcg tcctccgact cgctgacagg ctacaggacc cccaacaacc ccaatccacg   2760
ttttggatgc actgagaccc cgacattcct cggtatttat tgtctgtccc cacctaggac   2820
ccccaccccc gaccctcgcg aataaaaggc cctccatctg cccaaaaaaa aaaaaaaaaa   2880
```
aaaaaaaaaa aa 2892

<210> SEQ ID NO 26
<211> LENGTH: 2877
<212> TYPE: DNA
<213> ORGANISM: Homo sapiens

<400> SEQUENCE: 26

| | | | | | |
|---|---|---|---|---|---|
| aggggggctg | gaccaagggg | tggggagaag | gggaggaggc | ctcggccggc | cgcagagaga | 60 |
| agtggccaga | gaggcccagg | ggacagccag | ggacaggcag | acatgcagcc | agggctccag | 120 |
| ggcctggaca | ggggctgcca | ggccctgtga | caggaggacc | ccgagccccc | ggcccgggga | 180 |
| ggggccatgg | tgctgcctgt | ccaacatgtc | agccgaggtg | cggctgaggc | ggctccagca | 240 |
| gctggtgttg | gacccgggct | tcctggggct | ggagcccctg | ctcgaccttc | tcctgggcgt | 300 |
| ccaccaggag | ctgggcgcct | ccgaactggc | ccaggacaag | tacgtggccg | acttcttgca | 360 |
| gtgggcggaa | cccatcgtgg | tgaggcttaa | ggaggtccga | ctgcagaggg | acgacttcga | 420 |
| gattctgaag | gtgatcggac | gcggggcgtt | cagcgaggta | gcggtagtga | agatgaagca | 480 |
| gacgggccag | gtgtatgcca | tgaagatcat | gaacaagtgg | gacatgctga | agaggggcga | 540 |
| ggtgtcgtgc | ttccgtgagg | agagggacgt | gttggtgaat | ggggaccggc | ggtggatcac | 600 |
| gcagctgcac | ttcgccttcc | aggatgagaa | ctacctgtac | ctggtcatgg | agtattacgt | 660 |
| gggcggggac | ctgctgacac | tgctgagcaa | gtttgggag | cggattccgg | ccgagatggc | 720 |
| gcgcttctac | ctggcggaga | ttgtcatggc | catagactcg | gtgcaccggc | ttggctacgt | 780 |
| gcacagggac | atcaaacccg | acaacatcct | gctggaccgc | tgtggccaca | tccgcctggc | 840 |
| cgacttcggc | tcttgcctca | agctgcgggc | agatggaacg | gtgcggtcgc | tgtggctgt | 900 |
| gggcaccccca | gactacctgt | ccccgagat | cctgcaggct | gtgggcggtg | gcctgggac | 960 |
| aggcagctac | gggcccgagt | gtgactggtg | ggcgctgggt | gtattcgcct | atgaaatgtt | 1020 |
| ctatgggcag | acgcccttct | acgcggattc | cacgcggag | acctatggca | agatcgtcca | 1080 |
| ctacaaggag | cacctctctc | tgccgctggt | ggacgaaggg | gtccctgagg | aggctcgaga | 1140 |
| cttcattcag | cggttgctgt | gtccccgga | gacacggctg | ggccggggtg | gagcaggcga | 1200 |
| cttccggaca | catcccttct | tctttggcct | cgactgggat | ggtctccggg | acagcgtgcc | 1260 |
| cccctttaca | ccggatttcg | aaggtgccac | cgacacatgc | aacttcgact | tggtggagga | 1320 |
| cgggctcact | gccatggaga | cactgtcgga | cattcgggaa | ggtgcgccgc | taggggtcca | 1380 |
| cctgcctttt | gtgggctact | cctactcctg | catggccctc | agggacagtg | aggtcccagg | 1440 |
| ccccacaccc | atggaactgg | aggccgagca | gctgcttgag | ccacacgtgc | aagcgcccag | 1500 |
| cctggagccc | tcggtgtccc | cacaggatga | aacagctgaa | gtggcagttc | cagcggctgt | 1560 |
| ccctgcggca | gaggctgagg | ccgaggtgac | gctgcgggag | ctccaggaag | ccctggagga | 1620 |
| ggaggtgctc | acccggcaga | gcctgagccg | ggagatggga | gccatccgca | cggacaacca | 1680 |
| gaacttcgcc | agtcaactac | gcgaggcaga | ggctcggaac | cgggacctag | aggcacacgt | 1740 |
| ccggcagttg | caggagcgga | tggagttgct | gcaggcagag | ggagccacag | ctgtcacggg | 1800 |
| ggtccccagt | ccccgggcca | cggatccacc | ttcccatcta | gatggccccc | cggccgtggc | 1860 |
| tgtgggccag | tgcccgctgg | tggggccagg | cccatgcac | cgccgccacc | tgctgctccc | 1920 |
| tgccagggtc | cctaggcctg | gcctatcgga | ggcgctttcc | ctgctcctgt | cgccgttgt | 1980 |
| tctgtctcgt | gccgccgccc | tgggctgcat | tgggttggtg | gcccacgccg | gccaactcac | 2040 |

| | | |
|---|---|---|
| cgcagtctgg cgccgcccag gagccgcccg cgctccctga accctagaac tgtcttcgac | 2100 | |
| tccggggccc cgttggaaga ctgagtgccc ggggcacggc acagaagccg cgcccaccgc | 2160 | |
| ctgccagttc acaaccgctc cgagcgtggg tctccgccca gctccagtcc tgtgatccgg | 2220 | |
| gcccgccccc tagcggccgg ggagggaggg gccgggtccg cggccggcga acggggctcg | 2280 | |
| aagggtcctt gtagccggga atgctgctgc tgctgctgct gctgctgctg ctgctgctgc | 2340 | |
| tgctgctgct gctgctgctg ctgggggggat cacagaccat ttctttcttt cggccaggct | 2400 | |
| gaggccctga cgtggatggg caaactgcag gcctgggaag gcagcaagcc gggccgtccg | 2460 | |
| tgttccatcc tccacgcacc cccacctatc gttggttcgc aaagtgcaaa gctttcttgt | 2520 | |
| gcatgacgcc ctgctctggg gagcgtctgg cgcgatctct gcctgcttac tcgggaaatt | 2580 | |
| tgcttttgcc aaaccgcgtt tttcggggat cccgcgcccc cctcctcact gcgctgctc | 2640 | |
| tcggagcccc agccggctcc gcccgcttcg gcggtttgga tatttattga cctcgtcctc | 2700 | |
| cgactcgctg acaggctaca ggaccccaa caaccccaat ccacgttttg gatgcactga | 2760 | |
| gaccccgaca ttcctcggta tttattgtct gtccccacct aggaccccca ccccgaccc | 2820 | |
| tcgcgaataa aaggccctcc atctgcccaa aaaaaaaaa aaaaaaaaa aaaaaaa | 2877 | |

<210> SEQ ID NO 27
<211> LENGTH: 2873
<212> TYPE: DNA
<213> ORGANISM: Homo sapiens

<400> SEQUENCE: 27

| | | |
|---|---|---|
| agggggggctg gaccaagggg tggggagaag gggaggaggc ctcggccggc cgcagagaga | 60 | |
| agtggccaga gaggcccagg ggacagccag ggacaggcag acatgcagcc agggctccag | 120 | |
| ggcctggaca ggggctgcca ggccctgtga caggaggacc ccgagccccc ggcccgggga | 180 | |
| ggggccatgg tgctgcctgt ccaacatgtc agccgaggtg cggctgaggc ggctccagca | 240 | |
| gctggtgttg gacccgggct tcctggggct ggagcccctg ctcgaccttc tcctgggcgt | 300 | |
| ccaccaggag ctgggcgcct ccgaactggc ccaggacaag tacgtggccg acttcttgca | 360 | |
| gtgggcggag cccatcgtgg tgaggcttaa ggaggtccga ctgcagaggg acgacttcga | 420 | |
| gattctgaag gtgatcggac gcgggggcgtt cagcgaggta gcggtagtga agatgaagca | 480 | |
| gacgggccag gtgtatgcca tgaagatcat gaacaagtgg gacatgctga agaggggcga | 540 | |
| ggtgtcgtgc ttccgtgagg agagggacgt gttggtgaat ggggaccggc ggtggatcac | 600 | |
| gcagctgcac ttcgccttcc aggatgagaa ctacctgtac ctggtcatgg agtattacgt | 660 | |
| gggcggggac ctgctgacac tgctgagcaa gtttggggag cggattccgg ccgagatggc | 720 | |
| gcgcttctac ctggcggaga ttgtcatggc catagactcg gtgcaccggc ttggctacgt | 780 | |
| gcacagggac atcaaacccg acaacatcct gctggaccgc tgtggccaca tccgcctggc | 840 | |
| cgacttcggc tcttgcctca agctgcgggc agatggaacg gtgcggtcgc tgtggctgt | 900 | |
| gggcacccca gactacctgt cccccgagat cctgcaggct gtgggcggtg gcctgggac | 960 | |
| aggcagctac gggcccgagt gtgactggtg ggcgctgggt gtattcgcct atgaaatgtt | 1020 | |
| ctatgggcag acgccttcct acgcggattc cacggcggag acctatggca agatcgtcca | 1080 | |
| ctacaaggag cacctctctc tgccgctggt ggacgaaggg gtccctgagg aggctcgaga | 1140 | |
| cttcattcag cggttgctgt gtccccggga gacggcctg gccggggtg agcaggcga | 1200 | |
| cttccggaca catcccttct tctttggcct cgactgggat ggtctccggg acagcgtgcc | 1260 | |
| ccccttaca ccggatttcg aaggtgccac cgacacatgc aacttcgact tggtggagga | 1320 | |

-continued

```
cgggctcact gccatggaga cactgtcgga cattcgggaa ggtgcgccgc taggggtcca    1380 cctgccttt  gtgggctact cctactcctg catggccctc agggacagtg aggtcccagg    1440
ccccacaccc atggaactgg aggccgagca gctgcttgag ccacacgtgc aagcgcccag    1500
cctggagccc tcggtgtccc cacaggatga aacagctgaa gtggcagttc cagcggctgt    1560
ccctgcggca gaggctgagg ccgaggtgac gctgcgggag ctccaggaag ccctggagga    1620
ggaggtgctc acccggcaga gcctgagccg ggagatggag gccatccgca cggacaacca    1680
gaacttcgcc agtcaactac gcgaggcaga ggctcggaac cgggacctag aggcacacgt    1740
ccggcagttg caggagcgga tggagttgct gcaggcagag ggagccacag ctgtcacggg    1800
ggtccccagt ccccgggcca cggatccacc ttcccatatg gccccccggc cgtggctgtg    1860
ggccagtgcc cgctggtggg gccaggcccc atgcaccgcc gccacctgct gctccctgcc    1920
agggtcccta ggcctggcct atcggaggcg cttccctgc tcctgttcgc cgttgttctg    1980
tctcgtgccg ccgccctggg ctgcattggg ttggtggccc acgccggcca actcaccgca    2040
gtctggcgcc gcccaggagc cgcccgcgct ccctgaaccc tagaactgtc ttcgactccg    2100
gggccccgtt ggaagactga gtgcccgggg cacggcacag aagccgcgcc caccgcctgc    2160
cagttcacaa ccgctccgag cgtgggtctc cgcccagctc cagtcctgtg atccgggccc    2220 gcccctagc  ggccggggag ggaggggccg ggtccgcggc cggcgaacgg ggctcgaagg    2280
gtccttgtag ccgggaatgc tgctgctgct gctgctgctg ctgctgctgc tgctgctgct    2340
gctgctgctg ctgctgctgg ggggatcaca gaccatttct ttctttcggc caggctgagg    2400
ccctgacgtg gatgggcaaa ctgcaggcct gggaaggcag caagccgggc cgtccgtgtt    2460
ccatcctcca cgcaccccca cctatcgttg gttcgcaaag tgcaaagctt tcttgtgcat    2520
gacgccctgc tctggggagc gtctggcgcg atctctgcct gcttactcgg gaaatttgct    2580
tttgccaaac ccgcttttc  ggggatcccg cgcccccctc ctcacttgcg ctgctctcgg    2640
agccccagcc ggctccgccc gcttcggcgg tttggatatt tattgacctc gtcctccgac    2700
tcgctgacag gctacaggac ccccaacaac cccaatccac gttttggatg cactgagacc    2760
ccgacattcc tcggtattta ttgtctgtcc ccacctagga cccccacccc cgaccctcgc    2820
gaataaaagg ccctccatct gcccaaaaaa aaaaaaaaa aaaaaaaaaa aaa           2873
```

ANTISENSE CONJUGATES FOR DECREASING EXPRESSION OF DMPK

RELATED APPLICATIONS

This application is a national stage filing under 35 U.S.C. 371 of International Application No. PCT/US2013/031718, filed Mar. 14, 2013, which claims the benefit of the filing date under 35 U.S.C. 119(e) to U.S. provisional application No. 61/612,065, filed Mar. 16, 2012, the disclosure of which is hereby incorporated by reference in its entirety. International Application No. PCT/US2013/031718 was published under PCT Article 21(2) in English.

The instant application contains a Sequence Listing which has been submitted via EFS-Web and is hereby incorporated by reference in its entirety. Said ASCII copy, created on Sep. 16, 2014, is named 1061990018301_Seq.txt, and is 48,753 bytes in size.

BACKGROUND OF THE INVENTION

Myotonic dystrophy (DM or Steinert's disease) is a multisystemic, dominantly inherited disorder often characterized by myotonia or delayed muscle relaxation due to repetitive action potentials in myofibers, and muscle degeneration. Manifestations of DM may also include heart block, ocular cataracts, hypogonadism, and nervous system dysfunction. For example, DM patients often suffer from cardiac conduction defects, smooth muscle involvement, hypersomnia, cataracts, abnormal glucose response, and, in males, premature balding and testicular atrophy. Myotonic dystrophy is the most common muscular dystrophy of adults for which there are no effective therapies.

Myotonic dystrophy type 1 is an RNA-dominant disease caused by abnormal transcripts of the DMPK (dystrophia myotonica protein kinase) gene. The DMPK is a protein expressed by four different mRNA splice variants in skeletal muscle, heart and brain. See, e.g., Brook, 1992, Cell, 68(4): 799-808; Mahadevan, 1992, Science, 255(5049): 1253-55; Fu, 1992, Science, 255(5049): 1253-55; Tsilfidis, 1992, Nat. Genet., 1(3): 192-195. DM1 patients have trinucleotide repeat expansions in the 3'-untranslated region, leading to mRNA transcripts with long region of CUG repeats (e.g., greater than 50 to 3000 repeats in afflicted patients). These CUG expanded transcripts aggregate in the nucleus and form RNA foci that have, at least, the following deleterious effects on certain splicing regulatory proteins: deplete muscleblind protein (MBNL1) and misregulate CUGBP Elav family member 1 (CELF1).

SUMMARY OF THE DISCLOSURE

It is a goal of the present disclosure to provide agents suitable for delivery to muscle cells, including skeletal and cardiac muscle. Such agents are particularly suited for studying and modulating the defects observed in cells having expanded CUG repeats in a DMPK transcript.

The disclosure provides compositions useful for promoting delivery of agents to cells, such as to muscle cells. Numerous agents that have potential therapeutic potential fail to achieve efficacy in animal models or human patients due to suboptimal delivery into cells, such as into a target cell type. The present disclosure addresses this issue by providing antisense conjugates and other agents that transit cell membranes, including into cells, such as muscle cells (e.g., skeletal and cardiac muscle). As such, the present disclosure provides compositions that are particularly well suited for studying and treating muscle disorders, such as myotonic dystrophy.

The disclosure provides conjugates, as well as methods of making and using such conjugates. Generally, the disclosure provides conjugates comprising at least two portions: an antisense oligonucleotide portion and an internalizing moiety portion. For example, the disclosure provides conjugates in which the antisense oligonucleotide portion comprises an antisense oligonucleotide that hybridizes to a DMPK gene or transcript, e.g., to a 3'UTR of a transcript comprising the sequence of any one of SEQ ID NOs: 24-27. In some embodiments, the antisense oligonucleotide binds to at least a portion of the 3'UTR of the DMPK transcript. In some embodiments, the antisense oligonucleotide binds to any one of SEQ ID NOs: 24-27. By way of further example, the disclosure provides conjugates in which the internalizing moiety portion is an antibody or antigen binding fragment selected from: monoclonal antibody 3E10, or a variant thereof that retains the cell penetrating activity of 3E10, or a variant thereof that retain cell penetrating activity, or a variant thereof that binds the same epitope as 3E10, or an antibody that has substantially the same cell penetrating activity as 3E10 and binds the same epitope as 3E10, or an antigen binding fragment of any of the foregoing. Conjugates of the disclosure (also referred to as antisense conjugates or antisense conjugates of the disclosure) comprise at least an antisense oligonucleotide portion and an internalizing moiety portion.

In a first aspect, the disclosure provides a conjugate comprising at least two portions. For example, in a first aspect the disclosure provides a conjugate comprising: an antisense oligonucleotide that hybridizes to a DMPK gene or transcript (e.g., an antisense oligonucleotide portion); and an antibody or antigen binding fragment selected from: monoclonal antibody 3E10, or a variant thereof that retains the cell penetrating activity of 3E10, or a variant thereof that binds the same epitope as 3E10, or a variant thereof that retain cell penetrating activity, or an antibody that has substantially the same cell penetrating activity as 3E10 and binds the same epitope as 3E10, or an antigen binding fragment of any of the foregoing (e.g., an internalizing moiety portion). In certain embodiments, the antisense oligonucleotide hybridizes to a DMPK transcript, e.g., to a 3'UTR of a transcript comprising the sequence of any one of SEQ ID NOs: 24-27. In some embodiments, the antisense oligonucleotide binds to at least a portion of the 3'UTR of the DMPK transcript. In some embodiments, the antisense oligonucleotide binds to the coding region of DMPK (e.g., to any one of SEQ ID NOs: 24-27). Suitable antisense oligonucleotides may be single stranded or double stranded.

In a second aspect, the disclosure provides a conjugate comprising at least three portions. For example, in a first aspect the disclosure provides a conjugate comprising: an MBNL1 polypeptide or a functional fragment thereof comprising all four zinc fingers; and an antibody or antigen binding fragment selected from: monoclonal antibody 3E10, or a variant thereof that retains the cell penetrating activity of 3E10, or a variant thereof that binds the same epitope as 3E10, or a variant thereof that retain cell penetrating activity, or an antibody that has substantially the same cell penetrating activity as 3E10 and binds the same epitope as 3E10, or an antigen binding fragment of any of the foregoing (e.g., an internalizing moiety portion); and an antisense oligonucleotide that hybridizes to a DMPK gene or transcript (e.g., an antisense oligonucleotide portion). In certain embodiments, the antisense oligonucleotide hybridizes to a DMPK transcript, e.g., to a 3'UTR of a transcript comprising the sequence of any one of SEQ ID NOs: 24-27. Suitable antisense oligonucleotides may be single stranded or double stranded. In certain embodiments, the MBNL portion of the conjugate is interconnected to the internalizing moiety portion and the internalizing moiety portion is interconnected to the antisense oligonucleotide portion.

In certain embodiments of any of the foregoing, or of any of the aspects and embodiments disclosed herein, the conjugate comprises an antibody or antigen binding fragment, and that antibody or antigen binding fragment is a murine, chimeric, humanized, or fully human antibody or antigen binding fragment. In some embodiments, the antibody or antigen binding fragment is humanized. In other embodiments, the antibody or antigen binding fragment comprises a heavy chain variable domain (VH) comprising an amino acid sequence at least 95% identical to SEQ ID NO: 13. In other embodiments, the antibody or antigen binding fragment comprises a heavy chain variable domain (VH) comprising an amino acid sequence at least 95% identical to SEQ ID NO: 13, or a humanized variant thereof. In other embodiments, the antibody or antigen binding fragment comprises a light chain variable domain (VL) comprising an amino acid sequence at least 95% identical to SEQ ID NO: 14. In other embodiments, the antibody or antigen binding fragment comprises a light chain variable domain (VL) comprising an amino acid sequence at least 95% identical to SEQ ID NO: 14, or a humanized variant thereof. In other embodiments, the antibody or antigen binding fragment comprises a heavy chain variable domain (VH) comprising the amino acid sequence of SEQ ID NO: 13 and a light chain variable domain (VL) comprising the amino acid sequence of SEQ ID NO: 14, or a humanized variant thereof. In certain other embodiments, the antibody or antigen binding fragment comprises a VH CDR1 having the amino acid sequence of SEQ ID NO: 16;
a VH CDR2 having the amino acid sequence of SEQ ID NO: 17;
a VH CDR3 having the amino acid sequence of SEQ ID NO: 18;
a VL CDR1 having the amino acid sequence of SEQ ID NO: 19;
a VL CDR2 having the amino acid sequence of SEQ ID NO: 20;
a VL CDR3 having the amino acid sequence of SEQ ID NO: 21.

In certain embodiments of any of the foregoing, or of any of the aspects and embodiments disclosed herein, the antisense oligonucleotide hybridizes to CUG repeats of the DMPK transcript, e.g., to a 3'UTR of a transcript comprising the sequence of any one of SEQ ID NOs: 24-27. In other embodiments, the antisense oligonucleotide hybridizes to coding sequence of the DMPK transcript. In other embodiments, the antisense oligonucleotide hybridizes to the DMPK gene. In certain embodiments, the antisense oligonucleotide preferentially hybridizes to a region of expanded CUG repeats (e.g., a CUG-expanded region of a transcript) relative to a region that has wildtype number of CUG repeats (e.g., not CUG-expanded). In certain embodiments, the antisense oligonucleotide is a single stranded oligonucleotide. In other embodiments, the antisense oligonucleotide is a double stranded oligonucleotide. In other embodiments, the antisense oligonucleotide has at least one single stranded region and at least one double stranded region. In some embodiments, the antisense oligonucleotide is a gapmer. In some embodiments, the antisense oligonucleotide is a morpholino.

In certain embodiments of any of the foregoing, or of any of the aspects and embodiments disclosed herein, the antisense oligonucleotide comprises 14 nucleotides. In other embodiments, the antisense oligonucleotide comprises 14, 15, 16, 17, 18, 19, or 20 nucleotides. In other embodiments, the antisense oligonucleotide comprises 20, 21, 22, 23, 24, 25, 26, 27, 28, 29, 30, 31, 32, 33, 34, 35, 36, 37, 38, 39, or 40 nucleotides. In other embodiments, the antisense oligonucleotide comprises 14-50, 14-40, 14-30, 14-25, 14-24, 14-23, 14-22, 14-21, or 14-20 nucleotides. In other embodiments, the antisense oligonucleotide comprises 14-19, 14-18, 14-17, or 14-16 nucleotides. In other embodiments, the antisense oligonucleotide comprises 15-25, 15-20, 15-19, 15-18, 15-17, 16-25, 16-20, 16-19, 16-18, 17-25, 17-20, 17-19, 18-25, 18-20, or 19-25 nucleotides. It should be understood that a reference to nucleotide includes modified as well as unmodified nucleotides, and a modified nucleotide may have a modification in any portion (e.g., backbone, base, etc.). In certain embodiments, the antisense oligonucleotide consists of any of the foregoing number or range of nucleotides.

In certain embodiments of any of the foregoing, or of any of the aspects and embodiments disclosed herein, the antisense oligonucleotide is capable, upon hybridization to its target sequence, of mediating (e.g., promoting) RNaseH-mediated degradation. Note, however, that an oligonucleotide capable of mediating RNaseH-mediated degradation may also have other effects, and that does not alter its characterization as an antisense oligonucleotide capable of mediating RNaseH-mediated degradation. For example, in certain embodiments, the antisense oligonucleotide comprises a central portion of at least 7 nucleotides, which central portion of at least 7 nucleotides is capable of mediating RNase H-mediated degradation following hybridization to RNA. In certain embodiments, the central portion of at least 7 nucleotides is composed of unmodified DNA nucleotides, phosphorothioate nucleotides, or a combination thereof. Phosphorothioate nucleotides are one example of modified nucleotides. In this case, a class of modification that retains the ability to mediate RNaseH-mediated degradation.

In some embodiments, the antisense oligonucleotide sterically inhibits binding of MBNL1 to a nucleotide sequence. In some embodiments, the antisense oligonucleotide prevents proteins or nucleic acids from binding to DMPK transcript, e.g., to a 3'UTR of a transcript comprising the sequence of any one of SEQ ID NOs: 24-27. In some embodiments, the nucleotide sequence is the DMPK transcript nucleotide sequence. In some embodiments, the DMPK transcript nucleotide sequence has expanded CUG repeats, e.g., expanded CUG repeats in the 3'UTR of a transcript comprising the sequence of any one of SEQ ID NOs: 24-27.

In certain embodiments of any of the foregoing, or of any of the aspects and embodiments disclosed herein, the antisense oligonucleotide has an organization that can be represented by the following formula: wing-central portion-wing. Preferably, the central portion comprises nucleotides capable of mediating RNaseH-mediated degradation upon hybridization to its target. Thus, in certain embodiments, the antisense oligonucleotide comprises two wing portions, each of which flank a central portion. In certain embodiments, each of the two wing portions comprises at least 3 nucleotides. For example, each of the two wing portions may comprise 3, 4 or 5 nucleotides. The lengths of the two wing portions may be the same or different. When different, the length of each wing portion is independently selected. It should be understood that, since the primary nucleotide sequence of the antisense oligonucleotide depends on the target sequence to which it is directed, there is no requirement or expectation that the wing portions will have the same primary nucleotide sequence, although they may.

In certain embodiments of any of the foregoing, or of any of the aspects and embodiments disclosed herein, the two wing portions comprise at least 3 nucleotides modified to increase stability or specificity of the oligonucleotide. Similarly, 1 or 2 of the 3 nucleotides of a wing portion may be modified to increase stability or specificity (e.g., the wing portion may comprise a mixture of modified and non-modified nucleotides). When more than one nucleotide is modified, it should be understood that such modifications may be the same or may be different. In certain embodiments, each of the two wing portions comprises at least 3 nucleotides, and each of the 3 nucleotides comprises the same type of modification. In certain embodiments, each of the two wing portions comprises at least 3 nucleotides modified to increase stability or specificity of the oligonucleotide, but which nucleotides do not induce RNaseH-mediated degradation following hybridization to RNA.

In certain embodiments of any of the foregoing, or of any of the aspects and embodiments disclosed herein, each of the two wing portions is composed of one or more of the following: unmodified RNA nucleotides, locked nucleic acid (LCA) nucleotides, 2'-O-methoxyethyl nucleotides, 2'-O-methyl nucleotides, a peptide nucleic acid, a hexitol nucleic acid, an N3'-P5'-phosphoroamidate, or a conformationally restricted nucleotide (CRN). In certain embodiments, the wing portions comprise only modified nucleotides, and the modifications may all be the same or may be different. For example, in certain embodiments, the two wing portions comprise the same classes of modifications, but may comprise a different primary nucleotide sequence. In certain embodiments, all of the nucleotides of each of the two wings comprise the same class of modification selected from one of the following: locked nucleic acid (LNA) nucleotides, 2'-O-methoxyethyl nucleotides, 2'-O-methyl nucleotides, a peptide nucleic acid, a hexitol nucleic acid, an N3'-P5'-phosphoroamidate, or conformationally restricted nucleotides (CRN). Once again, however, this does not alter the fact that the wings may have a different primary nucleotide sequence. In certain embodiments, the two wing portions of these oligonucleotides are modified in a way other than that indicated in the sequence listing. In certain embodiments, the two wing portions of the antisense oligonucleotides comprise LNA (e.g., a type of modification) nucleotides or 2'-O-methoxyethyl (e.g., another type of modification) nucleotides. In other embodiments, the two wing portions of the antisense oligonucleotides comprise CRN (e.g., yet another type of modification) nucleotides.

In certain embodiments of any of the foregoing, or of any of the aspects and embodiments disclosed herein, the antisense oligonucleotide that binds to the DMPK transcript comprises the oligonucleotide sequence set forth in any of SEQ ID NOs: 9-12 or 22-23. In certain embodiments of any of the foregoing, or of any of the aspect and embodiments disclosed herein, a conjugate comprises an antigen binding fragment (as the internalizing moiety), and the antisense oligonucleotide is conjugated to the C-terminus of the antigen binding fragment. In other embodiments, the conjugate comprises an antigen binding fragment, and the antisense oligonucleotide is conjugated to the N-terminus of the antigen binding fragment. In either case, the antigen binding fragment may be an scFv, and the antisense oligonucleotide may be conjugated to the N- or C-terminus of the scFv. For example, an additional free cysteine residue may be added to the C-terminus of the scFv to provide a site for site-directed chemical conjugation of the antisense oligonucleotide to the scFv to form a conjugate. In still other embodiments, a conjugate comprises a full length antibody, and the antisense oligonucleotide is conjugated to an Fc portion of the antibody. Numerous chemistries and methodologies for conjugating oligonucleotides to polypeptides exist and may be used. A few illustrative examples are provided herein.

In certain embodiments of any of the foregoing, or of any of the aspects and embodiments disclosed herein, a free cysteine is added to the antibody or antigen binding fragment (internalizing moiety), and the antisense oligonucleotide is conjugated by site directed chemical conjugation via the free cysteine.

In certain embodiments of any of the foregoing, or of any of the aspects and embodiments disclosed herein, the ratio of antisense oligonucleotide conjugated per antibody or antibody fragment is 1:1. For example, in certain embodiments, the antibody fragment (e.g., antigen binding fragment) comprises an scFv, and the ratio of antisense oligonucleotide to scFv in the conjugate is 1:1. In certain embodiments, the antibody or antigen binding fragment is an scFv, and one antisense oligonucleotide is conjugated per scFv.

In certain embodiments of any of the foregoing, or of any of the aspects and embodiments disclosed herein, portions of the conjugate may be interconnected directly or via a linker. For example, in certain embodiments, the internalizing moiety (the antibody or antigen binding fragment) is conjugated to the antisense oligonucleotide via a linker. Similarly, for conjugates comprising at least three portions, the MBNL portion may be conjugated or otherwise interconnected (such as, as a fusion protein) to the internalizing moiety (the antibody or antigen binding fragment) via a linker. In addition to linkers that may interconnect portions of conjugates, additional linkers may be present. For example, for conjugates comprising an scFv, the variable heavy chain domain and the variable light chain domain may be interconnected via a flexible linker. Suitable linkers include cleavable or non-cleavable linkers. When the conjugate comprises more than one linker, the linkers are independently selected and may be the same size and/or composition or different.

In certain embodiments of any of the foregoing, or of any of the aspects and embodiments disclosed herein, the conjugate is capable of penetrating muscle cells. In certain embodiments, the conjugate penetrates muscle cells more efficiently than the same antisense oligonucleotide administered alone in an unconjugated form. In other embodiments, the conjugate penetrates muscle cells (e.g., skeletal and/or cardiac) more efficiently than the same antisense oligonucleotide administered as a conjugate with cell penetrating peptide of HIV-Tat. In certain embodiments, the muscle cells are in vivo, such as in a healthy animal or animal model, and penetration into muscle cells is measured and compared in this context. Thus, when evaluating cell penetrating ability, in certain embodiments, the suitable comparison is made in an in vivo context.

In certain embodiments of any of the foregoing, or of any of the aspects and embodiments disclosed herein, the antisense oligonucleotide hybridizes to a DMPK transcript and promotes degradation of the transcript.

In certain embodiments, the conjugate further comprises a muscle blind protein (MBNL1) or a functional fragment thereof interconnected to the antibody or antibody fragment.

In another aspect, the disclosure provides compositions comprising any of the conjugate of the disclosure (a conjugate having any combination of features described herein) formulated in a physiologically acceptable carrier. In some embodiments, the composition is substantially pyrogen-free.

In another aspect, the disclosure provides methods of making a conjugate of the disclosure. For example, the two portions of the conjugate can be made and then interconnected, such as by any available chemical conjugation method. For example, the antisense oligonucleotide is a short nucleotide sequence which can be chemically synthesized. The antibody or antigen binging fragment can be made recombinantly, such as by expressing a nucleotide sequence encoding the protein in cell culture and purifying the protein from the cell culture. After making the components of the conjugate, such components can be interconnected directly or via a linker.

In another aspect, the disclosure provides a method of treating myotonic dystrophy. The method comprises administering to a patient in need thereof any one or more of the conjugates or compositions of the disclosure. Following administration, patients can be monitored for improvement in one or more symptoms. In some embodiments, the method improves muscle weakness, muscle wasting, grip strength, cataracts, difficulty relaxing grasp, irregularities in heartbeat, constipation and other digestive problems, retinal degeneration, low IQ, cognitive defects, frontal balding, skin disorders, atrophy of the testicles, insulin resistance or sleep apnea in said patient. In some embodiments of the method, the conjugate is administered systemically.

In some embodiments, the conjugate is administered locally. In some embodiments, the conjugate is administered intravenously. In some embodiments, administered locally comprises administering via the hepatic portal vein. In some embodiments, the conjugate is administered intramuscularly.

In another aspect, the disclosure provides a method of promoting entry into muscle cells. The method comprises contacting cells or administering to a patient any one or more of the conjugates or compositions of the disclosure. Following administration, cells or patients can be monitored to confirm entry into cells of the conjugates or compositions. Additionally, cells may be examined to evaluate functional activity of the antisense oligonucleotide portion of the conjugate. For example, functional activity may be assessed by assaying decreased expression of DMPK, decreased nuclear foci, etc.

In another aspect, the disclosure provides a method of treating myotonic dystrophy. The method comprises administering to a patient in need thereof two therapeutics, either simultaneously or concurrently, and wherein the therapeutics comprise:
any one or more of the conjugates or compositions of the disclosure; and
a chimeric polypeptide comprising:
  (a) an MBNL1 polypeptide or a functional fragment thereof comprising all four zinc finger motifs; and
  (b) an antibody or antigen binding fragment selected from: monoclonal antibody 3E10, or a variant thereof that retains the cell penetrating activity of 3E10, or a variant thereof that retains the cell penetrating activity, or a variant thereof that binds the same epitope as 3E10, or an antibody that has substantially the same cell penetrating activity as 3E10 and binds the same epitope as 3E10, or an antigen binding fragment of any of the foregoing.

In another aspect, the disclosure provides various kits. For example, in one embodiment, the disclosure provides a kit comprising a container comprising a conjugate or composition of the disclosure; and instructions for research or therapeutic use. Optionally, the kit may comprise more than one conjugate of the disclosure, and additional conjugates may be provided in separate containers. Optionally, a kit may comprise suitable buffers to reconstitute a lyophilized conjugate or composition (in scenarios where the active agents are provided as lyophilized formulations requiring reconstitution).

Another exemplary kit comprises a first container comprising a conjugate or composition of the disclosure; and a second container comprising a chimeric polypeptide comprising: (a) an MBNL1 polypeptide or a functional fragment thereof comprising all four zinc finger motifs; and
(b) an antibody or antigen binding fragment selected from: monoclonal antibody 3E10, or a variant thereof that retains the cell penetrating activity of 3E10, or a variant thereof that retains cell penetrating activity, or a variant thereof that binds the same epitope as 3E10, or an antibody that has substantially the same cell penetrating activity as 3E10 and binds the same epitope as 3E10, or an antigen binding fragment of any of the foregoing. Such a kit may also include instructions for research or therapeutic use. Optionally, such a kit may include suitable buffers to reconstitute a lyophilized agent in either the first or the second container (in scenarios where one or both of the active agents are provided as lyophilized formulations requiring reconstitution).

The disclosure contemplates all combinations of any of the foregoing aspects and embodiments with each other, as well as combinations with any of the embodiments set forth in the detailed description and examples.

DETAILED DESCRIPTION OF THE INVENTION

Myotonic dystrophy (DM) is an autosomal dominant neuromuscular disease which is the most common form of muscular dystrophy affecting adults. The clinical picture in DM is well established but exceptionally variable. Although generally considered a disease of muscle, with myotonia, progressive weakness and wasting, DM is characterized by abnormalities in a variety of other systems. DM patients often suffer from cardiac conduction defects, smooth muscle involvement, hypersomnia, cataracts, abnormal glucose response, and, in males, premature balding and testicular atrophy. The mildest form, which is occasionally difficult to diagnose, is seen in middle or old age and is characterized by cataracts with little or no muscle involvement. The classical form, showing myotonia and muscle weakness, most frequently has onset in early adult life and in adolescence. The most severe form is associated with generalized muscular hypoplasia, mental retardation, and high neonatal mortality.

Myotonic dystrophy type 1 (DM1) is caused by a trinucleotide $(CTG)_n$ expansion (n=50 to >3000) in the 3'-untranslated region (3'UTR) of the Dystrophia myotonica-protein kinase (DMPK) gene, which is also referred to as the myotonin-protein kinase. As used herein, the term "DMPK transcript" refers to the coding region for the DMPK protein (e.g., any one of SEQ ID NOs: 24-27) as well as to the 3'UTR and 5'UTR regions, the 5' cap and the poly-A tail.

Myotonin-protein kinase is a serine-threonine kinase that is closely related to other kinases that interact with members of the Rho family of small GTPases. Substrates for this enzyme include myogenin, the beta-subunit of the L-type calcium channels, and phospholemman.

The 3' untranslated region of this gene normally contains 5-37 copies of a CTG trinucleotide repeat. Expansion of this unstable motif to 50-5,000 copies causes myotonic dystrophy type I. Generally, the severity of the disease increases with increasing repeat element copy number. Repeat expansion is associated with condensation of local chromatin structure that disrupts the expression of genes in this region.

The present disclosure provides antisense conjugates that can be used to help decrease expression of DMPK, including DMPK with deleterious trinucleotide repeat expansion. The use of unconjugated antisense oligonucleotides has been demonstrated. See, for example, Lee et al., 2012, Proc. Natl. Acad. Sci. 109, 4221-4226, which is incorporated by reference in its entirety. However, antisense conjugates and approaches to promote efficient, or even improved, delivery of antisense oligonucleotides into cells, such as muscle cells, has not been taught or accomplished.

The present disclosure provides such antisense conjugates, as well as methods of using such antisense conjugates. Additionally, the present disclosure provides combination approaches in which antisense conjugates of the disclosure are administered with MBNL1 chimeric polypeptides comprising the same or a similar internalizing domain as that described herein for the antisense conjugates. Similarly, the disclosure contemplates use of multiple antisense conjugates, such as two conjugate—each of which hybridizes to a different portion of DMPK. Finally, the present disclosure provides conjugates comprising three components: an MBNL portion, an antibody or antigen binding fragment portion, and an antisense oligonucleotide that hybridizes to a DMPK gene or transcript. These features of the disclosure are discussed in more detail below.

Before outlining in detail the specific features and characteristics of each portion of the antisense conjugates and chimeric polypeptides of the disclosure, a general overview of these composition is provided.

In one aspect, the disclosure provides antisense conjugates. Antisense conjugates comprise at least two portions: (i) the antisense oligonucleotide portion and (ii) the internalizing moiety portion. As described in detail below, the antisense oligonucleotide portion comprises an antisense oligonucleotide that hybridizes to a DMPK transcript, such as a human DMPK transcript, e.g., 3'UTR of a transcript comprising the sequence of any one of SEQ ID NOs: 24-27. Various types, sizes and chemistries for antisense oligonucleotides are described below, and the disclosure contemplates the use of any such disclosed types, sizes, and chemistries. The antisense oligonucleotide may hybridize to the 3'UTR of the DMPK transcript, such as to a region that include CUG repeats, such as expanded CUG repeats. Alternatively, the antisense oligonucleotide may hybridize to another portion of the DMPK transcript, such as an exon in the translated region of the transcript. In some embodiments, the antisense conjugate binds to/hybridizes to at least a portion of the 3'UTR of the DMPK transcript. In some embodiments, the antisense conjugate binds to/hybridizes to CUG repeats in the 3'UTR of the DMPK transcript. In some embodiments, the antisense conjugate binds to/hybridizes to the coding region of DMPK (e.g., to any one of SEQ ID NOs: 24-27).

Although antisense oligonucleotides may function via any of a number of mechanisms, in certain embodiments, the antisense conjugates promote degradation of the DMPK transcript. In certain embodiments, the antisense conjugates promote RNaseH-mediated degradation of the DMPK transcript. Note, however, that the disclosure contemplates that a given antisense conjugate may have multiple effects. Thus, in embodiments in which the mechanism of action of the antisense oligonucleotide is, at least in part, to promote degradation, as long as an antisense conjugate promotes RNaseH-mediated degradation, it may also have other effects (e.g., identification of a mechanism does not imply that such mechanism is the sole mechanism by which the antisense conjugate impacts a cell or transcript.

One type of antisense oligonucleotide contemplated when some level of RNaseH-mediated degradation is desired, are antisense oligonucleotides sometimes termed "gapmers". The oligonucleotides have a central portion that is flanked by two wing portions (e.g., wing-central portion-wing). The central portion has nucleotide content and chemistry capable of promoting RNaseH-mediated degradation when hybridized to RNA. For example, the central portion comprises at least 7 nucleotides of DNA and/or modified nucleotides that retain the ability to promote RNaseH-mediated degradation when hybridized to RNA, such as phosphorothioate nucleotides. The central portion may also contain a mixture of DNA and modified nucleotides, including mixtures of different modified nucleotides. Alternatively, the central portion may contain only DNA nucleotides or only modified nucleotides.

In contrast to the central portion, the wing portions are not intended to mediate RNaseH-mediated degradation. Rather, the wing portions are intended to improve the stability, half-life, or specificity of the oligonucleotides. Wing portions may include, for example, one or more modified nucleotides (including combinations) selected from: locked nucleic acid (LNA) nucleotides, 2'-O-methoxyethyl nucleotides, 2-O-methyl nucleotides, peptide nucleic acids, and the like. For any of these modified nucleotides provided in the wing portion, the modified nucleotides may be modified DNA or modified RNA nucleotides. Additional features of antisense oligonucleotides having the configuration: wing portion-central portion-wing portion are described below.

Antisense conjugates of the disclosure also include an internalizing moiety portion. This portion promotes entry of the conjugate into cells. Suitable internalizing moieties promote entry via an ENT transporter, e.g., an ENT1, ENT2, ENT3 or ENT4 transporter. ENT2 is expressed preferentially in certain cell types, including muscle (skeletal and cardiac). Accordingly, antisense conjugates are delivered into cells, but not ubiquitously. Rather, the conjugates are delivered with a level of specificity and enrichment for particular tissues, including skeletal and cardiac muscle.

I. Internalizing Moieties

As used herein, the term "internalizing moiety" refers to a moiety capable of interacting with a target tissue or a cell type to effect delivery of the attached molecule into the cell (i.e., penetrate desired cell; transport across a cellular membrane; deliver across cellular membranes to, at least, the cytoplasm). In certain embodiments, this disclosure relates to an internalizing moiety which promotes delivery into muscle cells (skeletal and cardiac), as well as certain other cell types. This portion promotes entry of the conjugate into cells. Suitable internalizing moieties promote entry via an ENT transporter, e.g., an ENT1, ENT2, ENT3 or ENT4 transporter. In some embodiments, the internalizing moiety promotes entry via an ENT2 transporter. ENT2 is expressed preferentially in certain cell types, including muscle (skeletal and cardiac). Accordingly, antisense conjugates are delivered into cells, but not ubiquitously. Rather, the conjugates are delivered with a level of specificity and enrichment for particular tissues, including skeletal and cardiac muscle.

As used herein, the internalizing moiety is associated (conjugated, linked or otherwise coupled) with an antisense oligonucleotide that hybridizes to a DMPK transcript (in the case of antisense conjugates of the disclosure) or with an MBNL1 polypeptide or functional fragment thereof (in the case of chimeric polypeptides comprising an MBNL1 polypeptide). The term "antisense conjugates" and "antisense conjugates of the disclosure" is used throughout to refer to a conjugate comprising an antisense oligonucleotide, such as an antisense oligonucleotide that hybridizes to a DMPK and an internalizing moiety, such as 3E10, an antibody that binds the same epitope and/or has the same cell penetrating activity and ENT2 mediated mechanism of penetration as 3E10, a variant of 3E10 that binds the same epitope and/or has the same cell penetrating activity and ENT2 mediated mechanism of penetration as 3E10, or an antigen binding fragment of any of the foregoing. In certain embodiments, an antisense conjugate may also comprise an MBNL1 polypeptide or functional fragment thereof.

Generally, conjugation to an antisense oligonucleotide is chemical conjugation, such as via the N or C terminus of the antibody or antigen binding fragment. Alternatively, when the conjugate comprises an antibody, conjugation may be chemical conjugation to one or more portions of the Fc region. In certain embodiments, conjugation is such that the ratio of antisense oligonucleotide:antibody/antigen binding fragment is 1:1 (e.g., one antisense oligonucleotide conjugated to one antibody or to one antigen binding fragment, such as one scFv).

In certain aspects, an internalizing moiety may comprise an antibody, including a monoclonal antibody, a polyclonal antibody, and a humanized antibody. Without being bound by theory, such antibody may bind to an antigen of a target tissue and thus mediate delivery to the target tissue (e.g., muscle, cancer cells, etc.). In some embodiments, internalizing moieties may comprise antibody fragments, derivatives or analogs thereof, including without limitation: Fv fragments, single chain Fv (scFv) fragments, Fab' fragments, F(ab')2 fragments, single domain antibodies, camelized antibodies and antibody fragments, humanized antibodies and antibody fragments, human antibodies and antibody fragments, and multivalent versions of the foregoing; multivalent internalizing moieties including without limitation: monospecific or bispecific antibodies, such as disulfide stabilized Fv fragments, scFv tandems ((scFv)$_2$ fragments), diabodies, tribodies or tetrabodies, which typically are covalently linked or otherwise stabilized (i.e., leucine zipper or helix stabilized) scFv fragments; receptor molecules which naturally interact with a desired target molecule. In certain embodiments, the antibodies or variants thereof, may be modified to make them less immunogenic when administered to a subject. For example, if the subject is human, the antibody may be "humanized", for example as described in Jones, P. et al. (1986), *Nature,* 321, 522-525 or Tempest et al. (1991), *Biotechnology,* 9, 266-273. In some embodiments, the internalizing moiety is any peptide or antibody-like protein having the complementarity determining regions (CDRs) of the 3E10 antibody sequence, or of an antibody that binds the same epitope as 3E10, such as the six CDRs set forth in SEQ ID NOs 16-21.

In certain embodiments, the internalizing moiety comprises the monoclonal antibody 3E10 or an antigen binding fragment thereof. For example, the antibody or antigen binding fragment thereof may be monoclonal antibody 3E10, or a variant thereof that retains the cell penetrating activity of 3E10, or a variant thereof that retains the cell penetrating activity, or an antigen binding fragment of 3E10 or said 3E10 variant. Additionally, the antibody or antigen binding fragment thereof may be an antibody that binds to the same epitope as 3E10, or an antibody that has substantially the same cell penetrating activity as 3E10, or an antigen binding fragment thereof. These are exemplary of agents that target ENT2. In certain embodiments, the antigen binding fragment is an Fv or scFv fragment thereof. Monoclonal antibody 3E10 can be produced by a hybridoma 3E10 placed permanently on deposit with the American Type Culture Collection (ATCC) under ATCC accession number PTA-2439 and is disclosed in U.S. Pat. No. 7,189,396. Additionally or alternatively, the 3E10 antibody can be produced by expressing in a host cell nucleotide sequences encoding the heavy and light chains of the 3E10 antibody. The term "3E10 antibody" or "monoclonal antibody 3E10" are used to refer to the antibody, regardless of the method used to produce the antibody. Similarly, when referring to variants or antigen-binding fragments of 3E10, such terms are used without reference to the manner in which the antibody was produced. At this point, 3E10 is generally not produced by the hybridoma but is produced recombinantly. Thus, in the context of the present application, 3E10 antibody will refer to an antibody comprising a variable heavy chain domain (VH; heavy chain variable domain) comprising the amino acid sequence set forth in SEQ ID NO: 13 and the variable light chain domain (VL; light chain variable domain) comprising the amino acid sequence set forth in SEQ ID NO: 14.

The internalizing moiety may also comprise variants of mAb 3E10, such as variants of 3E10 which retain the same cell penetration characteristics as mAb 3E10, as well as variants modified by mutation to improve the utility thereof (e.g., improved ability to target specific cell types, improved ability to penetrate the cell membrane, improved ability to localize to the cellular DNA, convenient site for conjugation, and the like). Such variants include variants wherein one or more conservative substitutions are introduced into the heavy chain, the light chain and/or the constant region(s) of the antibody. Such variants include humanized versions of 3E10 or a 3E10 variant. In some embodiments, the light chain or heavy chain may be modified at the N-terminus or C-terminus. Moreover, the antibody or antibody fragment may be modified to facilitate conjugation to an antisense oligonucleotide. Similarly, the foregoing description of variants applies to antigen binding fragments. Any of these antibodies, variants, or fragments may be made recombinantly by expression of the nucleotide sequence(s) in a host cell.

Monoclonal antibody 3E10 has been shown to penetrate cells to deliver proteins and nucleic acids into the cytoplasmic or nuclear spaces of target tissues (Weisbart R H et al., J Autoimmun. 1998 October; 11(5):539-46; Weisbart R H, et al. Mol Immunol. 2003 March; 39(13):783-9; Zack D J et al., J Immunol. 1996 Sep. 1; 157(5):2082-8.). Further, the VH and Vk sequences of 3E10 are highly homologous to human antibodies, with respective humanness z-scores of 0.943 and −0.880. Thus, Fv3E10 is expected to induce less of an anti-antibody response than many other approved humanized antibodies (Abhinandan K R et al., Mol. Biol. 2007 369, 852-862). A single chain Fv fragment of 3E10 possesses all the cell penetrating capabilities of the original monoclonal antibody, and proteins such as catalase, dystrophin, HSP70 and p53 retain their activity following conjugation to Fv3E10 (Hansen J E et al., Brain Res. 2006 May 9; 1088(1):187-96; Weisbart R H et al., Cancer Lett. 2003 Jun. 10; 195(2):211-9; Weisbart R H et al., J Drug Target. 2005 February; 13(2):81-7; Weisbart R H et al., J Immunol. 2000 Jun. 1; 164(11):6020-6; Hansen J E et al., J Biol Chem. 2007 Jul. 20; 282(29):20790-3). The 3E10 is built on the antibody scaffold present in all mammals; a mouse variable heavy chain and variable kappa light chain. 3E10 gains entry to cells via the ENT2 nucleotide transporter that is particularly enriched in skeletal muscle and cancer cells, and in vitro studies have shown that 3E10 is nontoxic. (Weisbart R H et al., Mol Immunol. 2003 March; 39(13):783-9; Pennycooke M et al., Biochem Biophys Res Commun. 2001 Jan. 26; 280(3):951-9).

The internalizing moiety may also include mutants of mAb 3E10, such as variants of 3E10 which retain the same or substantially the same cell penetration characteristics as mAb 3E10, as well as variants modified by mutation to improve the utility thereof (e.g., improved ability to target specific cell types, improved ability to penetrate the cell membrane, improved ability to localize to the cellular DNA, improved binding affinity, and the like). Such mutants include variants wherein one or more conservative substitutions are introduced into the heavy chain, the light chain and/or the constant region(s) of the antibody. Numerous variants of mAb 3E10 have been characterized in, e.g., U.S. Pat. No. 7,189,396 and WO 2008/091911, the teachings of which are incorporated by reference herein in their entirety.

In certain embodiments, the internalizing moiety comprises an antibody or antigen binding fragment comprising an VH domain comprising an amino acid sequence at least 80%, 85%, 90%, 95%, 96%, 97%, 99%, or 100% identical to SEQ ID NO: 13 and/or a VL domain comprising an amino acid sequence at least 85%, 90%, 95%, 96%, 97%, 99%, or 100% identical to SEQ ID NO: 14. Of course, such internalizing moieties transit cells via ENT2 and/or bind the same epitope as 3E10.

In certain embodiments, the internalizing moiety is an antigen binding fragment, such as a single chain Fv of 3E10 (scFv) comprising SEQ ID NOs: 13 and 14). In certain embodiments, the internalizing moiety comprises a single chain Fv of 3E10 (or another antigen binding fragment), and the amino acid sequence of the $V_H$ domain is at least 90%, 95%, 96%, 97%, 98%, 99%, or 100% identical to SEQ ID NO: 13, and amino acid sequence of the $V_L$ domain is at least 90%, 95%, 96%, 97%, 98%, 99%, or 100% identical to SEQ ID NO: 14. The variant 3E10 or fragment thereof retains the function of an internalizing moiety.

In certain embodiments, the internalizing moiety comprises at least 1, 2, 3, 4, or 5 of the CDRs of 3E10 (e.g., which are set forth in SEQ ID NOs: 16-21. In certain embodiments, the internalizing moiety comprises all six CDRs of 3E10 (e.g., comprises SEQ ID NOs 16-21). For any of the foregoing, in certain embodiments, the internalizing moiety is an antibody that binds the same epitope as 3E10 and/or the internalizing moiety competes with 3E10 for binding to antigen. Exemplary internalizing moieties target and transit cells via ENT2.

The present disclosure utilizes the cell penetrating ability of 3E10 or 3E10 fragments or variants to promote delivery of antisense oligonucleotides and/or MBNL1 in vivo. 3E10 and 3E10 variants and fragments are particularly well suited for this because of their demonstrated ability to effectively promote delivery to muscle cells, including skeletal and cardiac muscle, as well as diaphragm. Thus, 3E10 and 3E10 variants and fragments are especially useful for promoting effective delivery into cells in subjects, such as human patients or model organisms, having DM1 or symptoms that recapitulate DM1.

As described further below, a recombinant 3E10 or 3E10-like variant or fragment can be conjugated, linked or otherwise joined to an antisense oligonucleotide or an MBNL1 polypeptide. Methods of chemically conjugating antisense oligonucleotides to proteins are well known in the art and include, addition of a free cysteine to the C-terminus of, for example, an scFv or other antigen-binding fragment to generate a site for site-directed conjugation. In the context of making chimeric polypeptides to MBNL1, chemical conjugation, as well as making the chimeric polypeptide as a fusion protein is available and known in the art.

Preparation of antibodies or fragments thereof (e.g., a single chain Fv fragment encoded by $V_H$-linker-$V_L$ or $V_L$-linker-$V_H$) is well known in the art. In particular, methods of recombinant production of mAb 3E10 antibody fragments have been described in WO 2008/091911. Further, methods of generating scFv fragments of antibodies are well known in the art. When recombinantly producing an antibody or antibody fragment, a linker may be used. For example, typical surface amino acids in flexible protein regions include Gly, Asn and Ser. One exemplary linker is provided in SEQ ID NO: 15. Permutations of amino acid sequences containing Gly, Asn and Ser would be expected to satisfy the criteria (e.g., flexible with minimal hydrophobic or charged character) for a linker sequence. Another exemplary linker is of the formula $(G_4S)n$, wherein n is an integer from 1-10, such as 2, 3, or 4. Other near neutral amino acids, such as Thr and Ala, can also be used in the linker sequence.

In addition to linkers interconnecting portions of, for example, an scFv, the disclosure contemplates the use of additional linkers to, for example, interconnect the antisense oligonucleotide to the antibody portion of the antisense conjugate or to interconnect the MBNL1 portion to the antibody portion of the chimeric polypeptide.

Preparation of antibodies may be accomplished by any number of well-known methods for generating monoclonal antibodies. These methods typically include the step of immunization of animals, typically mice, with a desired immunogen (e.g., a desired target molecule or fragment thereof). Once the mice have been immunized, and preferably boosted one or more times with the desired immunogen(s), monoclonal antibody-producing hybridomas may be prepared and screened according to well known methods (see, for example, Kuby, Janis, *Immunology*, Third Edition, pp. 131-139, W.H. Freeman & Co. (1997), for a general overview of monoclonal antibody production, that portion of which is incorporated herein by reference). Over the past several decades, antibody production has become extremely robust. In vitro methods that combine antibody recognition and phage display techniques allow one to amplify and select antibodies with very specific binding capabilities. See, for example, Holt, L. J. et al., "The Use of Recombinant Antibodies in Proteomics," *Current Opinion in Biotechnology*, 2000, 11:445-449, incorporated herein by reference. These methods typically are much less cumbersome than preparation of hybridomas by traditional monoclonal antibody preparation methods. In one embodiment, phage display technology may be used to generate an internalizing moiety specific for a desired target molecule. An immune response to a selected immunogen is elicited in an animal (such as a mouse, rabbit, goat or other animal) and the response is boosted to expand the immunogen-specific B-cell population. Messenger RNA is isolated from those B-cells, or optionally a monoclonal or polyclonal hybridoma population. The mRNA is reverse-transcribed by known methods using either a poly-A primer or murine immunoglobulin-specific primer(s), typically specific to sequences adjacent to the desired $V_H$ and $V_L$ chains, to yield cDNA. The desired $V_H$ and $V_L$ chains are amplified by polymerase chain reaction (PCR) typically using $V_H$ and $V_L$ specific primer sets, and are ligated together, separated by a linker. $V_H$ and $V_L$ specific primer sets are commercially available, for instance from Stratagene, Inc. of La Jolla, Calif. Assembled $V_H$-linker-$V_L$ product (encoding an scFv fragment) is selected for and amplified by PCR. Restriction sites are introduced into the ends of the $V_H$-linker-$V_L$ product by PCR with primers including restriction sites and the scFv fragment is inserted into a suitable expression vector (typically a plasmid) for phage display. Other fragments, such as an Fab' fragment, may be cloned into phage display vectors for surface expression on phage particles. The phage may be any phage, such as lambda, but typically is a filamentous phage, such as fd and M13, typically M13.

In certain embodiments, an antibody or antibody fragment is made recombinantly in a host cell. In other words, once the sequence of the antibody is known (for example, using the methods described above), the antibody can be made recombinantly using standard techniques.

In certain embodiments, the internalizing moieties may be modified to make them more resistant to cleavage by proteases. For example, the stability of an internalizing moiety comprising a polypeptide may be increased by substituting one or more of the naturally occurring amino acids in the (L) configuration with D-amino acids. In various embodiments, at least 1%, 5%, 10%, 20%, 50%, 80%, 90% or 100% of the amino acid residues of internalizing moiety may be of the D configuration. The switch from L to D amino acids neutralizes the digestion capabilities of many of the ubiquitous peptidases found in the digestive tract. Alternatively, enhanced stability of an internalizing moiety comprising an peptide bond may be achieved by the introduction of modifications of the traditional peptide linkages. For example, the introduction of a cyclic ring within the polypeptide backbone may confer enhanced stability in order to circumvent the effect of many proteolytic enzymes known to digest polypeptides in the stomach or other digestive organs and in serum. In still other embodiments, enhanced stability of an internalizing moiety may be achieved by intercalating one or more dextrorotatory amino acids (such as, dextrorotatory phenylalanine or dextrorotatory tryptophan) between the amino acids of internalizing moiety. In exemplary embodiments, such modifications increase the protease resistance of an internalizing moiety without affecting the activity or specificity of the interaction with a desired target molecule.

II. Antisense Oligonucleotides

The disclosure provides antisense conjugates comprising an antisense oligonucleotide. Various features of antisense oligonucleotides useful in the context of the present disclosure are described herein. It should be noted that, when describing functional properties of an antisense oligonucleotide, such properties can also be used to describe an antisense conjugate. Accordingly, any description of a functional or structural property of an antisense oligonucleotide may, in certain embodiments, be used to describe an antisense conjugate of the disclosure.

Suitable antisense oligonucleotides, including conjugates comprising antisense oligonucleotides, hybridize to DNA, e,g, a DNA molecule encoding DMPK, such as a CUG-expanded DMPK gene. Other suitable antisense oligonucleotides, including conjugates comprising antisense oligonucleotides, hybridize to RNA, e,g, an RNA transcript of DMPK, such as an expanded or non-expanded transcript of DMPK. In certain embodiments, the antisense oligonucleotides (including when present as part of a conjugate) hybridize to a 3'UTR of a DMPK transcript, such as one or more CUG repeats in the 3'UTR. In certain embodiments, the antisense oligonucleotides (including when present as part of a conjugate) hybridize to coding sequence of the DMPK transcript (e.g., SEQ ID NOs: 24-27). In some embodiments, the antisense oligonucleotides selectively bind to DMPK transcript, e.g., to a 3'UTR of a transcript comprising the sequence of any one of SEQ ID NOs: 24-27. In some embodiments, the antisense oligonucleotides selectively bind to DMPK transcripts having expanded CUG repeats (>50 CUG repeats).

It should be understood throughout that when describing properties of antisense oligonucleotides, including ability to hybridize to DMPK, the disclosure contemplates that such description may be used in describing antisense oligonucleotides provided alone and/or provided as a conjugate.

Without being bound by theory, the specific hybridization of an antisense molecule (e.g., an antisense oligonucleotide) of the present disclosure with an RNA molecule, e.g., CUG-expanded DMPK, may alter the processing of the RNA or alter the physical and/or chemical interactions between the RNA and another protein or nucleic acid molecule. For example, the specific hybridization of the antisense molecules of the present disclosure with the CUG-expanded DMPK RNA may alter the degradation of the DMPK RNA, including by RNaseH-mediated degradation, the splicing patterns of DMPK RNA, or may prevent proteins (e.g. MBNL1) or nucleic acids from binding to the RNA, or may liberate a nucleic acid or protein (e.g. MBNL1) bound to the CUG-expanded DMPK RNA. Regardless of the particular mechanism of action, antisense oligonucleotide conjugates have utility in studying DMPK and myotonic dystrophy, in vitro and in animal models. Moreover, regardless of the particular mechanism of action, antisense conjugates have utility in treating (ameliorating one or more symptoms of) myotonic dystrophy. In addition, the conjugates of the disclosure promote delivery of the antisense oligonucleotide into cells, including into muscle cells.

In some embodiments, the antisense molecules are designed such that they target a region that includes the start codon (AUG in RNA and ATG in DNA) or the stop codon(s) (UAA, UAG and UGA in RNA and TAA, TAG and TGA in DNA). In some embodiments, the antisense molecules are designed such that they target a region within 50 nucleotides of the start or stop codons. In some embodiments, the antisense molecules of the present disclosure target a region that includes a portion of the open reading frame (ORF) of a DNA or RNA molecule, e.g., the ORF of DMPK DNA or RNA, including the ORF of a CUG-expanded DMPK DNA or RNA. The ORF includes the region of the RNA between the start and stop codons. In some embodiments, the antisense molecules are designed such that they bind to coding regions of the DNA or RNA (i.e., exons) and/or non-coding regions of the DNA or RNA (i.e., introns). In some embodiments, the antisense molecules are designed such that they bind to splice signals, such as to intron-exon junctions. In certain embodiments of any of the foregoing, the antisense oligonucleotide hybridizes to RNA of DMPK, wildtype and/or CUG expanded. It should be noted that, depending on what portion of the DNA or RNA the oligonucleotide is designed to hybridize to, many such molecules will be capable of hybridizing to both wildtype and CUG-expanded DMPK. However, other oligonucleotides may bind preferentially to CUG-expanded DMPK versus wildtype DMPK. In certain embodiments, an antisense conjugate of the disclosure hybridizes preferentially to CUG-expanded DMPK versus wildtype DMPK.

In some embodiments, the antisense molecules are designed such that they target a region of RNA that includes the 5' UTR or the 3' UTR. The 5' UTR includes untranslated sequences that may include, for example, regulatory sequences (e.g., iron response element sequences, introns or riboswitches) and/or the 5' methylguanylate cap. The 3' UTR may include sequences such as a poly-adenylation signal, binding sequences for proteins (e.g. SECIS elements or AU-rich elements) or binding sequences for miRNAs.

In some embodiments, the antisense molecules hybridize to DMPK RNA, such as CUG-expanded DMPK (e.g., mutant DMPK), in such a way that the antisense molecules prevent binding of the RNA to another protein. For example, the antisense molecules may hybridize to the DMPK RNA such that the RNA is incapable of binding to MBNL1 protein. For example, the antisense molecules may compete with MBNL1 for the same binding site on an RNA molecule, e.g., a "YGCY" motif, in which "Y" is a pyrimidine (Goers, E S, 2010, Nucl. Acids Res., 38(7): 2467-84).

In certain preferred embodiments, the antisense molecules hybridize to RNA molecules that carry an excess (>50) of CUG or CCUG repeats. For example, the antisense molecules may bind to CUG-expanded (e.g., mutant) DMPK RNA having excess CUG or CCUG repeats. In some embodiments, the antisense molecules hybridize to one or more of CUG repeats, CAG repeats, CCUG, CCG or CGG repeats.

The antisense oligonucleotides of the present disclosure hybridize to RNA or DNA via one or more regions of complementary nucleoside or nucleotide bases. "Complementary," is the capacity for specific pairing between two nucleotides, e.g., between adenine and thymine, between adenine and uracil, and between guanine and cytosine. However, the skilled worker would understand that an antisense oligonucleotide need not be 100% complementary to that of its target nucleic acid in order to hybridize with that target DNA or RNA molecule. An antisense compound is capable of hybridizing with a target DNA molecule when it binds to the target molecule to such an extent that it interferes with the transcription of that DNA molecule. An antisense compound is capable of hybridizing with a target RNA molecule, e.g., a mutant DMPK RNA, when it binds to the RNA molecule to such an extent that it alters the pre-existing state of the RNA molecule in a cell. For example, the antisense compound is capable of hybridizing with a target RNA molecule, e.g., a mutant DMPK RNA, when it binds to the RNA molecule to such an extent that it causes the degradation of the RNA molecule by an enzyme such as RNaseH, or it alters (i.e., induces or inhibits) the splicing of the RNA molecule, or it interacts with the RNA molecule in such a way that it prevents the binding of proteins or nucleic acids to the RNA molecule (e.g. MBNL1), or it interacts with the RNA molecule in such a way that it liberates proteins previously bound to the RNA molecule (e.g. MBNL1).

In some embodiments, the antisense molecule (e.g., the antisense oligonucleotide portion of the antisense conjugate) is 8-50 nucleotides in length. In other embodiments, the antisense molecule is 12-35 nucleotides in length. In other embodiments, the antisense molecule is 12-30 nucleotides in length. In other embodiments, the antisense molecule is 14-25 nucleotides in length. In other embodiments, the antisense oligonucleotide comprises 14-30, 14-25, 14-20, 14-18, 14-17, 15-30, 15-25, 15-20, 15-18, 16-30, 16-25, 16-20, 16-18, 17-30, 17-25, 17-20, or 17-18 nucleotides. In other embodiments, the antisense oligonucleotide comprises or consists of 14, 15, 16, 17, 18, 19, 20, 21, 22, 23, 24, 25, 26, 27, 28, 29, 30, 31, 32, 33, 34, 35, 36, 37, 38, 39, or 40 nucleotides. In some embodiments, the antisense oligonucleotide comprises the primary nucleotide sequence set forth in any of SEQ ID NOs: 9-12 or 22-23. For example, the disclosure provides a conjugate comprising the nucleotide sequence set forth in any of SEQ ID NOs: 9-12 or 22-23. In other embodiments, the disclosure provides an antisense conjugate comprising an antisense oligonucleotide portion, wherein the antisense oligonucleotide portion comprises or consists of the nucleotide sequence set forth in any of SEQ ID NOs: 9-12 or 22-23. In other embodiments, the antisense oligonucleotide comprises a nucleotide sequence that hybridizes under stringent hybridization conditions of at least 0.2×SSC at 65 C to a DMPK RNA transcript (coding or non-coding region), such as a transcript that encodes a DMPK protein comprising the amino acid sequence set forth in SEQ ID NO: 8 or any of the transcripts of SEQ ID NOs: 24-27.

The antisense oligonucleotides of the present disclosure are oligomers or polymers of ribonucleic acid (RNA) or deoxyribonucleic acid (DNA) or mimetics thereof, or combinations of any of the foregoing. The antisense oligonucleotides may include oligonucleotides that are composed of naturally-occurring nucleobases, sugars and covalent internucleoside (backbone) linkages as well as oligonucleotides having non-naturally-occurring nucleobases, sugars and covalent internucleoside (backbone) linkages. Non-naturally-occurring portions of the antisense molecules may be preferred, as these portions may endow the antisense molecules with desirable properties such as, for example, enhanced affinity for nucleic acid target and increased stability in the presence of nucleases. Throughout the disclosure, a nucleotide having any non-naturally occurring portion is referred to as a modified nucleotide (and the term modified nucleotide is used for convenience, including when such modification alters the structure of the nucleotide so that is technically no longer a nucleotide, e.g., it is a nucleic acid or nucleoside).

Nucleosides are base-sugar combinations. Normally, the base portion of a nucleoside is a heterocyclic base, e.g., a purine or a pyrimidines base. Nucleotides are nucleosides that further include a phosphate group covalently linked to the sugar portion of the nucleoside. For those nucleosides that include a pentofuranosyl sugar, the phosphate group can be linked to either the 2', 3' or 5' hydroxyl moiety of the sugar. In forming oligonucleotides, the phosphate groups covalently link adjacent nucleosides to one another to form a linear polymeric compound. In turn the respective ends of this linear polymeric structure can be further joined to form a circular structure. Within the oligonucleotide structure, the phosphate groups are commonly referred to as forming the internucleoside backbone of the oligonucleotide. The normal linkage or backbone of RNA and DNA is a 3' to 5' phosphodiester linkage.

In some embodiments, the antisense oligonucleotides of the present disclosure include oligonucleotides containing modified backbones or non-natural internucleoside linkages. In some embodiments, the oligonucleotides having modified backbones include those that retain a phosphorus atom in the backbone. In other embodiments, the oligonucleotides having modified backbones include those that do not have a phosphorus atom in the backbone.

In some embodiments, modified oligonucleotide backbones that do not include a phosphorus atom therein have backbones that are formed by short chain alkyl or cycloalkyl internucleoside linkages, mixed heteroatom and alkyl or cycloalkyl internucleoside linkages, or one or more short chain heteroatomic or heterocyclic internucleoside linkages. These include those having morpholino linkages (formed in part from the sugar portion of a nucleoside); siloxane backbones; sulfide, sulfoxide and sulfone backbones; formacetyl and thioformacetyl backbones; methylene formacetyl and thioformacetyl backbones; riboacetyl backbones; alkene containing backbones; sulfamate backbones; methyleneimino and methylenehydrazino backbones; sulfonate and sulfonamide backbones; amide backbones; and others having mixed N, O, S and $CH_2$ component parts.

In some embodiments of the present disclosure, the oligonucleotide backbone includes, for example, phosphorothioates, chiral phosphorothioates, phosphorodithioates, phosphotriesters, aminoalkylphosphotriesters, methyl and other alkyl phosphonates including 3'-alkylene phosphonates, 5'-alkylene phosphonates and chiral phosphonates, phosphinates, phosphoramidates including 3'-amino phosphoramidate and aminoalkylphosphoramidates, thionophosphoramidates, thionoalkylphosphonates, thionoalkylphosphotriesters, selenophosphates and boranophosphates having normal 3'-5' linkages, 2'-5' linked analogs of these, and those having inverted polarity wherein one or more internucleotide linkages is a 3' to 3', 5' to 5' or 2' to 2' linkage.

Representative United States patents that teach the preparation of the above phosphorus-containing linkages include, but are not limited to, U.S. Pat. Nos. 3,687,808; 4,469,863; 4,476,301; 5,023,243; 5,177,196; 5,188,897; 5,264,423; 5,276,019; 5,278,302; 5,286,717; 5,321,131; 5,399,676; 5,405,939; 5,453,496; 5,455,233; 5,466,677; 5,476,925; 5,519,126; 5,536,821; 5,541,306; 5,550,111; 5,563,253; 5,571,799; 5,587,361; 5,194,599; 5,565,555; 5,527,899; 5,721,218; 5,672,697 and 5,625,050.

In some embodiments, in modified oligonucleotide, both the sugar and the internucleoside linkage, i.e., the backbone, of the nucleotide units are replaced with novel groups. The base units are maintained for hybridization with an appropriate nucleic acid target compound. One such oligomeric compound, an oligonucleotide mimetic that has been shown to have excellent hybridization properties, is referred to as a peptide nucleic acid (PNA). In PNA compounds, the sugar-backbone of an oligonucleotide is replaced with an amide containing backbone, in particular an aminoethylglycine backbone. The nucleobases are retained and are bound directly or indirectly to aza nitrogen atoms of the amide portion of the backbone. Representative United States patents that teach the preparation of PNA nucleotides include, but are not limited to, U.S. Pat. Nos. 5,539,082; 5,714,331; and 5,719,262, each of which is herein incorporated by reference. Further teaching of PNA nucleotides can be found in Nielsen et al., Science, 1991, 254, 1497-1500.

In some embodiments of the present disclosure are oligonucleotides with phosphorothioate backbones and oligonucleosides with heteroatom backbones, such as —$CH_2$—NH—O—$CH_2$—, —$CH_2$—N($CH_3$)—O—$CH_2$-[known as a methylene (methylimino) or MMI backbone], —$CH_2$—O—N($CH_3$)—$CH_2$—, —$CH_2$—N($CH_3$)—N($CH_3$)—$CH_2$— and —O—N($CH_3$)—$CH_2$—$CH_2$— [wherein the native phosphodiester backbone is represented as —O—P(=O)(OH)—O—$CH_2$—], and the amide backbones of the above referenced U.S. Pat. No. 5,602,240, or the morpholino backbone structures of the above-referenced U.S. Pat. No. 5,034,506.

Modified oligonucleotides may also contain one or more substituted sugar moieties. In some embodiments, the oligonucleotides comprise one of the following at the 2' position: OH; F; O-, S-, or N-alkyl; O-, S-, or N-alkenyl; O-, S- or N-alkynyl; or O-alkyl-O-alkyl, wherein the alkyl, alkenyl and alkynyl may be substituted or unsubstituted $C_1$ to $C_{10}$ alkyl or $C_2$ to $C_{10}$ alkenyl and alkynyl. In particular embodiments, the oligonucleotides comprise O[($CH_2$)$_n$O]$_m$ $CH_3$, O($CH_2$)$_n$OCH$_3$, O($CH_2$)$_n$NH$_2$, O($CH_2$)$_n$CH$_3$, O($CH_2$)$_n$ONH$_2$, and O($CH_2$)$_n$ON[($CH_2$)$_n$CH$_3$)]$_2$, where n and m are from 1 to about 10. In other embodiments, oligonucleotides comprise one of the following at the 2' position: $C_1$ to $C_{10}$ lower alkyl, substituted lower alkyl, alkenyl, alkynyl, alkaryl, aralkyl, O-alkaryl or O-aralkyl, SH, SCH$_3$, OCN, Cl, Br, CN, CF$_3$, OCF$_3$, SOCH$_3$, SO$_2$CH$_3$, ONO$_2$, NO$_2$, N$_3$, NH$_2$, heterocycloalkyl, heterocycloalkaryl, aminoalkylamino, polyalkylamino, substituted silyl, an RNA cleaving group, a reporter group, an intercalator, a group for improving the pharmacokinetic properties of an oligonucleotide, or a group for improving the pharmacodynamic properties of an oligonucleotide, and other substituents having similar properties. Other embodiments include antisense molecules comprising 2'-dimethylaminooxyethoxy, i.e., a O($CH_2$)$_2$ON(CH$_3$)$_2$ group, also known as 2'-DMAOE or 2'-dimethylaminoethoxyethoxy (also known in the art as 2'-O-dimethylaminoethoxyethyl or 2'-DMAEOE), i.e., 2'-O—CH$_2$—O—CH$_2$—N(CH$_2$)$_2$.

In some embodiments, the antisense oligonucleotides of the present disclosure includes an alkoxyalkoxy group, e.g., 2'-methoxyethoxy (2'-O—CH$_2$CH$_2$OCH$_3$, also known as 2'-O-(2-methoxyethyl) or 2'-MOE) (Martin et al., Helv. Chim. Acta, 1995, 78, 486-504). In one embodiment, the antisense oligonucleotides of the present disclosure include 2'-MOE. In some embodiments, the antisense oligonucleotides comprise 1-10 MOE nucleotides. In other embodiments, the antisense oligonucleotides comprise 2-7 MOE nucleotides. In other embodiments, the antisense oligonucleotides comprise 3-6 MOE nucleotides.

In some embodiments, the antisense oligonucleotides of the present disclosure include a nucleotide analog having a constrained furanose ring conformation, such as Locked Nucleic Acids (LNAs). In LNAs, a 2'-hydroxyl group is linked to the 3' or 4' carbon atom of the sugar ring thereby forming a bicyclic sugar moiety. In some embodiments, the linkage in the LNA is a methelyne (—CH$_2$—)$_n$group bridging the 2' oxygen atom and the 4' carbon atom wherein n is 1 or 2. LNAs and preparation thereof are described in WO 98/39352 and WO 99/14226. In some embodiments, the antisense oligonucleotides comprise 1-10 LNA nucleotides. In other embodiments, the antisense molecules comprise 2-7 LNA nucleotides. In other embodiments, the antisense molecules comprise 3-6 LNA nucleotides.

In other embodiments of the antisense oligonucleotides of the present disclosure, modifications to the antisense molecules include 2'-methoxy (2'-O—CH$_3$), 2'-aminopropoxy (2'-OCH$_2$CH$_2$CH$_2$NH$_2$), 2'-allyl(2'-CH$_2$—CH=CH$_2$), 2'-O-allyl(2'-O—CH$_2$—CH=CH$_2$) and 2'-fluoro (2'-F). The 2'-modification may be in the arabino (up) position or ribo (down) position. An example of a 2'-arabino modification is 2'-F. Similar modifications may also be made at other positions on the oligonucleotide, particularly the 3' position of the sugar on the 3' terminal nucleotide or in 2'-5' linked oligonucleotides and the 5' position of 5' terminal nucleotide. Oligonucleotides may also have sugar mimetics such as cyclobutyl moieties in place of the pentofuranosyl sugar. Representative United States patents that teach the preparation of such modified sugar structures include, but are not limited to, U.S. Pat. Nos. 4,981,957; 5,118,800; 5,319,080; 5,359,044; 5,393,878; 5,446,137; 5,466,786; 5,514,785; 5,519,134; 5,567,811; 5,576,427; 5,591,722; 5,597,909; 5,610,300; 5,627,053; 5,639,873; 5,646,265; 5,658,873; 5,670,633; 5,792,747; and 5,700,920.

The antisense oligonucleotides of the present disclosure may also include nucleobase (often referred to in the art simply as "base") modifications or substitutions. An "unmodified" or "natural" nucleobase, as used herein, includes the purine bases adenine (A) and guanine (G), and the pyrimidine bases thymine (T), cytosine (C) and uracil (U). Modified nucleobases include other synthetic and natural nucleobases such as 5-methylcytosine (5-me-C), 5-hydroxymethyl cytosine, xanthine, hypoxanthine, 2-aminoadenine, 6-methyl and other alkyl derivatives of adenine and guanine, 2-propyl and other alkyl derivatives of adenine and guanine, 2-thiouracil, 2-thiothymine and 2-thiocytosine, 5-halouracil and cytosine, 5-propynyl uracil and cytosine and other alkynyl derivatives of pyrimidine bases, 6-azo uracil, cytosine and thymine, 5-uracil (pseudouracil), 4-thiouracil, 8-halo, 8-amino, 8-thiol, 8-thioalkyl, 8-hydroxyl and other 8-substituted adenines and guanines, 5-halo particularly 5-bromo, 5-trifluoromethyl and other 5-substituted uracils and cytosines, 7-methylguanine and 7-methyladenine, 2-F-adenine, 2-amino-adenine, 8-azaguanine and 8-azaadenine, 7-deazaguanine and 7-deazaadenine and 3-deazaguanine and 3-deazaadenine. Further modified nucleobases include tricyclic pyrimidines such as phenoxazine cytidine (1H-pyrimido[5,4-b][1,4]benzoxazin-2(3H)-one), phenothiazine cytidine (1H-pyrimido[5,4-b][1,4]benzothiazin-2(3H)-one), G-clamps such as a substituted phenoxazine cytidine (e.g. 9-(2-aminoethoxy)-H-pyrimido[5,4-b][1,4]benzoxazin-2(3H)-one), carbazole cytidine (2H-pyrimido[4,5-b]indol-2-one), pyridoindole cytidine (H-pyrido[3',2':4,5]pyrrolo[2,3-d]pyrimidin-2-one). Modified nucleobases may also include those in which the purine or pyrimidine base is replaced with other heterocycles, for example 7-deaza-adenine, 7-deazaguanosine, 2-aminopyridine and 2-pyridone. Further nucleobases include those disclosed in U.S. Pat. No. 3,687,808, those disclosed in The Concise Encyclopedia Of Polymer Science And Engineering, pages 858-859, Kroschwitz, J. I., ed. John Wiley & Sons, 1990, those disclosed by Englisch et al., Angewandte Chemie, International Edition, 1991, 30, 613, and those disclosed by Sanghvi, Y. S., Chapter 15, Antisense Research and Applications, pages 289-302, Crooke, S. T. and Lebleu, B., ed., CRC Press, 1993. Certain of these nucleobases are particularly useful for increasing the binding affinity of the oligomeric compounds of the disclosure. These include 5-substituted pyrimidines, 6-azapyrimidines and N-2, N-6 and O-6 substituted purines, including 2-aminopropyladenine, 5-propynyluracil and 5-propynylcytosine. 5-methylcytosine substitutions have been shown to increase nucleic acid duplex stability by 0.6-1.2° C. (Sanghvi, Y. S., Crooke, S. T. and Lebleu, B., eds., Antisense Research and Applications, CRC Press, Boca Raton, 1993, pp. 276-278).

Representative United States patents that teach the preparation of certain of the above noted modified nucleobases as well as other modified nucleobases include, but are not limited to, the above noted U.S. Pat. No. 3,687,808, as well as U.S. Pat. Nos. 4,845,205; 5,130,302; 5,134,066; 5,175,273; 5,367,066; 5,432,272; 5,457,187; 5,459,255; 5,484,908; 5,502,177; 5,525,711; 5,552,540; 5,587,469; 5,594,121; 5,596,091; 5,614,617; 5,645,985; 5,830,653; 5,763,588; 6,005,096; and 5,681,941.

It is not necessary for all positions in a given compound to be uniformly modified, and in fact more than one of the aforementioned modifications may be incorporated in a single compound or even at a single nucleoside within an oligonucleotide. The present disclosure also includes antisense oligonucleotides which are chimeric compounds. "Chimeric" antisense compounds or "chimeras," in the context of this disclosure, are antisense compounds, particularly oligonucleotides, which contain two or more chemically distinct regions, each made up of at least one monomer unit, i.e., a nucleotide in the case of an oligonucleotide compound. These oligonucleotides typically contain at least one region wherein the oligonucleotide is modified so as to confer upon the oligonucleotide increased resistance to nuclease degradation, increased cellular uptake, and/or increased binding affinity for the target nucleic acid. An additional region of the oligonucleotide may serve as a substrate for enzymes capable of cleaving RNA:DNA or RNA:RNA hybrids. By way of example, RNase H is a cellular endonuclease which cleaves the RNA strand of an RNA:DNA duplex. Activation of RNase H, therefore, results in cleavage of the RNA target, thereby greatly enhancing the efficiency of oligonucleotide inhibition of gene expression. Consequently, comparable results can often be obtained with shorter oligonucleotides when chimeric oligonucleotides are used, compared to phosphorothioate deoxyoligonucleotides hybridizing to the same target region. Cleavage of the RNA target can be routinely detected by gel electrophoresis and, if necessary, associated nucleic acid hybridization techniques known in the art.

Chimeric antisense oligonucleotides of the disclosure may be formed as composite structures of two or more oligonucleotides, modified oligonucleotides, oligonucleosides and/or oligonucleotide mimetics as described above. Such compounds have also been referred to in the art as hybrids or gapmers. Representative United States patents that teach the preparation of such hybrid structures include, but are not limited to, U.S. Pat. Nos. 5,013,830; 5,149,797; 5,220,007; 5,256,775; 5,366,878; 5,403,711; 5,491,133; 5,565,350; 5,623,065; 5,652,355; 5,652,356; and 5,700,922.

A "gapmer" is defined as an oligomeric compound, generally an oligonucleotide, having a 2'-deoxyoligonucleotide region flanked by non-deoxyoligonucleotide segments. The central region is referred to as the "gap." The flanking segments are referred to as "wings." While not wishing to be bound by theory, the gap of the gapmer presents a substrate recognizable by RNaseH when bound to the RNA target whereas the wings do not provide such a substrate but can confer other properties such as contributing to duplex stability or advantageous pharmacokinetic effects. Each wing can be one or more non-deoxyoligonucleotide monomers (if one of the wings has zero non-deoxyoligonucleotide monomers, a "hemimer" is described). In one embodiment, the gapmer is a ten deoxyribonucleotide gap flanked by five non-deoxyribonucleotide wings. This is referred to as a 5-10-5 gapmer. In other embodiments, the gapmer is an eight deoxyribonucleotide gap flanked by three non-deoxyribonucleotide wings. This is referred to as a 3-8-3 gapmer. In other embodiments, the gapmer is a ten deoxyribonucleotide gap flanked by three non-deoxyribonucleotide wings. This is referred to as a 3-10-3 gapmer. Other configurations are readily recognized by those skilled in the art, such as a 3-7-3 gapmer.

In some embodiments, the gapmer described above comprises LNA and MOE nucleotides. In some embodiments, the gapmer comprises 1-10 LNA and/or MOE nucleotides. In some embodiments, the gapmer comprises 2-7 LNA and/or MOE nucleotides. In other embodiments, the gapmer comprises 3-6 MOE and/or LNA nucleotides. In some embodiments the flanking blocks of ribonucleotides comprise LNA and/or MOE nucleotides.

In some embodiments, the gapmers described above induce RNase H degradation of the target RNA nucleotide, e.g., the mutant DMPK RNA molecule. In other embodiments, the gapmers induce degradation of the target RNA nucleotide, e.g., the mutant DMPK RNA molecule by means of an RNase H-independent pathway. In some embodiments, the gapmers prevents the binding of a protein, e.g. MBNL1, to a DNA or RNA sequence, e.g., mutant DMPK RNA. In some embodiments, the gapmers induce degradation of the target RNA molecule, e.g., mutant DMPK RNA, and also sterically inhibit the binding of a protein, e.g. MBNL1, to a DNA or RNA sequence, e.g., mutant DMPK RNA.

In some embodiments, the antisense oligonucleotide is a gapmer that binds to expanded CUG repeats in an RNA molecule. In particular embodiments, the gapmer binds to CUG repeats in a mutant DMPK RNA sequence. In some embodiments, the gapmer comprises a sequence that is at least 60%, 65%, 70%, 80%, 85%, 90%, 91%, 92%, 93%, 94%, 95%, 96%, 97%, 98%, 99% or 100% identical to any one of SEQ ID NOs: 9-12 or 22-23.

In some embodiments, the antisense oligonucleotide is a morpholino molecule that sterically blocks the binding of a protein or nucleic acid to a target RNA or DNA sequence. In some embodiments, the morpholino also triggers degradation of the target RNA or DNA sequence. In some embodiments, the morpholino molecule binds to mutant DMPK RNA and prevents the binding of MBNL1 to the DMPK RNA molecule. In some embodiments, the MBNL1 protein that is prevented from binding to the DMPK RNA molecule is free to bind to other RNA molecule substrates. In some embodiments, the morpholino molecule comprises 20-30 nucleotides. In other embodiments, the morpholino molecule comprises 23-27 nucleotides. In other embodiments, the morpholino molecule comprises 25 nucleotides. In some embodiments, the morpholino binds CUG repeats in an RNA molecule. In particular embodiments, the morpholino binds to CUG repeats in a mutant DMPK RNA sequence. In some embodiments, the morpholino is at least 60%, 65%, 70%, 80%, 85%, 90%, 91%, 92%, 93%, 94%, 95%, 96%, 97%, 98%, 99% or 100% identical to the sequence of 5'-AGCAGCAGCAGCAGCAGCAGCAGCA-3' (SEQ ID NO: 22). See, Wheeler, 2009, Science, 325: 336-339.

In some embodiments, the antisense oligonucleotides of the present disclosure are molecules including 2'-O-methyl (2'-OMe) and/or phosphorothioate modifications and that specifically trigger the degradation of an RNA molecule, e.g., mutant DMPK RNA. In some embodiments, these molecules include 2'-O-methyl (2'-OMe) and phosphorothioate modifications. In some embodiments, these molecules induce degradation of a target RNA sequence, e.g., mutant DMPK RNA, by means an RNaseH mediated degradation or by other than RNase H degradation. In particular embodiments, the non-gapmer molecules are at least 60%, 65%, 70%, 80%, 85%, 90%, 91%, 92%, 93%, 94%, 95%, 96%, 97%, 98%, 99% or 100% identical to the sequence of SEQ ID NO: 23 (5'-CAGCAGCAGCAGCAGCAGCAG-3'). See, Mulders, 2009, Proc. Natl. Acad. Sci USA, 106: 13915-20.

Representative modifications are depicted below. The disclosure contemplates antisense oligonucleotides comprising nucleotides modified, as depicted below, including antisense oligonucleotides including combinations of the depicted chemistries (e.g., antisense oligonucleotides including any one or more of the depicted modifications).

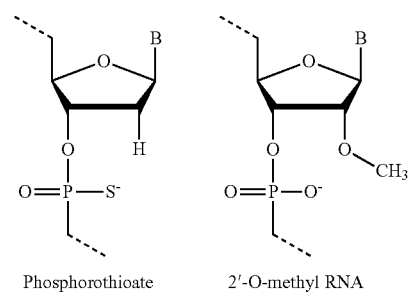

Phosphorothioate      2'-O-methyl RNA

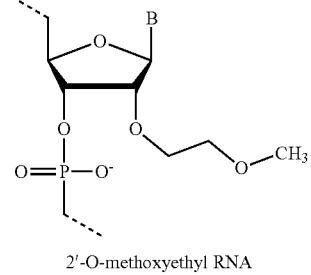

2'-O-methoxyethyl RNA

C.

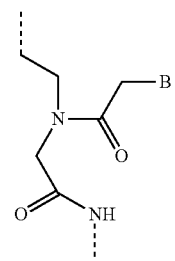 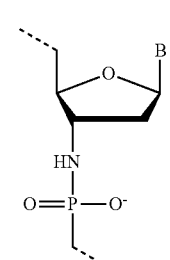

Peptide Nucleic Acid      N3'-P5'Phosphoroamidate

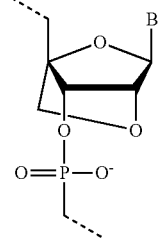 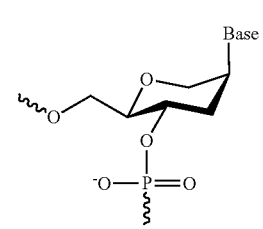

Locked Nucleic Acid      Hexitol Nucleic Acid

For all of the foregoing, it should be appreciated that certain antisense oligonucleotides promote RNaseH mediated degradation following hybridization to target. However, even for such antisense oligonucleotides, such capability does not mean or imply that this is the sole mechanism by which the antisense oligonucleotide functions.

III. MBNL Polypeptides

The present disclosure provides antisense conjugates suitable for decreasing expression of DMPK, such as by increasing degradation of DMPK transcripts. The conjugates may be used alone, such as in the treatment or research of myotonic dystrophy. Alternatively, these conjugates of the disclosure can be used in combination with other agents. Other agents include protein agents, analgesics, respiratory support, ambulatory support, physical therapy, and the like.

In certain aspects, the disclosure provides that antisense conjugates of the disclosure may be used with chimeric polypeptides comprising: (i) an MBNL1 polypeptide or a functional fragment thereof and (ii) and an internalizing moiety, such as described in US patent publication 2010-0111977 (the "'977 publication"), which is incorporated by reference in its entirety. The '977 publication describes numerous such chimeric polypeptides comprising these two portions, and exemplary such chimeric polypeptides are discussed herein. The disclosure contemplates that any such chimeric polypeptides may be used as part of a combination therapy with an antisense conjugate of the disclosure, where the two active agents are administered simultaneously or at different time. When administered at different times, the agents may be administered in either order and administered on the same or differing days.

Without being bound by theory, MBNL polypeptide is thought to be sequestered in the nucleus by the foci generated by the CUG expanded mutant DMPK transcript. Thus, one approach to ameliorate the negative effects of the mutation is to supply additional MBNL protein to help compensate for the MBNL protein that is no longer available to perform its function.

The use of antisense conjugates, as described herein, may ameliorate the negative effects of the DMPK mutation by a different mechanism (e.g., degrading transcript or blocking MBNL1 interaction with the transcript). In addition, treatment with MBNL1 polypeptide (e.g., a chimeric MBNL1-internalizing moiety polypeptide) acts by a different mechanism as compared to the antisense conjugates. Thus, treatment with any combination of the antisense conjugate types and/or with a MBNL1 polypeptide may be complementary, as each addresses the disease via different mechanisms of action. Accordingly, in certain embodiments, the administration of any of combination of these three different types of agents provides an additive effect. In other embodiments, the administration of any combination of these three different types of agents provides a synergistic effect. In either case, the effect may be measured in a cell based or animal model, such as measuring morphological changes in cells, measuring decreasing in nuclear foci, measuring improved movement in animal models, and the like.

Moreover, in certain embodiments, antisense conjugates of the disclosure include an MBNL1 portion. In a manner similar to combination therapy, such conjugates would provide both MBNL1 polypeptide and an antisense oligonucleotide to DMPK to cells.

The remainder of this section of the application describes suitable MBNL polypeptides for use in a chimeric polypeptide or as a portion of an antisense conjugate. As described in the '977 publication, such MBNL portions may be provided as a chimeric polypeptide, such as a fusion protein, with an internalizing moiety, such as the 3E10-related antibodies and antigen binding fragments described herein.

MBNL polypeptides include various splicing isoforms, functional fragments and variants, fusion proteins, and modified forms of the wildtype MBNL1 polypeptide, such as a human MBNL1 polypeptide. Such isoforms, functional fragments or variants, fusion proteins, and modified forms of the MBNL polypeptides have at least a portion of the amino acid sequence of substantial sequence identity to the native MBNL protein, and retain at least one function of the native MBNL protein. In certain embodiments, a functional fragment, variant, or fusion protein of an MBNL polypeptide comprises an amino acid sequence that is at least 80%, 85%, 90%, 95%, 97%, 98%, 99% or 100% identical to any of MBNL1 polypeptides (e.g., SEQ ID NOs: 1-7) provided herein.

In certain specific embodiments, the chimeric polypeptide comprises a functional fragment of the MBNL1 polypeptide which lacks a portion of the C-terminus. Optionally, the chimeric polypeptide comprises a functional fragment of the MBNL1 polypeptide which comprises all four zinc finger motifs. The structure and various motifs of the MBNL1 polypeptide are known in the art (see, e.g., Kino et al., 2004, Human Molecular Genetics, 13:495-507). An exemplary functional fragment of the MBNL1 polypeptide comprises residues 1-248 of SEQ ID NO: 3, lacking the 121 residues of the C-terminus. Optionally, functional fragments of the MBNL1 polypeptide may comprise residues 1-250, 1-260, 1-270, 1-280, 1-290, 1-300, 1-310, 10-320, 1-330, 1-340, 1-350, or 1-360 of SEQ ID NO: 3. In certain embodiments, similar functional fragments from other MBNL1 polypeptides are used. In certain embodiments, similar functional fragments from other MBNL1 polypeptides whose molecular weight is about 40 kD are used.

In certain embodiments, fragments or variants of the MBNL polypeptides can be obtained by screening polypeptides recombinantly produced from the corresponding fragment of the nucleic acid encoding an MBNL polypeptide. In addition, fragments or variants can be chemically synthesized using techniques known in the art such as conventional Merrifield solid phase f-Moc or t-Boc chemistry. The fragments or variants can be produced (recombinantly or by chemical synthesis) and tested to identify those fragments or variants that can function as a native MBNL protein, for example, by testing their ability to treat myotonic dystrophy.

In certain embodiments, the present disclosure contemplates modifying the structure of an MBNL polypeptide for such purposes as enhancing therapeutic or prophylactic efficacy, or stability (e.g., ex vivo shelf life and resistance to proteolytic degradation in vivo). Such modified MBNL polypeptides are considered functional equivalents of the naturally-occurring MBNL polypeptide. Modified polypeptides can be produced, for instance, by amino acid substitution, deletion, or addition. For instance, it is reasonable to expect, for example, that an isolated replacement of a leucine with an isoleucine or valine, an aspartate with a glutamate, a threonine with a serine, or a similar replacement of an amino acid with a structurally related amino acid (e.g., conservative mutations) will not have a major effect on the MBNL biological activity of the resulting molecule. Conservative replacements are those that take place within a family of amino acids that are related in their side chains.

This disclosure further contemplates generating sets of combinatorial mutants of an MBNL polypeptide, as well as truncation mutants, and is especially useful for identifying functional variant sequences. Combinatorially-derived variants can be generated which have a selective potency relative to a naturally occurring MBNL polypeptide. Likewise, mutagenesis can give rise to variants which have intracellular half-lives dramatically different than the corresponding wild-type MBNL polypeptide. For example, the altered protein can be rendered either more stable or less stable to proteolytic degradation or other cellular process which result in destruction of, or otherwise inactivation of the protein of interest (e.g., MBNL1,). Such variants can be utilized to alter the MBNL polypeptide level by modulating their half-life. There are many ways by which the library of potential MBNL variants sequences can be generated, for example, from a degenerate oligonucleotide sequence. Chemical synthesis of a degenerate gene sequence can be carried out in an automatic DNA synthesizer, and the synthetic genes then be ligated into an appropriate gene for expression. The purpose of a degenerate set of genes is to provide, in one mixture, all of the sequences encoding the desired set of potential polypeptide sequences. The synthesis of degenerate oligonucleotides is well known in the art (see for example, Narang, SA (1983) Tetrahedron 39:3; Itakura et al., (1981) Recombinant DNA, Proc. 3rd Cleveland Sympos. Macromolecules, ed. AG Walton, Amsterdam: Elsevier pp 273-289; Itakura et al., (1984) Annu Rev. Biochem. 53:323; Itakura et al., (1984) Science 198:1056; Ike et al., (1983) Nucleic Acid Res. 11:477). Such techniques have been employed in the directed evolution of other proteins (see, for example, Scott et al., (1990) Science 249:386-390; Roberts et al., (1992) PNAS USA 89:2429-2433; Devlin et al., (1990) Science 249: 404-406; Cwirla et al., (1990) PNAS USA 87: 6378-6382; as well as U.S. Pat. Nos. 5,223,409, 5,198,346, and 5,096,815).

Alternatively, other forms of mutagenesis can be utilized to generate a combinatorial library. For example, MBNL polypeptide variants can be generated and isolated from a library by screening using, for example, alanine scanning mutagenesis and the like (Ruf et al., (1994) Biochemistry 33:1565-1572; Wang et al., (1994) J. Biol. Chem. 269:3095-3099; Balint et al., (1993) Gene 137:109-118; Grodberg et al., (1993) Eur. J. Biochem. 218:597-601; Nagashima et al., (1993) J. Biol. Chem. 268:2888-2892; Lowman et al., (1991) Biochemistry 30:10832-10838; and Cunningham et al., (1989) Science 244:1081-1085), by linker scanning mutagenesis (Gustin et al., (1993) Virology 193:653-660; Brown et al., (1992) Mol. Cell Biol. 12:2644-2652; McKnight et al., (1982) Science 232:316); by saturation mutagenesis (Meyers et al., (1986) Science 232:613); by PCR mutagenesis (Leung et al., (1989) Method Cell Mol Biol 1:11-19); or by random mutagenesis, including chemical mutagenesis, etc. (Miller et al., (1992) A Short Course in Bacterial Genetics, CSHL Press, Cold Spring Harbor, N.Y.; and Greener et al., (1994) Strategies in Mol Biol 7:32-34). Linker scanning mutagenesis, particularly in a combinatorial setting, is an attractive method for identifying truncated (bioactive) forms of the MBNL polypeptide (e.g., MBNL1).

A wide range of techniques are known in the art for screening gene products of combinatorial libraries made by point mutations and truncations, and, for that matter, for screening cDNA libraries for gene products having a certain property. Such techniques will be generally adaptable for rapid screening of the gene libraries generated by the combinatorial mutagenesis of the MBNL polypeptides. The most widely used techniques for screening large gene libraries typically comprises cloning the gene library into replicable expression vectors, transforming appropriate cells with the resulting library of vectors, and expressing the combinatorial genes under conditions in which detection of a desired activity facilitates relatively easy isolation of the vector encoding the gene whose product was detected. Each of the illustrative assays described below are amenable to high through-put analysis as necessary to screen large numbers of degenerate sequences created by combinatorial mutagenesis techniques.

In certain embodiments, an MBNL polypeptide may include a peptide and a peptidomimetic. As used herein, the term "peptidomimetic" includes chemically modified peptides and peptide-like molecules that contain non-naturally occurring amino acids, peptoids, and the like. Peptidomimetics provide various advantages over a peptide, including enhanced stability when administered to a subject. Methods for identifying a peptidomimetic are well known in the art and include the screening of databases that contain libraries of potential peptidomimetics. For example, the Cambridge Structural Database contains a collection of greater than 300,000 compounds that have known crystal structures (Allen et al., Acta Crystallogr. Section B, 35:2331 (1979)). Where no crystal structure of a target molecule is available, a structure can be generated using, for example, the program CONCORD (Rusinko et al., J. Chem. Inf. Comput. Sci. 29:251 (1989)). Another database, the Available Chemicals Directory (Molecular Design Limited, Informations Systems; San Leandro Calif.), contains about 100,000 compounds that are commercially available and also can be searched to identify potential peptidomimetics of the MBNL polypeptides.

In certain embodiments, an MBNL polypeptide may further comprise post-translational modifications. Exemplary post-translational protein modification include phosphorylation, acetylation, methylation, ADP-ribosylation, ubiquitination, glycosylation, carbonylation, sumoylation, biotinylation or addition of a polypeptide side chain or of a hydrophobic group. As a result, the modified MBNL polypeptides may contain non-amino acid elements, such as lipids, poly- or mono-saccharide, and phosphates. Effects of such non-amino acid elements on the functionality of an MBNL polypeptide may be tested for its biological activity, for example, its ability to treat myotonic dystrophy. In certain embodiments, the MBNL polypeptide may further comprise one or more polypeptide portions that enhance one or more of in vivo stability, in vivo half life, uptake/administration, and/or purification. In other embodiments, the targeting moiety comprises an antibody or an antigen-binding fragment thereof.

In one specific embodiment of the present disclosure, an MBNL polypeptide may be modified with nonproteinaceous polymers. In one specific embodiment, the polymer is polyethylene glycol ("PEG"), polypropylene glycol, or polyoxyalkylenes, in the manner as set forth in U.S. Pat. Nos. 4,640,835; 4,496,689; 4,301,144; 4,670,417; 4,791,192 or 4,179,337. PEG is a well-known, water soluble polymer that is commercially available or can be prepared by ring-opening polymerization of ethylene glycol according to methods well known in the art (Sandler and Karo, Polymer Synthesis, Academic Press, New York, Vol. 3, pages 138-161).

By the terms "biological activity", "bioactivity" or "functional" is meant the ability of the MBNL protein to carry out the functions associated with wildtype MBNL proteins, for example, the regulation of exon splicing events in a cell or the ability to bind CUG repeats (for example, double stranded CUG repeats). The terms "biological activity", "bioactivity", and "functional" are used interchangeably herein. In certain embodiments, and as described herein, an MBNL protein, or chimeric polypeptide, or antisense conjugate comprising an MBNL protein having biological activity has the ability to bind CUG repeats (Warf, 2007, RNA, 12: 2238-51). In other embodiments, an MBNL protein or chimeric polypeptide or antisense conjugate comprising an MBNL protein having biological activity has the ability to bind CAG repeats (Ho, 2005, J. Cell Science, 118: 2923-2933). In other embodiments, an MBNL protein, or chimeric polypeptide, or antisense conjugate comprising an MBNL protein having biological activity has the ability to bind one or more of CUG repeats, CAG repeats, CCUG, CCG or CGG repeats. In certain embodiments, an MBNL having biological activity has the ability to bind to CAG, CCUG and CUG repeats. As used herein, "fragments" are understood to include bioactive fragments (also referred to as functional fragments) or bioactive variants that exhibit "bioactivity" as described herein. That is, bioactive fragments or variants of MBNL exhibit bioactivity that can be measured and tested. For example, bioactive fragments/functional fragments or variants exhibit the same or substantially the same bioactivity as native (i.e., wild-type, or normal) MBNL protein, and such bioactivity can be assessed by the ability of the fragment or variant to, e.g., remove fetal exons from DM1 myoblasts; bind to CUG repeats (as evaluated in vitro or in vivo). As used herein, "substantially the same" refers to any parameter (e.g., activity) that is at least 70% of a control against which the parameter is measured. In certain embodiments, "substantially the same" also refers to any parameter (e.g., activity) that is at least 75%, 80%, 85%, 90%, 92%, 95%, 97%, 98%, 99%, 100%, 102%, 105%, or 110% of a control against which the parameter is measured. In certain embodiments, fragments or variants of the MBNL polypeptide will preferably retain at least 50%, 60%, 70%, 80%, 85%, 90%, 95% or 100% of the MBNL biological activity associated with the native MBNL polypeptide. In certain embodiments, fragments or variants of the MBNL polypeptide have a half-life ($t_{1/2}$) which is enhanced relative to the half-life of the native protein. Preferably, the half-life of MBNL fragments or variants is enhanced by at least 10%, 20%, 30%, 40%, 50%, 60%, 70%, 80%, 90%, 100%, 125%, 150%, 175%, 200%, 250%, 300%, 400% or 500%, or even by 1000% relative to the half-life of the native MBNL protein. In some embodiments, the protein half-life is determined in vitro, such as in a buffered saline solution or in serum. In other embodiments, the protein half-life is an in vivo half life, such as the half-life of the protein in the serum or other bodily fluid of an animal. In addition, fragments or variants can be chemically synthesized using techniques known in the art such as conventional Merrifield solid phase f-Moc or t-Boc chemistry. The fragments or variants can be produced (recombinantly or by chemical synthesis) and tested to identify those fragments or variants that can function as well as or substantially similarly to a native MBNL protein.

With respect to methods of increasing MBNL bioactivity in cells, the disclosure contemplates all combinations of any of the foregoing aspects and embodiments, as well as combinations with any of the embodiments set forth in the detailed description and examples.

In some aspects, the present disclosure also provides a method of producing any of the foregoing chimeric polypeptides as described herein. Further, the present disclosure contemplates any number of combinations of the foregoing methods and compositions.

In certain aspects, an MBNL polypeptide may be a fusion protein which further comprises one or more fusion domains. Well known examples of such fusion domains include, but are not limited to, polyhistidine, Glu-Glu, glutathione S transferase (GST), thioredoxin, protein A, protein G, and an immunoglobulin heavy chain constant region (Fc), maltose binding protein (MBP), which are particularly useful for isolation of the fusion proteins by affinity chromatography. For the purpose of affinity purification, relevant matrices for affinity chromatography, such as glutathione-, amylase-, and nickel- or cobalt-conjugated resins are used. Fusion domains also include "epitope tags," which are usually short peptide sequences for which a specific antibody is available. Well known epitope tags for which specific monoclonal antibodies are readily available include FLAG, influenza virus haemagglutinin (HA), and c-myc tags. In some cases, the fusion domains have a protease cleavage site, such as for Factor Xa or Thrombin, which allows the relevant protease to partially digest the fusion proteins and thereby liberate the recombinant proteins therefrom. The liberated proteins can then be isolated from the fusion domain by subsequent chromatographic separation. In certain embodiments, the MBNL polypeptides may contain one or more modifications that are capable of stabilizing the polypeptides. For example, such modifications enhance the in vitro half life of the polypeptides, enhance circulatory half life of the polypeptides or reducing proteolytic degradation of the polypeptides.

In certain embodiments of any of the foregoing, the MBNL portion of the chimeric protein or antisense conjugate comprises MBNL1, or a functional fragment thereof. In certain embodiments, such MBNL1 polypeptide or functional fragment thereof retains the ability of native MBNL1 to bind to CUG repeats, as evaluated in vitro or in vivo. Further, in certain embodiments, the chimeric polypeptide or antisense conjugate that comprises such an MBNL1 polypeptide or functional fragment thereof can bind to CUG repeats. Exemplary functional fragments comprise at least 50, at least 60, at least 75, at least 100, at least 125, at least 150, at least 175, at least 200, at least 225, at least 230, at least 250, at least 260, at least 275, or at least 300 consecutive amino acid residues of a full length MBNL1 polypeptide. Similarly, in certain embodiments, the disclosure contemplates chimeric proteins or antisense conjugate where the MBNL portion is a variant of any of the foregoing MBNL1 polypeptides or bioactive fragments. Exemplary variants have an amino acid sequence at least 90%, 92%, 95%, 96%, 97%, 98%, or at least 99% identical to the amino acid sequence of a native MBNL1 polypeptide or functional fragment thereof, and such variants retain the ability to bind to CUG repeats, as evaluated in vitro or in vivo. The disclosure contemplates chimeric proteins and the use of such proteins wherein the MBNL portion comprises any of the MBNL1 polypeptides, fragments, or variants described herein in combination with any targeting moiety described herein. Exemplary MBNL1 polypeptides are set forth in SEQ ID NOs: 1-7. Moreover, in certain embodiments, the MBNL portion of any of the foregoing chimeric polypeptides may, in certain embodiments, be a fusion protein.

IV. Conjugates

Antisense conjugates of the present disclosure can be made in various manners. In certain embodiments, the C-terminus of an internalizing moiety (e.g., for example, the C-terminus of an scFv comprising the six CDRs set forth in SEQ ID NOs 16-21) can be linked to an antisense oligonucleotide. Alternatively, the N-terminus of an internalizing moiety (e.g., for example, the N-terminus of an scFv comprising the six CDRs set forth in SEQ ID NOs 16-21) can be linked to an antisense oligonucleotide. Similarly, for conjugates comprising an MBNL1 polypeptide, the MBNL1 polypeptide may be N or C-terminal to the internalizing moiety (See, for example, US publication 2010-0111977, incorporated by reference in its entirety). Further still, linkage can be via an exposed internal residue. By way of example, an antisense oligonucleotide may be conjugated to an internalizing moiety via an Fc portion of an antibody. In some embodiments, the internalizing moiety is conjugated to the 5' end of the antisense oligonucleotide by utilizing a disulfide attachment procedure similar to that described in Astriab-Fisher, et al., 2002, Pharmaceutical Research, 19(6): 744-754.

Regardless of conjugation chemistry or relative position of the portions of the conjugate, in certain embodiments, the conjugate includes one or more linkers. Such linkers may interconnect portions of the conjugate or may be within a portion of a conjugate (e.g., a Gly-Ser linker connecting a VH and VL domain in an scFv—see SEQ ID NO: 15). When a conjugate comprises more than one linker, the linkers may be the same or different.

In further embodiments, regardless of conjugation chemistry or relative position of the portions of the conjugate, the antisense oligonucleotide portion and the internalizing moiety portion are present at a 1:1 ratio.

Portions of a conjugate of the disclosure may be conjugated directly to each other. Alternatively, they may be conjugated to each other via a linker sequence, which separates portions by a distance sufficient to ensure that each domain properly folds and/or maintains its individual activity when provided in a conjugate. In certain embodiments, the linker is a cleavable linker.

In other embodiments, the portions of the conjugate may be conjugated or joined directly. For example, for conjugates comprising an MBNL portion, the MBNL portion and the internalizing moiety portion may be provided as a fusion protein.

In certain embodiments, the antisense conjugates of the disclosure are generated using well-known cross-linking reagents and protocols. For example, there are a large number of chemical cross-linking agents that are known to those skilled in the art and useful for cross-linking portions of a conjugate. For example, the cross-linking agents are heterobifunctional cross-linkers, which can be used to link molecules in a stepwise manner. Heterobifunctional cross-linkers provide the ability to design more specific coupling methods for conjugating, thereby reducing the occurrences of unwanted side reactions such as homo-protein polymers. A wide variety of heterobifunctional cross-linkers are known in the art, including succinimidyl 4-(N-maleimidomethyl) cyclohexane-1-carboxylate (SMCC), m-Maleimidobenzoyl-N-hydroxysuccinimide ester (MBS); N-succinimidyl (4-iodoacetyl) aminobenzoate (SIAB), succinimidyl 4-(p-maleimidophenyl) butyrate (SMPB), 1-ethyl-3-(3-dimethylaminopropyl) carbodiimide hydrochloride (EDC); 4-succinimidyloxycarbonyl-a-methyl-a-(2-pyridyldithio)-tolune (SMPT), N-succinimidyl 3-(2-pyridyldithio) propionate (SPDP), succinimidyl 6-[3-(2-pyridyldithio) propionate]hexanoate (LC-SPDP). Those cross-linking agents having N-hydroxysuccinimide moieties can be obtained as the N-hydroxysulfosuccinimide analogs, which generally have greater water solubility. In addition, those cross-linking agents having disulfide bridges within the linking chain can be synthesized instead as the alkyl derivatives so as to reduce the amount of linker cleavage in vivo. In addition to the heterobifunctional cross-linkers, there exists a number of other cross-linking agents including homobifunctional and photoreactive cross-linkers. Disuccinimidyl subcrate (DSS), bismaleimidohexane (BMH) and dimethylpimelimidate.2 HCl (DMP) are examples of useful homobifunctional cross-linking agents, and bis-[B-(4-azidosalicylamido)ethyl]disulfide (BASED) and N-succinimidyl-6(4'-azido-2'-nitrophenylamino)hexanoate (SANPAH) are examples of useful photoreactive cross-linkers for use in this disclosure. For a recent review of protein coupling techniques, see Means et al. (1990) Bioconjugate Chemistry. 1:2-12, incorporated by reference herein.

One particularly useful class of heterobifunctional cross-linkers, included above, contain the primary amine reactive group, N-hydroxysuccinimide (NHS), or its water soluble analog N-hydroxysulfosuccinimide (sulfo-NHS). Primary amines (lysine epsilon groups) at alkaline pH's are unprotonated and react by nucleophilic attack on NHS or sulfo-NHS esters. This reaction results in the formation of an amide bond, and release of NHS or sulfo-NHS as a by-product. Another reactive group useful as part of a heterobifunctional cross-linker is a thiol reactive group. Common thiol reactive groups include maleimides, halogens, and pyridyl disulfides. Maleimides react specifically with free sulfhydryls (cysteine residues) in minutes, under slightly acidic to neutral (pH 6.5-7.5) conditions. Halogens (iodoacetyl functions) react with —SH groups at physiological pH's. Both of these reactive groups result in the formation of stable thioether bonds. The third component of the heterobifunctional cross-linker is the spacer arm or bridge. The bridge is the structure that connects the two reactive ends. The most apparent attribute of the bridge is its effect on steric hindrance. In some instances, a longer bridge can more easily span the distance necessary to link two complex biomolecules.

One can use cross-linking agents such as heterobifunctional cross-linkers, which can be used to link molecules in a stepwise manner. Heterobifunctional cross-linkers provide the ability to design more specific coupling methods, thereby reducing the occurrences of unwanted side reactions. A wide variety of heterobifunctional cross-linkers are known in the art, including succinimidyl 4-(N-maleimidomethyl) cyclohexane-1-carboxylate (SMCC), m-Maleimidobenzoyl-N-hydroxysuccinimide ester (MBS); N-succinimidyl (4-iodoacetyl) aminobenzoate (SIAB), succinimidyl 4-(p-maleimidophenyl) butyrate (SMPB), 1-ethyl-3-(3-dimethylaminopropyl) carbodiimide hydrochloride (EDC); 4-succinimidyloxycarbonyl-a-methyl-a-(2-pyridyldithio)-tolune (SMPT), N-succinimidyl 3-(2-pyridyldithio) propionate (SPDP), succinimidyl 6-[3-(2-pyridyldithio) propionate]hexanoate (LC-SPDP). Those cross-linking agents having N-hydroxysuccinimide moieties can be obtained as the N-hydroxysulfosuccinimide analogs, which generally have greater water solubility. In addition, those cross-linking agents having disulfide bridges within the linking chain can be synthesized instead as the alkyl derivatives so as to reduce the amount of linker cleavage in vivo. In addition to the heterobifunctional cross-linkers, there exist a number of other cross-linking agents including homobifunctional and photoreactive cross-linkers. Disuccinimidyl suberate (DSS), bismaleimidohexane (BMH) and dimethylpimelimidate.2 HCl (DMP) are examples of useful homobifunctional cross-linking agents, and bis-[B-(4-azidosalicylamido)ethyl]disulfide (BASED) and N-succinimidyl-6(4'-azido-2'-nitrophenylamino)hexanoate (SANPAH) are examples of useful photoreactive cross-linkers. One useful class of heterobifunctional cross-linkers, included above, contain the primary amine reactive group, N-hydroxysuccinimide (NHS), or its water soluble analog N-hydroxysulfosuccinimide (sulfo-NHS). Another reactive group useful as part of a heterobifunctional cross-linker is a thiol reactive group. For a review of protein coupling techniques, see Means et al. (1990) Bioconjugate Chemistry. 1:2-12. Example 1 provides an exemplary method of radiolabeling a protein, in this case with an iodine label.

Preparing protein-conjugates using heterobifunctional reagents is a two-step process involving the amine reaction and the sulfhydryl reaction. For the first step, the amine reaction, the protein chosen should contain a primary amine. This can be lysine epsilon amines or a primary alpha amine found at the N-terminus of most proteins. The protein should not contain free sulfhydryl groups. In cases where both proteins to be conjugated contain free sulfhydryl groups, one protein can be modified so that all sulfhydryls are blocked using for instance, N-ethylmaleimide (see Partis et al. (1983) J. Pro. Chem. 2:263, incorporated by reference herein). Ellman's Reagent can be used to calculate the quantity of sulfhydryls in a particular protein (see for example Ellman et al. (1958) Arch. Biochem. Biophys. 74:443 and Riddles et al. (1979) Anal. Biochem. 94:75, incorporated by reference herein).

In certain embodiments, a cysteine is added to the C-terminus of the internalizing moiety, such as to the C-terminus of an scFv comprising the six CDRs set forth in SEQ ID NOs 16-21. The free cysteine can then be used to conjugate the internalizing moiety to an antisense oligonucleotide.

In any of the foregoing methods of cross-linking for chemical conjugation, a cleavable domain or cleavable linker can be used. Cleavage will allow separation of the internalizing moiety and the antisense oligonucleotide. For example, following penetration of a cell by an antisense conjugate, cleavage of the cleavable linker would allow separation of the antisense oligonucleotide from the internalizing moiety.

In certain embodiments, the antisense conjugates of the present disclosure can be conjugated to a fusion protein containing an MBNL polypeptide (or a functional fragment thereof) and an internalizing moiety (e.g., an antibody or a homing peptide), expressed as one contiguous polypeptide chain. The antisense oligonucleotide can be conjugated following production of this polypeptide chain, such as using methods described above.

In preparing such fusion protein, a fusion gene is constructed comprising nucleic acids which encode an MBNL polypeptide and a internalizing moiety, and optionally, a peptide linker sequence to span the MBNL polypeptide and the internalizing moiety. The use of recombinant DNA techniques to create a fusion gene, with the translational product being the desired fusion protein, is well known in the art. Both the coding sequence of a gene and its regulatory regions can be redesigned to change the functional properties of the protein product, the amount of protein made, or the cell type in which the protein is produced. The coding sequence of a gene can be extensively altered—for example, by fusing part of it to the coding sequence of a different gene to produce a novel hybrid gene that encodes a fusion protein. Examples of methods for producing fusion proteins are described in PCT applications PCT/US87/02968, PCT/US89/03587 and PCT/US90/07335, as well as Traunecker et al. (1989) Nature 339:68, incorporated by reference herein. Essentially, the joining of various DNA fragments coding for different polypeptide sequences is performed in accordance with conventional techniques, employing blunt-ended or stagger-ended termini for ligation, restriction enzyme digestion to provide for appropriate termini, filling in of cohesive ends as appropriate, alkaline phosphatase treatment to avoid undesirable joining, and enzymatic ligation. Alternatively, the fusion gene can be synthesized by conventional techniques including automated DNA synthesizers. In another method, PCR amplification of gene fragments can be carried out using anchor primers which give rise to complementary overhangs between two consecutive gene fragments which can subsequently be annealed to generate a chimeric gene sequence (see, for example, Current Protocols in Molecular Biology, Eds. Ausubel et al. John Wiley & Sons: 1992). The polypeptide encoded by the fusion gene may be recombinantly produced using various expression systems as is well known in the art (also see below).

Recombinantly conjugated polypeptides include embodiments in which the MBNL polypeptide is conjugated to the N-terminus or C-terminus of the internalizing moiety.

Antisense conjugates according to the disclosure can be used for numerous purposes. We note that any of the antisense conjugates described herein can be used in any of the methods described herein, and such suitable combinations are specifically contemplated.

Antisense conjugates described herein can be used to deliver an antisense oligonucleotide that hybridizes to DMPK to cells (and optionally to deliver MBNL), particularly to a muscle cell. Thus, the antisense conjugates can be used to facilitate transport of antisense oligonucleotides to cells in vitro or in vivo. By facilitating transport to cells, antisense conjugates improve delivery efficiency, thus facilitating working with antisense oligonucleotides that hybridize to DMPK in vitro or in vivo. Further, by increasing the efficiency of transport, the antisense conjugates may help decrease the amount of antisense oligonucleotide needed for in vitro or in vivo experimentation.

The antisense conjugates can be used to study the function of DMPK, MBNL and other proteins that interact with DMPK or MBNL in cells in culture, as well as to study transport and signaling involving these proteins. The antisense conjugates can be used to identify substrates and/or binding partners for MBNL1 in cells. The chimeric polypeptides can be used in screens to identify modifiers (e.g., small organic molecules or polypeptide modifiers) of MBNL1 activity in a cell. The antisense conjugates can be used to understand how the number of CUG repeats influences cell behavior. The antisense conjugates can be used to help treat or alleviate the symptoms of myotonic dystrophy in humans or in an animal model. The foregoing are merely exemplary of the uses for the subject chimeric polypeptides.

In some embodiments, the antisense conjugates are non-toxic to cells and/or animal subjects (e.g., humans). In some embodiments, the antisense conjugates are administered to a cell or animal subject at a dose non-toxic to the cell or animal subject. In some embodiments, toxicity of the antisense conjugates is tested in vitro by administering the antisense conjugates to a cell or cells and assessing cell health and/or survival. Cell health and survival may be assessed, for example, by monitoring cell morphology, monitoring cell adherence, or utilizing any one of several standard in vitro cytotoxicity assays such as a lactate dehydrogenase leakage assay, a methyl tetrazolium (MTT), 3-(4, 5-dimethylthiazol-2-yl)-5-(3-carboxymethoxyphenyl)-2-(4-sulfophenyl)-2Htetrazolium (MTS) assay or neutral red assays. In some embodiments, toxicity of the antisense conjugates is tested in vivo by administering the antisense conjugate to an animal (e.g., a mouse) and assessing the health and/or survival of the animal. Animal health and survival may be assessed, for example, by monitoring viability, behavior, weight, physical appearance, ability to thrive, and organ/tissue appearance upon death or sacrifice of the animal. In some embodiments, in vitro or in vivo antisense conjugate toxicity assay in which varying amounts of the antisense conjugate are administered to a cell or animal provide results which are used in order to prepare a dose response curve.

V. Methods of Use

The present disclosure provides antisense conjugates. Any of the antisense conjugates provided herein, including conjugates including any combination of features (e.g., comprising any antisense oligonucleotide portion and any internalizing moiety portion, and optionally an MBNL portion) may be used in any of a number of methods. For example, any of the antisense conjugates of the disclosure may be evaluated or studied in any of the cell or animal models described below.

Antisense conjugates of the disclosure are designed and intended to facilitate delivery of antisense oligonucleotides into cells, including into muscle cells. In fact, because the internalizing moieties generally used in these conjugates enter cells by ENT2, which is expressed in muscle but is not ubiquitously expressed, a level of enriched targeting to muscle is achieved. Accordingly, the disclosure provides methods for promoting delivery of an antisense oligonucleotide into cells, such as into muscle cells (including skeletal and cardiac muscle). This utility of the present disclosure is applicable to the research context, in which the antisense oligonucleotides are used to study myotonic dystrophy, as well as to the therapeutic context.

Antisense conjugates of the disclosure have numerous uses. For example, antisense conjugates are useful for in vitro studies of the function of DMPK protein, MBNL1 protein, as well as any of the proteins that interact with DMPK or MBNL1. The function of these proteins can be studied in healthy cells or animals, such as to understand the endogenous activity, function and interactions of these proteins. Additionally or alternatively, the function of these proteins can be studied in cells or animals harboring mutations, such as cells and animals that mimic all or a portion of the effects of myotonic dystrophy. In certain embodiments, the functions of these proteins can be studied in cells or animals harboring mutations such that there is expanded CUG repeats in the 3'UTR of the DMPK transcript (and/or expand CTG repeats in the DMPK gene). Amongst the important uses of antisense conjugates of the disclosure is studying and understanding changes in phenotype, protein-protein interactions, etc. that occurs as the extent of the CUG expansion increases. This is of use because, generally, the severity of myotonic dystrophy in subjects increases with increasing number of CUG repeats.

In vitro studies are also useful for comparing antisense conjugates of the disclosure to each other, as well as determining potential efficacy of using more than one antisense conjugate as part of a treatment regimen. For example, in vitro studies, followed by animal studies as appropriate, may be used to evaluate whether administering a cocktail of antisense conjugates (e.g., an antisense conjugate that hybridizes to CUG repeats of the 3'UTR+an antisense conjugate that hybridizes to the coding region of the transcript) provides increased efficacy.

Accordingly, antisense conjugates (one conjugate or multiple conjugates) are useful in, for example, the study of DMPK function, MBNL1 function and myotonic dystrophy biology.

Moreover, antisense conjugates of the disclosure are useful for treating (e.g., ameliorating one or more symptoms) myotonic dystrophy or for methods of delivering an antisense conjugate into cells in a patient. The terms "treatment", "treating", and the like are used herein to generally mean obtaining a desired pharmacologic and/or physiologic effect. The effect may be prophylactic in terms of completely or partially preventing a disease, condition, or symptoms thereof, and/or may be therapeutic in terms of a partial or complete cure for a disease or condition and/or adverse effect attributable to the disease or condition. "Treatment" as used herein covers any treatment of a disease or condition of a mammal, particularly a human, and includes: (a) preventing the disease or condition from occurring in a subject which may be predisposed to the disease or condition but has not yet been diagnosed as having it; (b) inhibiting the disease or condition (e.g., arresting its development); or (c) relieving the disease or condition (e.g., causing regression of the disease or condition, providing improvement in one or more symptoms). For example, "treatment" of DM1 encompasses a complete reversal or cure of the disease, or any range of improvement in conditions and/or adverse effects attributable to DM1 and DM2. Merely to illustrate, "treatment" of DM1 includes an improvement in any of the following effects associated with DM1: muscle weakness, muscle wasting, grip strength, cataracts, difficulty relaxing grasp, irregularities in heartbeat, constipation and other digestive problems, retinal degeneration, low IQ, cognitive defects, frontal balding, skin disorders, atrophy of the testicles, insulin resistance and sleep apnea. Moreover, improvement may be evaluated by examining cellular changes, such as by examining DMPK expression in tissue biopsy. Improvements in any of these conditions can be readily assessed according to standard methods and techniques known in the art. Other symptoms or cellular read-outs not listed above may also be monitored in order to determine the effectiveness of treating DM1. The population of subjects treated by the method of the disease includes subjects suffering from the undesirable condition or disease, as well as subjects at risk for development of the condition or disease.

By the term "therapeutically effective dose" is meant a dose that produces the desired effect for which it is administered. The exact dose will depend on the purpose of the treatment, and will be ascertainable by one skilled in the art using known techniques (see, e.g., Lloyd (1999) The Art, Science and Technology of Pharmaceutical Compounding).

In certain embodiments, one or more antisense conjugates of the present disclosure can be administered, together (simultaneously) or at different times (sequentially). In addition, antisense conjugates of the present disclosure can be administered alone or in combination with one or more additional compounds or therapies for treating myotonic dystrophy or for treating neuromuscular disorders in general. For example, one or more antisense conjugates can be co-administered in conjunction with one or more therapeutic compounds. When co-administration is indicated, the combination therapy may encompass simultaneous or alternating administration. In addition, the combination may encompass acute or chronic administration. Optionally, the antisense conjugates of the present disclosure and additional compounds (including an additional antisense conjugate of the disclosure) act in an additive or synergistic manner for treating myotonic dystrophy. Additional compounds to be used in combination therapies include, but are not limited to, MBNL1 polypeptide or a chimeric polypeptide comprising an MBNL1 polypeptide and an internalizing moiety. Depending on the nature of the combinatory therapy, administration of the antisense conjugates of the disclosure may be continued while the other therapy is being administered and/or thereafter. Administration of the antisense conjugates may be made in a single dose, or in multiple doses. In some instances, administration of the antisense conjugates is commenced at least several days prior to the other therapy, while in other instances, administration is begun either immediately before or at the time of the administration of the other therapy.

In another example, one or more antisense conjugates of the disclosure can be used as part of a therapeutic regimen combined with one or more additional treatment modalities. By way of example, such other treatment modalities include, but are not limited to, dietary therapy, occupational therapy, physical therapy, ventilator supportive therapy, massage, acupuncture, acupressure, mobility aids, assistance animals, and the like.

Note that although the antisense conjugates described herein can be used in combination with other therapies, in certain embodiments, an antisense conjugate is provided as the sole form of therapy. Regardless of whether administrated alone or in combination with other medications or therapeutic regiments, the dosage, frequency, route of administration, and timing of administration of the chimeric polypeptides is determined by a physician based on the condition and needs of the patient. Moreover, patients may be monitored to assess improvement in one or more symptoms or to assess cellular changes, such as by tissue biopsy.

VI. Methods of Administration

Various delivery systems are known and can be used to administer antisense conjugates of the disclosure, e.g., encapsulation in liposomes, microparticles, microcapsules, recombinant cells capable of expressing the compound, receptor-mediated endocytosis (see, e.g., Wu and Wu, 1987, J. Biol. Chem. 262:4429-4432). Methods of introduction can be enteral or parenteral, including but not limited to, intradermal, intramuscular, intraperitoneal, intravenous, subcutaneous, pulmonary, intranasal, intraocular, epidural, and oral routes. The antisense conjugates may be administered by any convenient route, for example, by infusion or bolus injection, by absorption through epithelial or mucocutaneous linings (e.g., oral mucosa, rectal and intestinal mucosa, etc.) and may be administered together with other biologically active agents. Administration can be systemic or local. In addition, it may be desirable to introduce the pharmaceutical compositions of the disclosure into the central nervous system by any suitable route, including epidural injection, intranasal administration or intraventricular and intrathecal injection; intraventricular injection may be facilitated by an intraventricular catheter, for example, attached to a reservoir, such as an Ommaya reservoir. Pulmonary administration can also be employed, e.g., by use of an inhaler or nebulizer, and formulation with an aerosolizing agent. In some embodiments, local administration is via the hepatic portal vein.

In certain embodiments, it may be desirable to administer antisense conjugates of the disclosure locally to the area in need of treatment (e.g., muscle); this may be achieved, for example, and not by way of limitation, by local infusion during surgery, topical application, e.g., by injection, by means of a catheter, or by means of an implant, the implant being of a porous, non-porous, or gelatinous material, including membranes, such as sialastic membranes, fibers, or commercial skin substitutes.

In certain embodiments, it may be desirable to administer antisense conjugates locally, for example, to the eye using ocular administration methods. In another embodiments, such local administration can be to all or a portion of the heart. For example, administration can be by intrapericardial or intramyocardial administration. Similarly, administration to cardiac tissue can be achieved using a catheter, wire, and the like intended for delivery of agents to various regions of the heart.

In other embodiments, antisense conjugates of the disclosure can be delivered in a vesicle, in particular, a liposome (see Langer, 1990, Science 249:1527-1533). In yet another embodiment, antisense conjugates of the disclosure can be delivered in a controlled release system. In another embodiment, a pump may be used (see Langer, 1990, supra). In another embodiment, polymeric materials can be used (see Howard et al., 1989, J. Neurosurg. 71:105). In certain specific embodiments, antisense conjugates of the disclosure can be delivered intravenously or subcutaneously.

In certain embodiments, antisense conjugates are administered by intravenous infusion. In certain embodiments, antisense conjugates are infused over a period of at least 10, at least 15, at least 20, or at least 30 minutes. In other embodiments, the antisense conjugates are infused over a period of at least 60, 90, or 120 minutes. Regardless of the infusion period, the disclosure contemplates that each infusion is part of an overall treatment plan where an antisense conjugate is administered according to a regular schedule (e.g., weekly, monthly, etc.).

The foregoing is applicable to administration to any subject or patient, whether human or non-human.

Additionally or alternatively, antisense conjugates of the disclosure can be administered to cells in culture. For examples, cells in culture are contacted with an antisense conjugate, for example, by adding such conjugate to culture medium containing the cells. Administration to cells in vitro is useful, for example, when the antisense conjugates are being tested for activity, or when comparing various conjugates for relative activity, specificity and the like. Optimizing an antisense conjugate, such as to select suitable modifications conjugation chemistry and the like, is typically performed in vitro.

Moreover, administration in vitro is useful for studying the mechanism of action of an antisense conjugate, as well as for studying the molecular biology and biochemistry of DMPK, myotonic dystrophy, and other proteins implicated in myotonic dystrophy and DMPK activity.

VII. Pharmaceutical Compositions

In certain embodiments, the subject antisense conjugates of the present disclosure are formulated with a pharmaceutically acceptable carrier. One or more antisense conjugates can be administered alone or as a component of a pharmaceutical formulation (composition). The antisense conjugates may be formulated for administration in any convenient way for use in human or veterinary medicine. Wetting agents, emulsifiers and lubricants, such as sodium lauryl sulfate and magnesium stearate, as well as coloring agents, release agents, coating agents, sweetening, flavoring and perfuming agents, preservatives and antioxidants can also be present in the compositions. In some embodiments, the composition is substantially pyrogen free.

Formulations of the subject antisense conjugates include those suitable for oral/nasal, topical, parenteral, rectal, and/or intravaginal administration. The formulations may conveniently be presented in unit dosage form and may be prepared by any methods well known in the art of pharmacy. The amount of active ingredient which can be combined with a carrier material to produce a single dosage form will vary depending upon the host being treated and the particular mode of administration. The amount of active ingredient which can be combined with a carrier material to produce a single dosage form will generally be that amount of the compound which produces a therapeutic effect.

In certain embodiments, methods of preparing these formulations or compositions include combining another type of therapeutic agents and a carrier and, optionally, one or more accessory ingredients. In general, the formulations can be prepared with a liquid carrier, or a finely divided solid carrier, or both, and then, if necessary, shaping the product.

Formulations for oral administration may be in the form of capsules, cachets, pills, tablets, lozenges (using a flavored basis, usually sucrose and acacia or tragacanth), powders, granules, or as a solution or a suspension in an aqueous or non-aqueous liquid, or as an oil-in-water or water-in-oil liquid emulsion, or as an elixir or syrup, or as pastilles (using an inert base, such as gelatin and glycerin, or sucrose and acacia) and/or as mouth washes and the like, each containing a predetermined amount of a subject antisense conjugate as an active ingredient. Suspensions, in addition to the active compounds, may contain suspending agents such as ethoxylated isostearyl alcohols, polyoxyethylene sorbitol, and sorbitan esters, microcrystalline cellulose, aluminum metahydroxide, bentonite, agar-agar and tragacanth, and mixtures thereof.

In solid dosage forms for oral administration (capsules, tablets, pills, dragees, powders, granules, and the like), one or more antisense conjugates of the present disclosure may be mixed with one or more pharmaceutically acceptable carriers, such as sodium citrate or dicalcium phosphate, and/or any of the following: (1) fillers or extenders, such as starches, lactose, sucrose, glucose, mannitol, and/or silicic acid; (2) binders, such as, for example, carboxymethylcellulose, alginates, gelatin, polyvinyl pyrrolidone, sucrose, and/or acacia; (3) humectants, such as glycerol; (4) disintegrating agents, such as agar-agar, calcium carbonate, potato or tapioca starch, alginic acid, certain silicates, and sodium carbonate; (5) solution retarding agents, such as paraffin; (6) absorption accelerators, such as quaternary ammonium compounds; (7) wetting agents, such as, for example, cetyl alcohol and glycerol monostearate; (8) absorbents, such as kaolin and bentonite clay; (9) lubricants, such a talc, calcium stearate, magnesium stearate, solid polyethylene glycols, sodium lauryl sulfate, and mixtures thereof; and (10) coloring agents. In the case of capsules, tablets and pills, the pharmaceutical compositions may also comprise buffering agents. Solid compositions of a similar type may also be employed as fillers in soft and hard-filled gelatin capsules using such excipients as lactose or milk sugars, as well as high molecular weight polyethylene glycols and the like. Liquid dosage forms for oral administration include pharmaceutically acceptable emulsions, microemulsions, solutions, suspensions, syrups, and elixirs. In addition to the active ingredient, the liquid dosage forms may contain inert diluents commonly used in the art, such as water or other solvents, solubilizing agents and emulsifiers, such as ethyl alcohol, isopropyl alcohol, ethyl carbonate, ethyl acetate, benzyl alcohol, benzyl benzoate, propylene glycol, 1,3-butylene glycol, oils (in particular, cottonseed, groundnut, corn, germ, olive, castor, and sesame oils), glycerol, tetrahydrofuryl alcohol, polyethylene glycols and fatty acid esters of sorbitan, and mixtures thereof. Besides inert diluents, the oral compositions can also include adjuvants such as wetting agents, emulsifying and suspending agents, sweetening, flavoring, coloring, perfuming, and preservative agents.

In particular, methods of the disclosure can be administered topically, either to skin or to mucosal membranes such as those on the cervix and vagina. The topical formulations may further include one or more of the wide variety of agents known to be effective as skin or stratum corneum penetration enhancers. Examples of these are 2-pyrrolidone, N-methyl-2-pyrrolidone, dimethylacetamide, dimethylformamide, propylene glycol, methyl or isopropyl alcohol, dimethyl sulfoxide, and azone. Additional agents may further be included to make the formulation cosmetically acceptable. Examples of these are fats, waxes, oils, dyes, fragrances, preservatives, stabilizers, and surface active agents. Keratolytic agents such as those known in the art may also be included. Examples are salicylic acid and sulfur. Dosage forms for the topical or transdermal administration include powders, sprays, ointments, pastes, creams, lotions, gels, solutions, patches, and inhalants. The subject antisense conjugates may be mixed under sterile conditions with a pharmaceutically acceptable carrier, and with any preservatives, buffers, or propellants which may be required. The ointments, pastes, creams and gels may contain, in addition to a subject polypeptide agent, excipients, such as animal and vegetable fats, oils, waxes, paraffins, starch, tragacanth, cellulose derivatives, polyethylene glycols, silicones, bentonites, silicic acid, talc and zinc oxide, or mixtures thereof. Powders and sprays can contain, in addition to a subject chimeric polypeptides, excipients such as lactose, talc, silicic acid, aluminum hydroxide, calcium silicates, and polyamide powder, or mixtures of these substances. Sprays can additionally contain customary propellants, such as chlorofluorohydrocarbons and volatile unsubstituted hydrocarbons, such as butane and propane.

Pharmaceutical compositions suitable for parenteral administration may comprise one or more antisense conjugates in combination with one or more pharmaceutically acceptable sterile isotonic aqueous or nonaqueous solutions, dispersions, suspensions or emulsions, or sterile powders which may be reconstituted into sterile injectable solutions or dispersions just prior to use, which may contain antioxidants, buffers, bacteriostats, solutes which render the formulation isotonic with the blood of the intended recipient or suspending or thickening agents. Examples of suitable aqueous and nonaqueous carriers which may be employed in the pharmaceutical compositions of the disclosure include water, ethanol, polyols (such as glycerol, propylene glycol, polyethylene glycol, and the like), and suitable mixtures thereof, vegetable oils, such as olive oil, and injectable organic esters, such as ethyl oleate. Proper fluidity can be maintained, for example, by the use of coating materials, such as lecithin, by the maintenance of the required particle size in the case of dispersions, and by the use of surfactants.

These compositions may also contain adjuvants, such as preservatives, wetting agents, emulsifying agents and dispersing agents. Prevention of the action of microorganisms may be ensured by the inclusion of various antibacterial and antifungal agents, for example, paraben, chlorobutanol, phenol sorbic acid, and the like. It may also be desirable to include isotonic agents, such as sugars, sodium chloride, and the like into the compositions. In addition, prolonged absorption of the injectable pharmaceutical form may be brought about by the inclusion of agents which delay absorption, such as aluminum monostearate and gelatin.

Injectable depot forms are made by forming microencapsule matrices of one or more polypeptide therapeutic agents in biodegradable polymers such as polylactide-polyglycolide. Depending on the ratio of drug to polymer, and the nature of the particular polymer employed, the rate of drug release can be controlled. Examples of other biodegradable polymers include poly(orthoesters) and poly(anhydrides). Depot injectable formulations are also prepared by entrapping the drug in liposomes or microemulsions which are compatible with body tissue.

In a preferred embodiment, the chimeric polypeptides of the present disclosure are formulated in accordance with routine procedures as a pharmaceutical composition adapted for intravenous or subcutaneous administration to human beings and/or suitable animal models. Where necessary, the composition may also include a solubilizing agent and a local anesthetic such as lidocaine to ease pain at the site of the injection. Where the composition is to be administered by infusion, it can be dispensed with an infusion bottle containing sterile pharmaceutical grade water or saline. Where the composition is administered by injection, an ampoule of sterile water for injection or saline can be provided so that the ingredients may be mixed prior to administration. In certain embodiments, pharmaceutical compositions comprising an antisense conjugate of the disclosure is lyophilized.

The amount of the antisense conjugates of the disclosure which will be effective in the treatment of a tissue-related condition or disease (e.g., myotonic dystrophy) can be determined by standard clinical techniques. In addition, in vitro assays may optionally be employed to help identify optimal dosage ranges. The precise dose to be employed in the formulation will also depend on the route of administration, and the seriousness of the condition, and should be decided according to the judgment of the practitioner and each subject's circumstances. However, suitable dosage ranges for intravenous administration are generally about 20-5000 micrograms of the active chimeric polypeptide per kilogram body weight. Suitable dosage ranges for intranasal administration are generally about 0.01 pg/kg body weight to 1 mg/kg body weight. Effective doses may be extrapolated from dose-response curves derived from in vitro or animal model test systems.

Moreover, when antisense conjugates of the disclosure are being used in vitro, the optimal dosage for administration to cells can be readily selected. For example, a dose response curve can be generated to determine an amount of agent that produces a response without inducing toxicity.

VIII. Assays for Testing Antisense Conjugates

The efficacy and properties of antisense conjugates of the disclosure may be readily tested by utilizing any of a number of available in vitro or in vivo assays. A few such assays are described below. The disclosure contemplates that any antisense conjugate of the disclosure (comprising any combination of antisense oligonucleotide portion and antibody (or antigen binding) portion) may be tested using any of these assays, as well as others known in the art.

In some embodiments, the in vitro assay is Fluorescence in Situ Hybridization (FISH). In this assay, cultures of cells (e.g., myosarcoma cells, myoblasts, primary muscle cells, DM500 myoblasts, COSM6 cells) expressing RNA having excess CUG repeats (e.g., cells expressing DMPK RNA having excess CUG repeats) are treated with an antisense-conjugate of the present disclosure, or with a control construct. Cells expressing RNA carrying CUG repeats possess RNA foci that are easily detected by using a fluorescent probe that targets CUG repeat sequences or sequences flanking the repeats, e.g., (CAG)5-Cy3-labeled LNA probes (Exiqon). See, Lee et al., 2012, Proc Natl Acad Sci USA, Early Edition. If the antisense-conjugate treatment of the cells is effective in inducing the degradation of the CUG-repeat RNA, the RNA foci in the cells, as detected using the fluorescent probes, is reduced. Such experiments indicate that the antisense conjugates are able to penetrate the cells and are functional in the presence of the internalizing moiety (e.g., function when delivered as a conjugate to, for example, decrease DMPK expression).

In some embodiments, the in vitro assay is immunodetection of MBNL1 protein in a cell treated with or without the antisense conjugate. MBNL1 typically displays a punctate staining pattern in DM1 cells or cells having transcripts with expanded CUG repeats, and treatment of these cells with an antisense conjugate is expected to liberate MBNL1 such that it is free to act on other RNA transcript targets. As such, MBNL1 in cells treated with the antisense conjugates is expected to take on a more diffuse staining pattern.

In some embodiments, Real-Time Polymerase Chain Reaction (RT-PCR) is employed in order to test the efficacy of the antisense conjugates. In these embodiments, cultures of cells (e.g., myosarcoma cells, myoblasts, primary muscle cells, DM500 myoblasts, COSM6 cells) expressing RNA having excess CUG repeats (e.g., cells expressing DMPK RNA having excess CUG repeats) are treated with an antisense-conjugate of the present disclosure, or with a control construct. The cells are then harvested and prepared for RT-PCR using primers specific to the RNA having the excess CUG repeats. A reduction in the amplified RNA transcript indicates successful degradation of the RNA transcript. See, Lee et al., 2012, Proc Natl Acad Sci USA, Early Edition. Such experiments indicate that the antisense conjugates are able to penetrate the cells and are functional in the presence of the internalizing moiety (e.g., function when delivered as a conjugate to, for example, decrease DMPK expression).

In some embodiments, Northern Blot analysis is used to test the efficacy of the antisense-conjugate of the present disclosure. Cell cultures, or tissues, are treated and harvested as described above for the FISH or RT-PCR embodiments. Northern Blot analysis using probes specific to the CUG repeats, or regions flanking the CUG repeats, are employed. A reduction in CUG repeat RNA transcript is suggestive of degradation of the RNA transcript. See, Mulders, et al., 2009, PNAS, 106(33): 13915-13920. Such experiments indicate that the antisense conjugates are able to penetrate the cells and are functional in the presence of the internalizing moiety (e.g., function when delivered as a conjugate to, for example, decrease DMPK expression).

In some embodiments, the efficacy of the antisense-conjugates of the present disclosure is evaluated in vivo in an animal model that expresses RNA carrying CUG repeats. In some embodiments, the animal model is a mouse, a rat, a pig, a dog or a non-human primate.

In some embodiments, the animal model is a mouse engineered to inducibly express in skeletal muscle the DMPK gene containing large tracts of CTG repeats. Such mice display several features observed in human cases of DM1 disease (Orengo et al., 2008, PNAS, 105(7): 2646-2651). These DMPK-CTG mice possess DPMK-CUG RNA colocalizing with MBNL1 protein, display defective splicing events and possess an increase in the levels of CUGBP1, a splicing factor associated with regulating alternative splicing events in DM1 disease in humans (Orengo, 2008). In addition, these mice display myotonic electromyograms (Orengo, 2008). These mice also display severe and progressive skeletal muscle wasting and a dramatic loss of muscle function (Orengo, 2008). Thus, in certain embodiments, antisense conjugates of the disclosure are administered to these mice. The efficacy of these antisense conjugates can be compared to controls, including antisense oligonucleotides that are not provided as a conjugate with an internalizing moiety. Following administration, animals may be evaluated for improvement in muscle function, weight gain, as well as cellular changes observed in muscle biopsies. Evaluation in animal models is particularly useful for evaluating the additional benefit of providing an antisense oligonucleotide as a conjugate with an internalizing moiety. This is because, in the context of cell culture, permeabilizing and other cell culture agents may compensate for what would otherwise be poor or suboptimal penetration of an unconjugated antisense oligonucleotide. Thus, comparison in an animal model may be more helpful in illustrating the additional benefits provided by the antisense conjugates of the disclosure.

In other embodiments, the animal model is a mouse model engineered to express the human skeletal actin (HSA) gene with an untranslated CTG repeat (HSAlr41 mouse) in skeletal muscle. This model is associated with ~40% mortality by 44 weeks of age (Mankodi, 2000, Science, 289: 1769-1772). In addition, these mice also display myotonic discharges and abnormal hind-limb posture during the initiation of movement (Mankodi, 2000). These mice also have an increase in central nuclei and ring fibers and variability in fiber size in skeletal muscle, as well as an up-regulated activity of proteins involved in oxidative muscle fibers, succinate dehydrogenase and cytochrome oxidase (Mankodi, 2000). The long-repeat transcripts of the HSA gene are also found to be retained within the nuclei of these HSAlr41 mice (Mankodi, 2000). These mice also display alternative splicing of the CIC-1 gene transcript and upregulation of the transcription of the Eda2r, Uchl1, and Sarcolipin genes (Wheeler, 2009, Science, 325: 336-39). These mice do not display significant muscle wasting or weakness (Mankodi, 2000). Thus, in certain embodiments, antisense conjugates of the disclosure are administered to these mice. The efficacy of these antisense conjugates can be compared to controls, including antisense oligonucleotides that are not provided as a conjugate with an internalizing moiety. Following administration, animals may be evaluated for improvement in movement, as well as cellular changes observed in muscle biopsies and molecular changes. Evaluation in animal models is particularly useful for evaluating the additional benefit of providing an antisense oligonucleotide as a conjugate with an internalizing moiety. This is because, in the context of cell culture, permeabilizing and other cell culture agents may compensate for what would otherwise be poor or suboptimal penetration of an unconjugated antisense oligonucleotide. Thus, comparison in an animal model may be more helpful in illustrating the additional benefits provided by the antisense conjugates of the disclosure.

In certain embodiments, the present disclosure contemplates methods of surveying improvements in disease phenotypes using the antisense-conjugates of the present disclosure disclosed herein in any one or more animal models, such as the mouse models described above, or in cell culture. By way of example, various parameters can be examined in experimental animals treated with a subject antisense-conjugate, and such animals can be compared to controls. Exemplary parameters that can be assessed to evaluate potential efficacy include, but are not limited to: decrease in the number of CUG-repeat RNA foci in the cells of isolated tissues (by utilizing such techniques as FISH as discussed above), decrease in levels of the CUG-repeat RNA (by utilizing such techniques as the FISH, Northern Blots or RT-PCR assays described above); increase in lifespan; increase in muscle size; weight gain; decrease in myotonic behavior (e.g., closer to normal levels of muscle relaxation); improvements in myocardiogram results (e.g., decrease in myotonic discharges); improved scores on treadmill tests; improved gait; decrease in the number of nuclei in skeletal muscle; decrease in aberrant splicing events; decreased levels of CUGBP1; correction of the splicing of any of the CIC-1, Titin, Zasp, and Serca-1 gene transcripts; decrease in of the transcription of the Eda2r, Uchl1 and/or Sarcolipin genes; normal or improved spinal curvature; decrease in activity of proteins involved in oxidative muscle fibers; and/or decrease in number of myofiber splitting events.

Moreover, these and wildtype animals may be used for pharmacokinetic studies to determine the optimal dose, clearance rate, volume of distribution, and half-life of the antisense-conjugates. The PK/PD/TK of an antisense conjugate can then be examined in larger animals such as rats, dogs, and primates.

The above mouse models provide a suitable animal model system for assessing the activity and effectiveness of the subject antisense conjugates. These models have correlations with symptoms of DM1, and thus provide appropriate models for studying myotonic dystrophy. Activity of the antisense-conjugates can be assessed in these mouse models, and the results compared to that observed in wildtype control animals and animals not treated with the antisense conjugates.

IX. Kits

In certain embodiments, the disclosure also provides a pharmaceutical package or kit comprising one or more containers filled with at least one antisense conjugate of the disclosure. Optionally associated with such container(s), or otherwise provided in the package, can be a notice in the form prescribed by a governmental agency regulating the manufacture, use or sale of pharmaceuticals or biological products, which notice reflects (a) approval by the agency of manufacture, use or sale for human administration, (b) directions for use, or both.

In certain embodiments, the disclosure provides a pharmaceutical package or kit comprising one container filled with at least one antisense conjugate of the disclosure and one container filled with an MBNL1 chimeric polypeptide. The kit may optionally contain additional containers, for example containers with solution to reconstitute agents provided in lyophilized form. Moreover, the kit may optionally include, for example associated with the containers or otherwise in the package, notice in the form prescribed by a governmental agency regulating the manufacture, use or sale of pharmaceuticals or biological products, which notice reflects (a) approval by the agency of manufacture, use or sale for human administration, (b) directions for use, or both. Alternatively, the antisense conjugate and the MBNL1 chimeric polypeptide may be purchased separately, such as in separate kits. In either case, instructions may include directions and dosages for embodiments in which both agents are administered (simultaneously or consecutively), as well as directions and dosages for embodiments in which only one of the two agents are administered.

In certain embodiments of either of the foregoing, a kit may comprise more than one antisense conjugate. In certain embodiments, each antisense conjugate is provided in a separate container. In other embodiments, the antisense conjugates are premixed and provided in a single container.

In other embodiments, either of the foregoing kits is instead packaged for research use only. In such cases, the labeling and directions indicate that the agents are not for use in human subjects, but are for research purposes.

EXEMPLIFICATION

The disclosure now being generally described, it will be more readily understood by reference to the following examples, which are included merely for purposes of illustration of certain aspects and embodiments of the present disclosure, and are not intended to limit the disclosure. For example, the particular constructs and experimental design disclosed herein represent exemplary tools and methods for validating proper function. As such, it will be readily apparent that any of the disclosed specific constructs and experimental plan can be substituted within the scope of the present disclosure.

Example 1

Antisense Oligonucleotide Conjugate Synthesis

A fluorescently-labeled antisense oligonucleotide is generated in a manner similar to that described in Astriab-Fissher et al., 2002, Pharmaceutical Research, 19(6): 744-54. An antisense oligonucleotide having a sequence of SEQ ID NO: 9 is dissolved in 0.9 ml of 0.2 M $Na_2CO_3$/$NaHCO_3$ (pH 9.0) buffer and 90 µl of 0.2 M 5-(and 6-)-carboxytetramethylrhodamine N-hydroxysuccinimidyl ester (NHS-TAMRA, Molecular Probes) in DMSO is added. The reaction mixture is incubated in the dark at 37° C. for 4 hours and excess dye is removed by gel-filtration on a Spherilose GCL-25 (Isco, Inc.) (10×250 mm) column. The antisense oligonucleotide of SEQ ID NO: 9 could be substituted with any of the oligonucleotides having the sequences of SEQ ID NOs: 10-12 or 22-23. These oligonucleotides are exemplary of oligonucleotides within the scope of the present disclosure.

An internalizing moiety/antibody conjugate is synthesized by conjugating the fluorescently labeled antisense oligonucleotide to a 3E10 scFv polypeptide that includes the amino acid sequences of SEQ ID NOs: 13 and 14 in a manner similar to that described in Astriab-Fisher et al., 2002, Pharmaceutical Research, 19(6): 744-54. The antisense oligonucleotide is dissolved in 1.5 ml of 0.1 M $KH_2PO_4$ (pH 7.5), 0.3 M KBr, 8 M urea buffer. The solution is degassed and 3E10 scFv is added under argon. The reaction mixtures are incubated under argon at room temperature. The resulting conjugates are separated by IE HPLC on a Mono Q (10×100 MM) column using a 0-1.2 M gradient of KBr established over 60 min in 70 mM $KH_2PO_4$ (pH 6.5), 5 M urea, 30% $CH_3CN$. The amounts of the conjugates are determined spectrophotometrically based on the calculated molar absorption coefficients at $\lambda=260$ nm. RP HPLC and 20% denaturing PAGE analyses are used to check the purity of the conjugates and to verify the composition.

Example 2

Uptake and Cellular Distribution of the Antisense Oligonucleotide Conjugates

Human or murine myoblasts are cultured in 100 mm dishes. 3E10-antisense oligonucleotide conjugates or free antisense oligonucleotides are mixed in Opti-MEM and incubated with the myoblasts at 37° C. for various time points (e.g., thirty minutes, one hour, three hours, six hours). After treatment with the antisense conjugates or oligonucleotides alone, the cells are removed with trypsin/EDTA and split for fluorescence microscopy or flow cytometry analysis. Half of the cells are resuspended in 1 ml 10% FBS/DMEM and incubated for 6 hours on fibronectin (10 µg/ml)-coated cover slides. The distribution of fluorescence is analyzed on a fluorescence microscope equipped for transmitted light and incident-light fluorescence analysis, with a 100-watt mercury lamp, oil immersion objective and H5546 filter. Images are captured with a slow scan charge-coupled device Video Camera System using the MetaMorph Imaging System. For flow cytometry analysis, the cells are resuspended in 500 µl of PBS and measured for the accumulation of TAMRA marker on a flow cytometer. The rate of uptake of the antisense conjugates may be determined by examining the fluorescence in the cells after the different time points tested.

Example 3

In Vitro Analysis of Efficacy of Antisense Conjugates

DM1 and wildtype murine and/or human myoblasts are treated with the antisense conjugate of Example 1, the antisense oligonucleotide alone, or the 3E10 scFv polypeptide alone for various time periods (e.g., 30 minutes, 1 hour, 2 hours, 3 hours, or 4 hours). Total RNA from treated DM1 and wildtype myoblasts are purified using Trizol reagent and quantified using a spectrophotometer. To assess if treatment with the antisense conjugate results in the removal of fetal exons from DM1 myoblasts we use RTPCR employing a series of previously validated primers that coamplify fetal and adult mRNAs (Kanadia et al., 2006, Proc Natl Acad Sci USA, 103(31): 11748-53; Derossi et al., 1994, J Biol Chem, 269(14): 10444-50; Vicente et al., 2007, Differentiation, 75(5): 427-40; Yuan et al., 2007, Nucleic Acids Res, 35(16): 5474-86; Weisbart et al., 1990, J Immunol, 144(7): 2653-8; Mankodi et al., 2005, Circ Res, 97(11): 1152-5; Ashizawa et al., 1993, Neurology, 43(12): 2674-8). Following gel electrophoresis of the RTPCR products, the relative abundance of fetal and adult PCR products is compared against wild-type and DM1 myoblasts treated with antisense conjugate, the antisense oligonucleotide alone, or the 3E10 scFv polypeptide alone. An increase in the amount of adult versus fetal PCR products in antisense conjugate treated DM1 myoblasts constitute successful treatment. Samples of PCR products are cut with sequence specific restriction enzymes to verify the identity of each PCR product and water only amplifications are included as negative controls. The band size of an adult or fetal PCR product of a given gene is normalized to take into account the effect of greater fluorescence in larger ethidium bromide stained PCR products. If treatment of DM1 myoblasts does not improve the spliceopathy following application to untransfected DM1 myoblasts, DM1 myoblasts is transfected with the ENT2 transporter cDNA (Hansen et al., 2007, J Biol Chem 282(29): 20790-3), followed two days later by addition of conditioned media. The specificity of the antisense conjugates for the ENT2 transporter is validated by addition of nitrobenzylmercaptopurine riboside (NBMPR), an ENT2 specific inhibitor (Pennycooke et al., 2001, Biochem Biophys Res Commun. 280(3): 951-9) to ENT2 transfected cells just prior to addition of the antisense conjugate.

Distribution of MNBL1 in DM1 myoblasts treated with the antisense conjugates, the antisense oligonucleotides alone, 3E10 alone or vehicle control is also be assessed. The DM1 myoblasts described above that were harvested for fluorescence microscopy is treated with a rabbit polyclonal anti-MBNL1 antibody A2764 at a concentration of 1:5,000, followed by incubation with AlexaFluor 488-labeled goat-anti-rabbit secondary antibody at a concentration of 1:500. Samples are imaged with a laser scanning confocal microscope configured for imaging the TAMRA and AlexaFluor 488 sequentially. If the treatment of the DM1 myoblasts results in a more diffuse pattern of the MBNL1 staining than observed in any of the control treated DM1 myoblasts, then this is indicative of the antisense conjugate liberating endogenous MBNL1 from its sequestration in CUG RNA foci.

In a separate in vitro experiment, cultures of C2C12 myoblasts expressing RNA transcripts having an expanded number of 800 CUG repeats ("CUG 800") are treated with antisense conjugate. By measuring Wst1 levels, cell proliferation is assessed in CUG 800 C2C12 cells treated with antisense conjugate, and is compared to cell proliferation observed in cultures of CUG 800 C2C12 cells treated with antisense conjugate alone, 3E10 alone or vehicle control. Cell proliferation of CUG 800 C2C12 cells treated with antisense conjugate is also compared to cell proliferation observed in cultures of untreated C2C12 cells expressing RNA transcripts having no CUG repeats ("CUG 0"). If the treatment of the CUG 800 C2C12 cells with the antisense conjugate results in a higher proliferation rate than that observed in any of the control treated CUG 800 C2C12 cells, this is indicative that the antisense conjugate is able to increase cell survival in cells having RNA transcripts with expanded numbers of CUG repeats.

In addition to proliferation, morphology of CUG 800 C2C12 cells may also be assessed following treatment with the antisense conjugate and any of the control treatments. Untreated CUG 800 C2C12 cells are larger and more swollen than an untreated CUG 0 C2C12 cell. If the treatment of the CUG 800 C2C12 cells with the antisense conjugate results in a smaller, less swollen morphology than that observed in any of the control treated CUG 800 C2C12 cells, this is indicative that the antisense conjugate is able to improve morphology of cells having RNA transcripts with expanded numbers of CUG repeats.

Cytotoxicity of the antisense conjugate is determined by administering the antisense conjugate to the cells at varying doses and then monitoring cell morphology, monitoring cell adherence, or utilizing any one of several standard in vitro cytotoxicity assays such as a lactate dehydrogenase leakage assay, a methyl tetrazolium (MTT), 3-(4,5-dimethylthiazol-2-yl)-5-(3-carboxymethoxyphenyl)-2-(4-sulfophenyl)-2Htetrazolium (MTS) assay or neutral red assays.

Example 4

In Vivo Assessment of Muscle Targeted Antisense Oligonucleotides in MBNL1 KO Mice Selection of a DM1 Mouse Model for Evaluation The MBNL1 KO mouse recapitulates DM1 in many ways and exhibits an early onset of disease (6 weeks of age). MBNL1 KO mice possess no CTG expansions and thus the sequestering effect of the polyCUG mRNAs could result in an underestimation of the amount of MBNL1 that would be needed to correct the spliceopathy in DM1 (Kanadia et al., 2003, Science, 302: 1978-1980). The advantage of using MBNL1 KO mice is that MBNL KO mice exhibit a greater degree of fetal exon inclusion than HSAlr mice (Derossi et al., 1994, J Biol Chem, 269(14): 10444-50). The antisense-conjugate of Example 1 or the antisense oligonucleotide alone is administered to homozygous MBNL1 KO (−/−) and wildtype (+/+) mice. The homozygous MBNL1 KO (−/−) and wildtype (+/+) mice are C57BL6 congenic.

Materials and Methods i) Injection of the Antisense Conjugate

The antisense conjugate is formulated and diluted in a buffer that is consistent with intravenous injection (e.g. sterile saline solution or a buffered solution of 50 mM Tris-HCl, pH 7.4, 0.15 M NaCl). The amount of antisense conjugate given to each mouse is calculated as follows: dose (mg/kg)×mouse weight (kg)×stock concentration (mg/ml) =volume (ml) of stock per mouse, q.s. to 100 ul with vehicle.

ii) Blood Collection

Blood is collected by cardiac puncture at the time that animals are sacrificed for tissue dissection. Serum is removed and frozen at −80° C. To minimize the effects of thawing and handling all analysis of antisense conjugate circulating in the blood is performed on the same day.

iii) Tissue Collection and Preparation

Sampled tissues is divided for immunoblot, RTPCR, formalin-fixed paraffin-embedded tissue blocks and frozen sections in OCT. One half of the heart, liver, lung, spleen, kidneys, quadriceps, EDL, soleus, diaphragm, and biceps is subdivided and frozen in plastic tubes for further processing for immunoblot and RTPCR analysis. The remaining half of the heart, liver, lung, spleen, kidneys, quadriceps, EDL, soleus, diaphragm, and biceps is subdivided, frozen in OCT tissue sectioning medium, or fixed in zinc-formaldehyde fixation for 24 to 48 hours at 4° C. and paraffin embedded.

iv) Histological Evaluation

Brightfield microscopy of HE sections is used to determine the percentage of centrally nucleated myofibers from five randomly selected fields. At least 200 fibers is counted per mouse per muscle group. Scoring of central nuclei, inflammation and necrosis of hematoxylin and eosin stained skeletal and cardiac sections is performed. Controls include vehicle and treated heterozygous MBNL1+/+ mice and vehicle treated MBNL1−/− mice.

v) RNA Collection RTPCR: MBNL1 Mediated Correction of Spliceopathy in DM1 Cells

To be performed as described in Example 1, except tissues is crushed in liquid nitrogen prior to extraction with Trizol reagent. Controls include vehicle and treated heterozygous MBNL1+/+ mice and vehicle treated MBNL1−/− mice.

vi) Immunofluorescence

Detection of ClC-1, a chloride channel, is detected with a 1:1000 dilution of polyclonal anti-ClC-1 antibody that recognizes the C-terminus of ClC-1 (Alpha Diagnostic, San Antonio) followed by 1:1000 dilution of FITC-conjugated anti-rabbit secondary antibody (Jackson Immunoresearch). Controls include vehicle and treated heterozygous MBNL1+/+ mice and vehicle treated MBNL1−/− mice.

vii) Immunoblot

Immunoblot is used to detect 3E10 immune reactive material in the antisense conjugate treated muscles and tissues. Antibody detection of blotted proteins use NBT/BCIP as a substrate. Controls include vehicle and treated heterozygous MBNL1+/+ mice and vehicle treated MBNL1−/− mice.

viii) Toxicity

Toxicity of the antisense conjugates is tested in vivo by administering varying amounts of the antisense conjugate to the mice and assessing the health and/or survival of the animal. Animal health and survival is assessed by monitoring any of the following: viability, behavior, weight, physical appearance, ability to thrive, and organ/tissue appearance upon death or sacrifice of the animal.

ix) Statistical Analysis

Pairwise comparisons employ Student's t-test. Comparisons among multiple groups employ ANOVA. In both cases a p-value <0.05 is considered statistically significant.

Example 5

In Vivo Assessment of Muscle Targeted Antisense Conjugate in HSAlr41 Mice

Example 5 is performed in accordance with Example 4, except that transgenic HSAlr41 mice are injected with the antisense conjugate of Example 1, the antisense oligonucleotide alone, 3E10 alone or a vehicle control, over a longer dosing period, followed by electromyographic and end of life histologic and spliceopathic assessments of skeletal muscle. In addition to immunofluorescence detection of MBNL1, fluorescent in situ hybridization (FISH) to determine if the antisense conjugate has altered the distribution of nuclear RNA foci is also performed.

i) Electrophysiology

Three days following the last of four doses of the antisense conjugate electromyographic assessments of the antisense conjugate treated HSALr41+/+ and FVB (wildtype control) mice is made as previously published (Mankodi et al., 2000, Science, 2000, 289(5485): 1769-73) and under the supervision of the local IACUC protocol.

ii) Muscle Relaxation Test

Three days following the last of four doses of the antisense conjugate muscle relaxation tests of 3E10-MBNL1 treated HSALr41+/+ and FVB mice is made as previously published (Mankodi et al., 2000, Science, 2000, 289(5485): 1769-73) and under the supervision of the local IACUC protocol.

Example 6

In Vivo Assessment of Muscle Targeted Antisense Conjugate in MBNL2-/- Mice

Example 6 is performed as in Examples 4 and 5, except that treatment of MBNL2-/- mice is assessed. MBNL2-/- mice also is evaluated by electromyographic and end of life histologic and spliceopathic assessments of skeletal muscle similar to Example 5. MBNL2-/- mice also is evaluated by examining spinal curvature.

Spinal Curvature

Spinal curvature is quantified using X-ray radiograph analysis as described in Hao et al. (Hao, et al., 2008, Developmental Dynamics, 237: 403-410). Controls include vehicle and treated FVB mice and vehicle treated MBNL2+/+ mice.

Example 7

In Vivo Assessment of Muscle Targeted MBNL1 in Inducible DMPK-CTG Mice

DMPK-CTG mice inducibly express the DMPK gene containing CTG repeats in the 5th exon. Tamoxifen treatment induces DMPK-CTG expression (Orengo et al., 2008, PNAS, 105(7): 2646-2651). DMPK-CTG mice are 3-4 months of age before receiving 1 mg of tamoxifen injections daily for five days (Orengo, 2008). Following tamoxifen treatment, antisense conjugate and control treatment and subsequent treatment analysis begins as described in Example 4. In addition, transgenic DMPK-CTG mice is evaluated by electromyographic and end of life histologic and spliceopathic assessments of skeletal muscle similar to Example 5. Bitransgenic mice expressing no CTG repeats, or DMPK-CTG mice that did not receive tamoxifen treatment is used as controls. Control or test mice also receive either the antisense conjugate treatment, the antisense oligonucleotide alone, 3E10 alone or vehicle control.

i) Immunoblot

In addition to the protein levels examined in Example 3 by immunoblot, CUGBP1 protein levels is also examined, as described in Orengo et al.

ii)

DMPK-CTG mice also are evaluated by a treadmill test as described in Orengo et al. Briefly, mice are placed on a treadmill with rear electrical shock (e.g. AccuPacer Treadmill, AccuScan Instruments Inc.). The speed is increased by 2 m/min every two minutes for 30 minutes or until mouse is unable to run.

SEQUENCE LISTING

SEQ ID NO: 1 = The amino acid sequence of the human MBNL1 protein, isoform a (GenBank Accession No. NP_066368.2).
MAVSVTPIRDTKWLTLEVCREFQRGTCSRPDTECKFAHPSKSCQVENGRV
IACFDSLKGRCSRENCKYLHPPPHLKTQLEINGRNNLIQQKNMAMLAQQM
QLANAMMPGAPLQPVPMFSVAPSLATNASAAAFNPYLGPVSPSLVPAEIL
PTAPMLVTGNPGVPVPAAAAAAAQKLMRTDRLEVCREYQRGNCNRGENDC
RFAHPADSTMIDTNDNTVTVCMDYIKGRCSREKCKYFHPPAHLQAKIKAA
QYQVNQAAAAQAAATAAAMGIPQAVLPPLPKRPALEKTNGATAVFNTGIF
QYQQALANMQLQQHTAFLPPGSILCMTPATSVVPMVHGATPATVSAATTS
ATSVPFAATATANQIPIISAEHLTSHKYVTQM SEQ ID NO: 2 = The amino acid sequence of the human MBNL1 protein, isoform b (GenBank Accession No. NP_997175.1).
MAVSVTPIRDTKWLTLEVCREFQRGTCSRPDTECKFAHPSKSCQVENGRV
IACFDSLKGRCSRENCKYLHPPPHLKTQLEINGRNNLIQQKNMAMLAQQM
QLANAMMPGAPLQPVPMFSVAPSLATNASAAAFNPYLGPVSPSLVPAEIL
PTAPMLVTGNPGVPVPAAAAAAAQKLMRTDRLEVCREYQRGNCNRGENDC
RFAHPADSTMIDTNDNTVTVCMDYIKGRCSREKCKYFHPPAHLQAKIKAA
QYQVNQAAAAQAAATAAAMGIPQAVLPPLPKRPALEKTNGATAVFNTGIF
QYQQALANMQLQQHTAFLPPVPMVHGATPATVSAATTSATSVPFAATATA
NQIPIISAEHLTSHKYVTQM SEQ ID NO: 3 = The amino acid sequence of the human MBNL1 protein, isoform c (GenBank Accession No. NP_997176.1).
MAVSVTPIRDTKWLTLEVCREFQRGTCSRPDTECKFAHPSKSCQVENGRV
IACFDSLKGRCSRENCKYLHPPPHLKTQLEINGRNNLIQQKNMAMLAQQM
QLANAMMPGAPLQPVPMFSVAPSLATNASAAAFNPYLGPVSPSLVPAEIL
PTAPMLVTGNPGVPVPAAAAAAAQKLMRTDRLEVCREYQRGNCNRGENDC
RFAHPADSTMIDTNDNTVTVCMDYIKGRCSREKCKYFHPPAHLQAKIKAA
QYQVNQAAAAQAAATAAAMTQSAVKSLKRPLEATFDLGIPQAVLPPLPKR
PALEKTNGATAVFNTGIFQYQQALANMQLQQHTAFLPPVPMVHGATPATV
SAATTSATSVPFAATATANQIPIISAEHLTSHKYVTQM SEQ ID NO: 4 = The amino acid sequence of the human MBNL1 protein, isoform d (GenBank Accession No. NP_997177.1).
MAVSVTPIRDTKWLTLEVCREFQRGTCSRPDTECKFAHPSKSCQVENGRV
IACFDSLKGRCSRENCKYLHPPPHLKTQLEINGRNNLIQQKNMAMLAQQM
QLANAMMPGAPLQPVVCREYQRGNCNRGENDCRFAHPADSTMIDTNDNTV
TVCMDYIKGRCSREKCKYFHPPAHLQAKIKAAQYQVNQAAAAQAAATAAA
MGIPQAVLPPLPKRPALEKTNGATAVFNTGIFQYQQALANMQLQQHTAFL
PPVPMVHGATPATVSAATTSATSVPFAATATANQIPIISAEHLTSHKYVT
QM SEQ ID NO: 5 = The amino acid sequence of the human MBNL1 protein, isoform e (GenBank Accession No. NP_997178.1).
MAVSVTPIRDTKWLTLEVCREFQRGTCSRPDTECKFAHPSKSCQVENGRV
IACFDSLKGRCSRENCKYLHPPPHLKTQLEINGRNNLIQQKNMAMLAQQM
QLANAMMPGAPLQPVVCREYQRGNCNRGENDCRFAHPADSTMIDTNDNTV

SEQUENCE LISTING

TVCMDYIKGRCSREKCKYFHPPAHLQAKIKAAQYQVNQAAAAQAAATAAA

MGIPQAVLPPLPKRPALEKTNGATAVFNTGIFQYQQALANMQLQQHTAFL

PPGSILCMTPATSVVPMVHGATPATVSAATTSATSVPFAATATANQIPII

SAEHLTSHKYVTQM

SEQ ID NO: 6 = The amino acid sequence of the human MBNL1 protein, isoform f (GenBank Accession No. NP_997179.1).
MAVSVTPIRDTKWLTLEVCREFQRGTCSRPDTECKFAHPSKSCQVENGRV

IACFDSLKGRCSRENCKYLHPPPHLKTQLEINGRNNLIQQKNMAMLAQQM

QLANAMMPGAPLQPVPMFSVAPSLATNASAAAFNPYLGPVSPSLVPAEIL

PTAPMLVTGNPGVPVPAAAAAAQKLMRTDRLEVCREYQRGNCNRGENDC

RFAHPADSTMIDTNDNTVTVCMDYIKGRCSREKCKYFHPPAHLQAKIKAA

QYQVNQAAAAQAAATAAAMFPWCTVLRQPLCPQQQHLPQVFPSLQQPQPT

SPILDASTLLGATSCPAAAGKMIPIISAEHLTSHKYVTQM

SEQ ID NO: 7 = The amino acid sequence of the human MBNL1 protein, isoform g (GenBank Accession No. NP_997180.1).
MAVSVTPIRDTKWLTLEVCREFQRGTCSRPDTECKFAHPSKSCQVENGRV

IACFDSLKGRCSRENCKYLHPPPHLKTQLEINGRNNLIQQKNMAMLAQQM

QLANAMMPGAPLQPVPMFSVAPSLATNASAAAFNPYLGPVSPSLVPAEIL

PTAPMLVTGNPGVPVPAAAAAAQKLMRTDRLEVCREYQRGNCNRGENDC

RFAHPADSTMIDTNDNTVTVCMDYIKGRCSREKCKYFHPPAHLQAKIKAA

QYQVNQAAAAQAAATAAAMGIPQAVLPPLPKRPALEKTNGATAVFNTGIF

QYQQALANMQLQQHTAFLPPGSILCMTPATSVDTHNICRTSD

SEQ ID NO: 8 = Human DMPK (GenBank Accession No. BC062553)
MSAEVRLRRLQQLVLDPGFLGLEPLLDLLLGVHQELGASELAQDKYVADF

LQWAEPIVVRLKEVRLQRDDFEILKVIGRGAFSEVAVVKMKQTGQVYAMK

IMNKWDMLKRGEVSCFREERDVLVNGDRRWITQLHFAFQDENYLYLVMEY

YVGGDLLTLLSKFGERIPAEMARFYLAEIVMAIDSVHRLGYVHRDIKPDN

ILLDRCGHIRLADFGSCLKLRADGTVRSLVAVGTPDYLSPEILQAVGGGP

GTGSYGPECDWWALGVFAYEMFYGQTPFYADSTAETYGKIVHYKEHLSLP

LVDEGVPEEARDFIQRLLCPPETRLGRGGAGDFRTHPFFFGLDWDGLRDS

VPPFTPDFEGATDTCNFDLVEDGLTAMVSGGGETLSDIREGAPLGVHLPF

VGYSYSCMALRDSEVPGPTPMELEAEQLLEPHVQAPSLEPSVSPQDETAE

VAVPAAVPAAEAEAEVTLRELQEALEEEVLTRQSLSREMEAIRTDNQNFA

SQLREAEARNRDLEAHVRQLQERMELLQAEGATAVTGVPSPRATDPPSHL

DGPPAVAVGQCPLVGPGPMHRRHLLLPARVPRPGLSEALSLLLFAVVLSR

AAALGCIGLVAHAGQLTAVWRRPGAARAP

SEQ ID NO: 9 = exemplary antisense oligonucleotide that hybridizes to DMPK
AGC AGCAGCAG<u>CAG</u>
[in which the underlined positions are LNA nucleotides and the remaining nucleotides are phosphorothioate nucleotides].

SEQ ID NO: 10 = exemplary antisense oligonucleotide that hybridizes to DMPK
<u>CAG</u> CAGCAGCAGC<u>AGC</u>
[in which the underlined positions are LNA nucleotides and the remaining positions are phosphorothioate nucleotides].

SEQ ID NO: 11 = exemplary antisense oligonucleotide thathybridizes to DMPK
<u>AGC</u> AGCAGCAG<u>CAG</u>
[in which the underlined positions are 2'-O-methoxyethyl nucleotides and the remaining nucleotides are phosphorothioate nucleotides].

SEQ ID NO: 12 = exemplary antisense oligonucleotide that hybridizes to DMPK
<u>AGC</u> AG<u>CAG</u>CAG<u>CAG</u>
[in which the underlined positions are 2'-O-methoxyethyl nucleotides and the remaining nucleotides are phosphorothioate nucleotides].

SEQ ID NO: 13 = exemplary 3E10 Variable Heavy Chain
EVQLVESGGGLVKPGGSRKLSCAASGFTFSNYGMHWVRQAPEKGLEWVAY

ISSGSSTIYYADTVKGRFTISRDNAKNTLFLQMTSLRSEDTAMYYCARRG

LLLDYWGQGTTLTVSS

SEQ ID NO: 14 = exemplary 3E10 Variable Light Chain
DIVLTQSPASLAVSLGQRATISCRASKSVSTSSYSMHWYQQKPGQPPKL

LIKYASYLESGVPARFSGSGSGTDFHLNIHPVEEEDAATYYCQHSREFPW

TFGGGTKLELK

SEQ ID NO: 15 = GS3 linker
GGGGSGGGGSGGGGS

SEQ ID NO: 16 = variable heavy chain CDR1 of exemplary 3E10 molecule
NYGMH

SEQ ID NO: 17 = variable heavy chain CDR2 of exemplary 3E10 molecule
YISSGSSTIYYADTVKG SEQ ID NO: 18 = variable heavy chain CDR3 of exemplary 3E10 molecule
RGLLLDY SEQ ID NO: 19 = variable light chain CDR1 of exemplary 3E10 molecule
RASKSVSTSSYSMH SEQ ID NO: 20 = variable light chain CDR2 of exemplary 3E10 molecule
YASYLES SEQ ID NO: 21 - variable light chain CDR3 of exemplary 3E10 molecule
QHSREFPWT SEQ ID NO: 22-morpholino oligonucleotide
AGCAGCAGCAGCAGCAGCAGCA SEQ ID NO: 23-antisense oligonucleotide
CAGCAGCAGCAGCAGCAGCAG SEQ ID NO: 24-DMPK transcript variant 1 (GenBank No. 001081563.1)
GCCACAAGCCTCCACCCCAGCTGGTCCCCACCCAGGCTGCCCAGTTTAA

CATTCCTAGTCATAGGACCTTGACTTCTGAGAGGCCTGATTGTCATCTGT

AAATAAGGGGTAGGACTAAAGCACTCCTCCTGGAGGACTGAGAGATGGGC

SEQUENCE LISTING

```
TGGACCGGAGCACTTGAGTCTGGGATATGTGACCATGCTACCTTTGTCTC

CCTGTCCTGTTCCTTCCCCCAGCCCCAAATCCAGGGTTTTCCAAAGTGTG

GTTCAAGAACCACCTGCATCTGAATCTAGAGGTACTGGATACAACCCCAC

GTCTGGGCCGTTACCCAGGACATTCTACATGAGAACGTGGGGGTGGGGCC

CTGGCTGCACCTGAACTGTCACCTGGAGTCAGGGTGGAAGGTGGAAGAAC

TGGGTCTTATTTCCTTCTCCCCTTGTTCTTTAGGGTCTGTCCTTCTGCAG

ACTCCGTTACCCCACCCTAACCATCCTGCACACCCTTGGAGCCCTCTGGG

CCAATGCCCTGTCCCGCAAAGGGCTTCTCAGGCATCTCACCTCTATGGGA

GGGCATTTTTGGCCCCCAGAACCTTACACGGTGTTTATGTGGGGAAGCCC

CTGGGAAGCAGACAGTCCTAGGGTGAAGCTGAGAGGCAGAGAGAAGGGGA

GACAGACAGAGGGTGGGGCTTTCCCCCTTGTCTCCAGTGCCCTTTCTGGT

GACCCTCGGTTCTTTTCCCCCACCACCCCCCAGCGGAGCCCATCGTGGT

GAGGCTTAAGGAGGTCCGACTGCAGAGGGACGACTTCGAGATTCTGAAGG

TGATCGGACGCGGGGCGTTCAGCGAGGTAGCGGTAGTGAAGATGAAGCAG

ACGGGCCAGGTGTATGCCATGAAGATCATGAACAAGTGGGACATGCTGAA

GAGGGGCGAGGTGTCGTGCTTCCGTGAGGAGAGGGACGTGTTGGTGAATG

GGGACCGGCGGTGGATCACGCAGCTGCACTTCGCCTTCCAGGATGAGAAC

TACCTGTACCTGGTCATGGAGTATTACGTGGGCGGGGACCTGCTGACACT

GCTGAGCAAGTTTGGGGAGCGGATTCCGGCCGAGATGGCGCGCTTCTACC

TGGCGGAGATTGTCATGGCCATAGACTCGGTGCACCGGCTTGGCTACGTG

CACAGGGACATCAAACCCGACAACATCCTGCTGGACCGCTGTGGCCACAT

CCGCCTGGCCGACTTCGGCTCTTGCCTCAAGCTGCGGGCAGATGGAACGG

TGCGGTCGCTGGTGGCTGTGGGCACCCCAGACTACCTGTCCCCCGAGATC

CTGCAGGCTGTGGGCGGTGGGCCTGGGACAGGCAGCTACGGGCCCGAGTG

TGACTGGTGGGCGCTGGGTGTATTCGCCTATGAAATGTTCTATGGGCAGA

CGCCCTTCTACGCGGATTCCACGGCGGAGACCTATGGCAAGATCGTCCAC

TACAAGGAGCACCTCTCTCTGCCGCTGGTGGACGAAGGGGTCCCTGAGGA

GGCTCGAGACTTCATTCAGCGGTTGCTGTGTCCCCCGGAGACACGGCTGG

GCCGGGGTGGAGCAGGCGACTTCCGGACACATCCCTTCTTCTTTGGCCTC

GACTGGGATGGTCTCCGGGACAGCGTGCCCCCCTTTACACCGGATTTCGA

AGGTGCCACCGACACATGCAACTTCGACTTGGTGGAGGACGGGCTCACTG

CCATGGTGAGCGGGGCGGGGAGACACTGTCGGACATTCGGGAAGGTGCG

CCGCTAGGGGTCCACCTGCCTTTTGTGGGCTACTCCTACTCCTGCATGGC

CCTCAGGGACAGTGAGGTCCCAGGCCCCACACCCATGGAACTGGAGGCG

AGCAGCTGCTTGAGCCACACGTGCAAGCGCCCAGCCTGGAGCCCTCGGTG

TCCCCACAGGATGAAACAGCTGAAGTGGCAGTTCCAGCGGCTGTCCCTGC

GGCAGAGGCTGAGGCCGAGGTGACGCTGCGGGAGCTCCAGGAAGCCCTGG

AGGAGGAGGTGCTCACCCGGCAGAGCCTGAGCCGGGAGATGGAGGCCATC

CGCACGGACAACCAGAACTTCGCCAGTCAACTACGCGAGGCAGAGGCTCG
```

```
GAACCGGGACCTAGAGGCACACGTCCGGCAGTTGCAGGAGCGGATGGAGT

TGCTGCAGGCAGAGGGAGCCACAGCTGTCACGGGGGTCCCCAGTCCCCGG

GCCACGGATCCACCTTCCCATCTAGATGGCCCCCGGCCGTGGCTGTGGG

CCAGTGCCCGCTGGTGGGGCCAGGCCCCATGCACCGCCGCCACCTGCTGC

TCCCTGCCAGGGTCCCTAGGCCTGGCCTATCGGAGGCGCTTTCCCTGCTC

CTGTTCGCCGTTGTTCTGTCTCGTGCCGCCGCCCTGGGCTGCATTGGGTT

GGTGGCCCACGCCGGCCAACTCACCGCAGTCTGGCGCCGCCCAGGAGCCG

CCCGCGCTCCCTGAACCCTAGAACTGTCTTCGACTCCGGGGCCCCGTTGG

AAGACTGAGTGCCCGGGGCACGGCACAGAAGCCGCGCCCACCGCCTGCCA

GTTCACAACCGCTCCGAGCGTGGGTCTCCGCCCAGCTCCAGTCCTGTGAT

CCGGGCCCGCCCCCTAGCGGCCGGGGAGGGAGGGGCCGGGTCCGCGGCCG

GCGAACGGGCTCGAAGGGTCCTTGTAGCCGGGAATGCTGCTGCTGCTGC

TGCTGCTGCTGCTGCTGCTGCTGCTGCTGCTGCTGCTGCTGCTGCTGGGG

GGATCACAGACCATTTCTTTCTTTCGGCCAGGCTGAGGCCCTGACGTGGA

TGGGCAAACTGCAGGCCTGGGAAGGCAGCAAGCCGGGCCGTCCGTGTTCC

ATCCTCCACGCACCCCCACCTATCGTTGGTTCGCAAAGTGCAAAGCTTTC

TTGTGCATGACGCCCTGCTCTGGGGAGCGTCTGGCGCGATCTCTGCCTGC

TTACTCGGGAAATTTGCTTTTGCCAAACCCGCTTTTTCGGGGATCCCGCG

CCCCCCTCCTCACTTGCGCTGCTCTCGGAGCCCCAGCCGGCTCCGCCCGC

TTCGGCGGTTTGGATATTTATTGACCTCGTCCTCCGACTCGCTGACAGGC

TACAGGACCCCAACAACCCCAATCCACGTTTTGGATGCACTGAGACCCC

GACATTCCTCGGTATTTATTGTCTGTCCCCACCTAGGACCCCCACCCCCG

ACCCTCGCGAATAAAGGCCCTCCATCTGCCCAAAAAAAAAAAAAAAAAA

AAAAAAAAAA

SEQ ID NO: 25-DMPK transcript variant 2
(GenBank NM_004409.3)
AGGGGGGCTGGACCAAGGGGTGGGGAGAAGGGGAGGAGGCCTCGGCCGGC

CGCAGAGAGAAGTGGCCAGAGAGGCCCAGGGGACAGCCAGGGACAGGCAG

ACATGCAGCCAGGGCTCCAGGGCTGGACAGGGGCTGCCAGGCCCTGTGA

CAGGAGGACCCCGAGCCCCGGCCCGGGAGGGGCCATGGTGCTGCCTGT

CCAACATGTCAGCCGAGGTGCGGCTGAGGCGGCTCCAGCAGCTGGTGTTG

GACCCGGGCTTCCTGGGGCTGGAGCCCCTGCTCGACCTTCTCCTGGGCGT

CCACCAGGAGCTGGGCGCCTCCGAACTGGCCCAGGACAAGTACGTGGCCG

ACTTCTTGCAGTGGGCGGAGCCCATCGTGGTGAGGCTTAAGGAGGTCCGA

CTGCAGAGGGACGACTTCGAGATTCTGAAGGTGATCGGACGCGGGGCGTT

CAGCGAGGTAGCGGTAGTGAAGATGAAGCAGACGGGCCAGGTGTATGCCA

TGAAGATCATGAACAAGTGGGACATGCTGAAGAGGGGCGAGGTGTCGTGC

TTCCGTGAGGAGAGGGACGTGTTGGTGAATGGGGACCGGCGGTGGATCAC

GCAGCTGCACTTCGCCTTCCAGGATGAGAACTACCTGTACCTGGTCATGG
```

AGTATTACGTGGGCGGGGACCTGCTGACACTGCTGAGCAAGTTTGGGGAG

CGGATTCCGGCCGAGATGGCGCGCTTCTACCTGGCGGAGATTGTCATGGC

CATAGACTCGGTGCACCGGCTTGGCTACGTGCACAGGGACATCAAACCCG

ACAACATCCTGCTGGACCGCTGTGGCCACATCCGCCTGGCCGACTTCGGC

TCTTGCCTCAAGCTGCGGGCAGATGGAACGGTGCGGTCGCTGGTGGCTGT

GGGCACCCCAGACTACCTGTCCCCCGAGATCCTGCAGGCTGTGGGCGGTG

GGCCTGGGACAGGCAGCTACGGGCCCGAGTGTGACTGGTGGGCGCTGGGT

GTATTCGCCTATGAAATGTTCTATGGGCAGACGCCCTTCTACGCGGATTC

CACGGCGGAGACCTATGGCAAGATCGTCCACTACAAGGAGCACCTCTCTC

TGCCGCTGGTGGACGAAGGGGTCCCTGAGGAGGCTCGAGACTTCATTCAG

CGGTTGCTGTGTCCCCCGGAGACACGGCTGGGCCGGGGTGGAGCAGGCGA

CTTCCGGACACATCCCTTCTTCTTTGGCCTCGACTGGGATGGTCTCCGGG

ACAGCGTGCCCCCCTTTACACCGGATTTCGAAGGTGCCACCGACACATGC

AACTTCGACTTGGTGGAGGACGGGCTCACTGCCATGGAGACACTGTCGGA

CATTCGGGAAGGTGCGCCGCTAGGGGTCCACCTGCCTTTTGTGGGCTACT

CCTACTCCTGCATGGCCCTCAGGGACAGTGAGGTCCCAGGCCCACACCC

ATGGAACTGGAGGCCGAGCAGCTGCTTGAGCCACACGTGCAAGCGCCCAG

CCTGGAGCCCTCGGTGTCCCCACAGGATGAAACAGCTGAAGTGGCAGTTC

CAGCGGCTGTCCCTGCGGCAGAGGCTGAGGCCGAG

GTGACGCTGCGGGAGCTCCAGGAAGCCCTGGAGGAGGAGGTGCTCACCCG

GCAGAGCCTGAGCCGGGAGATGGAGGCCATCCGCACGGACAACCAGAACT

TCGCCAGTCAACTACGCGAGGCAGAGGCTCGGAACCGGGACCTAGAGGCA

CACGTCCGGCAGTTGCAGGAGCGGATGGAGTTGCTGCAGGCAGAGGGAGC

CACAGCTGTCACGGGGGTCCCCAGTCCCCGGGCCACGGATCCACCTTCCC

ATCTAGATGGCCCCCGGCCGTGGCTGTGGGCCAGTGCCCGCTGGTGGGG

CCAGGCCCCATGCACCGCCGCCACCTGCTGCTCCCTGCCAGGGTCCCTAG

GCCTGGCCTATCGGAGGCGCTTTCCCTGCTCCTGTTCGCCGTTGTTCTGT

CTCGTGCCGCCGCCCTGGGCTGCATTGGGTTGGTGGCCCACGCCGGCCAA

CTCACCGCAGTCTGGCGCCGCCCAGGAGCCGCCCGCGCTCCCTGAACCCT

AGAACTGTCTTCGACTCCGGGGCCCCGTTGGAAGACTGAGTGCCCGGGGC

ACGGCACAGAAGCCGCGCCCACCGCCTGCCAGTTCACAACCGCTCCGAGC

GTGGGTCTCCGCCCAGCTCCAGTCCTGTGATCCGGGCCCGCCCCCTAGCG

GCCGGGGAGGGAGGGGCCGGGTCCGCGGCCGGCGAACGGGGCTCGAAGGG

TCCTTGTAGCCGGGAATGCTGCTGCTGCTGCTGCTGCTGCTGCTGCTGCT

GCTGCTGCTGCTGCTGCTGCTGCTGGGGGGATCACAGACCATTTCTT

TCTTTCGGCCAGGCTGAGGCCCTGACGTGGATGGGCAAACTGCAGGCCTG

GGAAGGCAGCAAGCCGGGCCGTCCGTGTTCCATCCTCCACGCACCCCCAC

CTATCGTTGGTTCGCAAAGTGCAAAGCTTTCTTGTGCATGACGCCCTGCT

CTGGGGAGCGTCTGGCGCGATCTCTGCCTGCTTACTCGGGAAATTTGCTT

TTGCCAAACCCGCTTTTTCGGGGATCCCGCGCCCCCCTCCTCACTTGCGC

TGCTCTCGGAGCCCCAGCCGGCTCCGCCCGCTTCGGCGGTTTGGATATTT

ATTGACCTCGTCCTCCGACTCGCTGACAGGCTACAGGACCCCCAACAACC

CCAATCCACGTTTTGGATGCACTGAGACCCCGACATTCCTCGGTATTTAT

TGTCTGTCCCCACCTAGGACCCCCACCCCCGACCCTCGCGAATAAAAGGC

CCTCCATCTGCCCAAAAAAAAAAAAAAAAAA

SEQ ID NO: 26-DMPK transcript variant 3
(GenBank NM_001081560.1)
AGGGGGGCTGGACCAAGGGGTGGGAGAAGGGGAGGAGGCCTCGGCCGGC

CGCAGAGAGAAGTGGCCAGAGAGGCCCAGGGGACAGCCAGGGACAGGCAG

ACATGCAGCCAGGGCTCCAGGGCCTGGACAGGGGCTGCCAGGCCCTGTGA

CAGGAGGACCCCGAGCCCCCGGCCCGGGGAGGGGCCATGGTGCTGCCTGT

CCAACATGTCAGCCGAGGTGCGGCTGAGGCGGCTCCAGCAGCTGGTGTTG

GACCCGGGCTTCCTGGGGCTGGAGCCCCTGCTCGACCTTCTCCTGGGCGT

CCACCAGGAGCTGGGCGCCTCCGAACTGGCCCAGGACAAGTACGTGGCCG

ACTTCTTGCAGTGGGCGGAGCCCATCGTGGTGAGGCTTAAGGAGGTCCGA

CTGCAGAGGGACGACTTCGAGATTCTGAAGGTGATCGGACGCGGGGCGTT

CAGCGAGGTAGCGGTAGTGAAGATGAAGCAGACGGGCCAGGTGTATGCCA

TGAAGATCATGAACAAGTGGGACATGCTGAAGAGGGCGAGGTGTCGTGC

TTCCGTGAGGAGAGGGACGTGTTGGTGAATGGGACCGGCGGTGGATCAC

GCAGCTGCACTTCGCCTTCCAGGATGAGAACTACCTGTACCTGGTCATGG

AGTATTACGTGGGCGGGGACCTGCTGACACTGCTGAGCAAGTTTGGGGAG

CGGATTCCGGCCGAGATGGCGCGCTTCTACCTGGCGGAGATTGTCATGGC

CATAGACTCGGTGCACCGGCTTGGCTACGTGCACAGGGACATCAAACCCG

ACAACATCCTGCTGGACCGCTGTGGCCACATCCGCCTGGCCGACTTCGGC

TCTTGCCTCAAGCTGCGGGCAGATGGAACGGTGCGGTCGCTGGTGGCTGT

GGGCACCCCAGACTACCTGTCCCCCGAGATCCTGCAGGCTGTGGGCGGTG

GGCCTGGGACAGGCAGCTACGGGCCCGAGTGTGACTGGTGGGCGCTGGGT

GTATTCGCCTATGAAATGTTCTATGGGCAGACGCCCTTCTACGCGGATTC

CACGGCGGAGACCTATGGCAAGATCGTCCACTACAAGGAGCACCTCTCTC

TGCCGCTGGTGGACGAAGGGGTCCCTGAGGAGGCTCGAGACTTCATTCAG

CGGTTGCTGTGTCCCCCGGAGACACGGCTGGGCCGGGGTGGAGCAGGCGA

CTTCCGGACACATCCCTTCTTCTTTGGCCTCGACTGGGATGGTCTCCGGG

ACAGCGTGCCCCCCTTTACACCGGATTTCGAAGGTGCCACCGACACATGC

AACTTCGACTTGGTGGAGGACGGGCTCACTGCCATGGAGACACTGTCGGA

CATTCGGGAAGGTGCGCCGCTAGGGGTCCACCTGCCTTTTGTGGGCTACT

CCTACTCCTGCATGGCCCTCAGGGACAGTGAGGTCCCAGGCCCACACCC

ATGGAACTGGAGGCCGAGCAGCTGCTTGAGCCACACGTGCAAGCGCCCAG

CCTGGAGCCCTCGGTGTCCCCACAGGATGAAACAGCTGAAGTGGCAGTTC

SEQUENCE LISTING

CAGCGGCTGTCCCTGCGGCAGAGGCTGAGGCCGAGGTGACGCTGCGGGAG

CTCCAGGAAGCCCTGGAGGAGGAGGTGCTCACCCGGCAGAGCCTGAGCCG

GGAGATGGAGGCCATCCGCACGGACAACCAGAACTTCGCCAGTCAACTAC

GCGAGGCAGAGGCTCGGAACCGGGACCTAGAGGCACACGTCCGGCAGTTG

CAGGAGCGGATGGAGTTGCTGCAGGCAGAGGGAGCCACAGCTGTCACGGG

GGTCCCCAGTCCCCGGGCCACGGATCCACCTTCCCATCTAGATGGCCCCC

CGGCCGTGGCTGTGGGCCAGTGCCCGCTGGTGGGGCCAGGCCCCATGCAC

CGCCGCCACCTGCTGCTCCCTGCCAGGGTCCCTAGGCCTGGCCTATCGGA

GGCGCTTTCCCTGCTCCTGTTCGCCGTTGTTCTGTCTCGTGCCGCCGCCC

TGGGCTGCATTGGGTTGGTGGCCCACGCCGGCCAACTCACCGCAGTCTGG

CGCCGCCCAGGAGCCGCCCGCGCTCCCTGAACCCTAGAACTGTCTTCGAC

TCCGGGGCCCCGTTGGAAGACTGAGTGCCCGGGGCACGGCACAGAAGCCG

CGCCCACCGCCTGCCAGTTCACAACCGCTCCGAGCGTGGGTCTCCGCCCA

GCTCCAGTCCTGTGATCCGGGCCCGCCCCCTAGCGGCCGGGGAGGGAGGG

GCCGGGTCCGCGGCCGGCGAACGGGGCTCGAAGGGTCCTTGTAGCCGGGA

ATGCTGCTGCTGCTGCTGCTGCTGCTGCTGCTGCTGCTGCTGCTGCTGCT

GCTGCTGCTGGGGGGATCACAGACCATTTCTTTCTTTCGGCCAGGCT

GAGGCCCTGACGTGGATGGGCAAACTGCAGGCCTGGGAAGGCAGCAAGCC

GGGCCGTCCGTGTTCCATCCTCCACGCACCCCCACCTATCGTTGGTTCGC

AAAGTGCAAAGCTTTCTTGTGCATGACGCCCTGCTCTGGGGAGCGTCTGG

CGCGATCTCTGCCTGCTTACTCGGGAAATTTGCTTTTGCCAAACCCGCTT

TTTCGGGGATCCCGCGCCCCCCTCCTCACTTGCGCTGCTCTCGGAGCCCC

AGCCGGCTCCGCCCGCTTCGGCGGTTTGGATATTTATTGACCTCGTCCTC

CGACTCGCTGACAGGCTACAGGACCCCCAACAACCCCAATCCACGTTTTG

GATGCACTGAGACCCCGACATTCCTCGGTATTTATTGTCTGTCCCCACCT

AGGACCCCCACCCCCGACCCTCGCGAATAAAAGGCCCTCCATCTGCCCAA

AAAAAAAAAAAAAAAAAAAAAAAAAAA

SEQ ID NO: 27-DMPK transcript variant 4
(GenBank NM_001081562.1)
AGGGGGGCTGGACCAAGGGTGGGGAGAAGGGGAGGAGGCCTCGGCCGGC

CGCAGAGAGAAGTGGCCAGAGAGGCCCAGGGGACAGCCAGGGACAGGCAG

ACATGCAGCCAGGGCTCCAGGGCCTGGACAGGGGCTGCCAGGCCCTGTGA

CAGGAGGACCCCGAGCCCCCGGCCCGGGGAGGGGCCATGGTGCTGCCTGT

CCAACATGTCAGCCGAGGTGCGGCTGAGGCGGCTCCAGCAGCTGGTGTTG

GACCCGGGCTTCCTGGGGCTGGAGCCCCTGCTCGACCTTCTCCTGGGCGT

CCACCAGGAGCTGGGCGCCTCCGAACTGGCCCAGGACAAGTACGTGGCCG

ACTTCTTGCAGTGGGCGGAGCCCATCGTGGTGAGGCTTAAGGAGGTCCGA

CTGCAGAGGGACGACTTCGAGATTCTGAAGGTGATCGGACGCGGGCGTT

CAGCGAGGTAGCGGTAGTGAAGATGAAGCAGACGGGCCAGGTGTATGCCA

TGAAGATCATGAACAAGTGGGACATGCTGAAGAGGGGCGAGGTGTCGTGC

TTCCGTGAGGAGAGGGACGTGTTGGTGAATGGGGACCGGCGGTGGATCAC

GCAGCTGCACTTCGCCTTCCAGGATGAGAACTACCTGTACCTGGTCATGG

AGTATTACGTGGGCGGGGACCTGCTGACACTGCTGAGCAAGTTTGGGGAG

CGGATTCCGGCCGAGATGGCGCGCTTCTACCTGGCGGAGATTGTCATGGC

CATAGACTCGGTGCACCGGCTTGGCTACGTGCACAGGGACATCAAACCCG

ACAACATCCTGCTGGACCGCTGTGGCCACATCCGCCTGGCCGACTTCGGC

TCTTGCCTCAAGCTGCGGGCAGATGGAACGGTGCGGTCGCTGGTGGCTGT

GGGCACCCCAGACTACCTGTCCCCCGAGATCCTGCAGGCTGTGGGCGGTG

GGCCTGGGACAGGCAGCTACGGGCCCGAGTGTGACTGGTGGGCGCTGGGT

GTATTCGCCTATGAAATGTTCTATGGGCAGACGCCCTTCTACGCGGATTC

CACGGCGGAGACCTATGGCAAGATCGTCCACTACAAGGAGCACCTCTCTC

TGCCGCTGGTGGACGAAGGGGTCCCTGAGGAGGCTCGAGACTTCATTCAG

CGGTTGCTGTGTCCCCCGGAGACACGGCTGGGCCGGGGTGGAGCAGGCGA

CTTCCGGACACATCCCTTCTTCTTTGGCCTCGACTGGGATGGTCTCCGGG

ACAGCGTGCCCCCCTTTACACCGGATTTCGAAGGTGCCACCGACACATGC

AACTTCGACTTGGTGGAGGACGGGCTCACTGCCATGGAGACACTGTCGGA

CATTCGGGAAGGTGCGCCGCTAGGGGTCCACCTGCCTTTTGTGGGCTACT

CCTACTCCTGCATGGCCCTCAGGGACAGTGAGGTCCCAGGCCCCACACCC

ATGGAACTGGAGGCCGAGCAGCTGCTTGAGCCACACGTGCAAGCGCCCAG

CCTGGAGCCCTCGGTGTCCCCACAGGATGAAACAGCTGAAGTGGCAGTTC

CAGCGGCTGTCCCTGCGGCAGAGGCTGAGGCCGAGGTGACGCTGCGGGAG

CTCCAGGAAGCCCTGGAGGAGGAGGTGCTCACCCGGCAGAGCCTGAGCCG

GGAGATGGAGGCCATCCGCACGGACAACCAGAACTTCGCCAGTCAACTAC

GCGAGGCAGAGGCTCGGAACCGGGACCTAGAGGCACACGTCCGGCAGTTG

CAGGAGCGGATGGAGTTGCTGCAGGCAGAGGGAGCCACAGCTGTCACGGG

GGTCCCCAGTCCCCGGGCCACGGATCCACCTTCCCATATGGCCCCCCGGC

CGTGGCTGTGGGCCAGTGCCCGCTGGTGGGGCCAGGCCCCATGCACCGCC

GCCACCTGCTGCTCCCTGCCAGGGTCCCTAGGCCTGGCCTATCGGAGGCG

CTTTCCCTGCTCCTGTTCGCCGTTGTTCTGTCTCGTGCCGCCGCCCTGGG

CTGCATTGGGTTGGTGGCCCACGCCGGCCAACTCACCGCAGTCTGGCGCC

GCCCAGGAGCCGCCCGCGCTCCCTGAACCCTAGAACTGTCTTCGACTCCG

GGGCCCCGTTGGAAGACTGAGTGCCCGGGGCACGGCACAGAAGCCGCGCC

CACCGCCTGCCAGTTCACAACCGCTCCGAGCGTGGGTCTCCGCCCAGCTC

CAGTCCTGTGATCCGGGCCCGCCCCCTAGCGGCCGGGGAGGGAGGGGCCG

GGTCCGCGGCCGGCGAACGGGGCTCGAAGGGTCCTTGTAGCCGGGAATGC

TGCTGCTGCTGCTGCTGCTGCTGCTGCTGCTGCTGCTGCTGCTGCTGCTG

CTGCTGCTGGGGGGATCACAGACCATTTCTTTCTTTCGGCCAGGCTGAGG

CCCTGACGTGGATGGGCAAACTGCAGGCCTGGGAAGGCAGCAAGCCGGGC

SEQUENCE LISTING

```
CGTCCGTGTTCCATCCTCCACGCACCCCCACCTATCGTTGGTTCGCAAAG

TGCAAAGCTTTCTTGTGCATGACGCCCTGCTCTGGGGAGCGTCTGGCGCG

ATCTCTGCCTGCTTACTCGGGAAATTTGCTTTTGCCAAACCCGCTTTTTC

GGGGATCCCGCGCCCCCTCCTCACTTGCGCTGCTCTCGGAGCCCCAGCC

GGCTCCGCCCGCTTCGGCGGTTTGGATATTTATTGACCTCGTCCTCCGAC

TCGCTGACAGGCTACAGGACCCCCAACAACCCCAATCCACGTTTTGGATG

CACTGAGACCCCGACATTCCTCGGTATTTATTGTCTGTCCCCACCTAGGA

CCCCCACCCCCGACCCTCGCGAATAAAAGGCCCTCCATCTGCCCAAAAAA

AAAAAAAAAAAAAAAAAAAAAA
```

INCORPORATION BY REFERENCE

All publications and patents mentioned herein are hereby incorporated by reference in their entirety as if each individual publication or patent was specifically and individually indicated to be incorporated by reference.

While specific embodiments of the subject disclosure have been discussed, the above specification is illustrative and not restrictive. Many variations of the disclosure will become apparent to those skilled in the art upon review of this specification and the claims below. The full scope of the disclosure should be determined by reference to the claims, along with their full scope of equivalents, and the specification, along with such variations.

We claim:

1. A conjugate comprising
  a) an antisense oligonucleotide that hybridizes to a DMPK transcript wherein the oligonucleotide is capable of:
    i) mediating RNase H-mediated degradation following hybridization to the DMPK transcript, and/or
    ii) preventing a protein or nucleic acid from binding to the DMPK transcript; and
  b) an antibody or antigen binding fragment: wherein the antibody or antigen binding fragment comprises a heavy chain variable domain that is at least 95% identical to the amino acid sequence of SEQ ID NO: 13, or a humanized variant thereof, and a light chain variable domain that is at least 95% identical to the amino acid sequence of SEQ ID NO: 14, or a humanized variant thereof; wherein the antibody or antigen binding fragment promotes delivery of the antisense oligonucleotide into muscle cells.

2. The conjugate of claim 1, wherein the antibody or antigen binding fragment comprises a heavy chain variable domain comprising the amino acid sequence of SEQ ID NO: 13, or a humanized variant thereof, and a light chain variable domain comprising the amino acid sequence of SEQ ID NO: 14, or a humanized variant thereof.

3. The conjugate of claim 1, wherein the antisense oligonucleotide is a gapmer or a morpholino.

4. The conjugate of claim 1, wherein the antisense oligonucleotide hybridizes to CUG repeats to at least a portion of the 3'UTR of a DMPK transcript.

5. The conjugate of claim 1, wherein the antisense oligonucleotide hybridizes to any one of SEQ ID NOs: 24-27.

6. The conjugate of claim 1, wherein the antisense oligonucleotide is a single stranded oligonucleotide.

7. The conjugate of claim 1, wherein the antisense oligonucleotide comprises 14, 15, 16, 17, 18, 19, or 20 nucleotides.

8. The conjugate of claim 1, wherein the antisense oligonucleotide comprises 14-30 nucleotides.

9. The conjugate of claim 1, wherein the antisense oligonucleotide comprises a central portion of at least 7 nucleotides, which central portion of at least 7 nucleotides is capable of mediating RNase H-mediated degradation following hybridization to RNA.

10. The conjugate of claim 1, wherein the antisense oligonucleotide sterically inhibits binding of MBNL1 to a nucleotide sequence.

11. The conjugate of claim 1, wherein the antisense oligonucleotide prevents a protein or nucleic acid from binding to any one of SEQ ID NOs: 24-27.

12. The conjugate of claim 9, wherein the central portion of at least 7 nucleotides is composed of unmodified DNA nucleotides, modified nucleotides, or a combination thereof.

13. The conjugate of claim 12, wherein modified nucleotides are phosphorothioate nucleotides.

14. The conjugate of claim 1, wherein the antisense oligonucleotide comprises two wing portions, each of which flank the central portion.

15. The conjugate of claim 14, wherein each of the two wing portions comprises at least 3 nucleotides.

16. The conjugate of claim 14, wherein all of the nucleotides of each of the two wings comprise modified nucleotides of the same class of modification selected from one of the following: locked nucleic acid (LNA) nucleotides, 2'-O-methoxyethyl nucleotides, 2'-O-methyl nucleotides, a peptide nucleic acid, a hexitol nucleic acid, an N3'-P5'-phosphoroamidate, or conformationally restricted nucleotides (CRN).

17. The conjugate of claim 16, wherein the antisense oligonucleotide that binds to the DMPK transcript comprises the primary nucleotide sequence set forth in any of SEQ ID NOs: 9-12 or 22-23.

18. The conjugate of claim 17, wherein the two wing portions of the antisense oligonucleotide comprise LNA nucleotides or 2'-O-methoxyethyl nucleotides.

19. The conjugate of claim 17, wherein the two wing portions of the antisense oligonucleotide comprise CRN nucleotides.

20. The conjugate of claim 1, wherein the conjugate comprises an antigen binding fragment, and the antisense oligonucleotide is conjugated to the C-terminus of the antigen binding fragment.

21. The conjugate of claim 1, wherein the conjugate comprises an antigen binding fragment, and the antisense oligonucleotide is conjugated to the N-terminus of the antigen binding fragment.

22. The conjugate of claim 1, wherein the conjugate comprises an antibody, and the antisense oligonucleotide is conjugated to an Fc portion of the antibody.

23. The conjugate of claim 22, wherein a free cysteine is added to the antibody or antigen binding fragment, and the antisense oligonucleotide is conjugated by site directed chemical conjugation via the free cysteine.

24. The conjugate of claim 1, wherein the ratio of antisense oligonucleotide conjugated per antibody or antigen binding fragment is 1:1.

25. The conjugate of claim 1, wherein the antisense oligonucleotide hybridizes to at least a portion of the 3'UTR region of the DMPK transcript.

26. The conjugate of claim 25, wherein the antisense oligonucleotide hybridizes to a DMPK transcript and promotes degradation of the transcript.

27. The conjugate of claim 1, wherein the conjugate further comprises a muscle blind polypeptide (MBNL1), or a functional fragment thereof comprising all four zinc finger motifs, interconnected to the antibody or antigen fragment thereof.

28. A conjugate comprising
a MBNL1 polypeptide or a functional fragment thereof comprising all four zinc finger motifs;
an antibody or antigen binding fragment, wherein the antibody or antigen binding fragment comprises a heavy chain variable domain that is at least 95% identical to the amino acid sequence of SEQ ID NO: 13, or a humanized variant thereof, and a light chain variable domain that is at least 95% identical to the amino acid sequence of SEQ ID NO: 14, or a humanized variant thereof; wherein the antibody or antigen binding fragment promotes delivery of the antisense oligonucleotide into muscle cells; and
an antisense oligonucleotide that hybridizes to a DMPK transcript; wherein the oligonucleotide is capable of:
  i) mediating RNase H-mediated degradation following hybridization to the DMPK transcript, and/or
  ii) preventing a protein or nucleic acid from binding to the DMPK transcript.

29. A composition comprising the conjugate of claim 1 formulated in a physiologically acceptable carrier.

30. The composition of claim 29, wherein said composition is substantially pyrogen-free.

31. A method of treating myotonic dystrophy, comprising administering to a patient in need thereof a conjugate of claim 1.

32. A method of promoting entry into muscle cells, comprising contacting cells or administering to a patient a conjugate of claim 1.

33. A method of treating myotonic dystrophy, comprising administering to a patient in need thereof two therapeutics, either simultaneously or concurrently, and wherein the therapeutics comprise:
a conjugate of claim 1; and
a chimeric polypeptide comprising:
  (a) an MBNL1 polypeptide or a functional fragment thereof comprising all four zinc finger motifs; and
  (b) an antibody or antigen binding fragment; wherein the antibody or antigen binding fragment comprises a heavy chain variable domain that is at least 95% identical to the amino acid sequence of SEQ ID NO: 13, or a humanized variant thereof, and a light chain variable domain that is at least 95% identical to the amino acid sequence of SEQ ID NO: 14, or a humanized variant thereof; wherein the antibody or antigen binding fragment promotes delivery of the antisense oligonucleotide into muscle cells.

34. A kit comprising
a first container comprising the conjugate of claim 1; and
a second container comprising a chimeric polypeptide comprising:
  (a) an MBNL1 polypeptide or a functional fragment thereof comprising all four zinc finger motifs; and
  (b) an antibody or antigen binding fragment; wherein the antibody or antigen binding fragment comprises a heavy chain variable domain that is at least 95% identical to the amino acid sequence of SEQ ID NO: 13, or a humanized variant thereof, and a light chain variable domain that is at least 95% identical to the amino acid sequence of SEQ ID NO: 14, or a humanized variant thereof; wherein the antibody or antigen binding fragment promotes delivery of the antisense oligonucleotide into muscle cells.

35. The kit of claim 34, comprising instructions for research or therapeutic use.

36. The kit of claim 34, comprising suitable buffers to reconstitute a lyophilized agent in either the first or the second container.

37. The conjugate of claim 1, wherein the antisense oligonucleotide is a gapmer, and wherein the antisense oligonucleotide comprises phosphorothioate nucleotides and locked nucleic acid (LNA) nucleotides.

38. The conjugate of claim 37, wherein the antibody or antigen binding fragment comprises a heavy chain variable domain comprising the amino acid sequence of SEQ ID NO: 13, or a humanized variant thereof, and a light chain variable domain comprising the amino acid sequence of SEQ ID NO: 14, or a humanized variant thereof.

* * * * *